(12) United States Patent
Batchelor et al.

(10) Patent No.: US 6,579,983 B1
(45) Date of Patent: Jun. 17, 2003

(54) 5-CYANO-2-AMINOPYRIMIDINE DERIVATIVES

(75) Inventors: Mark James Batchelor, Watlington (GB); David Festus Charles Moffat, Maidonhead (GB); Jeremy Martin Davis, Workingham (GB); Martin Clive Hutchings, Wokingham (GB)

(73) Assignee: Celltech R&D Limited, Slough (GB)

( * ) Notice: Subject to any disclaimer, the term of this patent is extended or adjusted under 35 U.S.C. 154(b) by 0 days.

(21) Appl. No.: 09/596,952

(22) Filed: Jun. 16, 2000

(30) Foreign Application Priority Data

Jun. 18, 1999 (GB) .............................. 9914258

(51) Int. Cl.[7] .................. C07D 239/42; C07D 401/04; C07D 403/12; C07D 409/04
(52) U.S. Cl. ........................ 544/330; 544/331; 544/332
(58) Field of Search ................... 514/275; 544/324, 544/330, 331, 332

(56) References Cited

U.S. PATENT DOCUMENTS

| | | | |
|---|---|---|---|
| 3,947,467 A | 3/1976 | Verge et al. | 260/310 R |
| 4,012,495 A | 3/1977 | Schmiechen et al. | 514/424 |
| 4,015,017 A | 3/1977 | Gazave et al. | 514/687 |
| 4,153,713 A | 5/1979 | Huth et al. | 514/423 |
| 4,193,926 A | 3/1980 | Schmiechen et al. | 548/517 |
| 4,303,649 A | 12/1981 | Jones | 514/8 |
| 4,548,940 A | 10/1985 | Ife | 514/272 |
| 4,659,363 A * | 4/1987 | Hubele et al. | 71/92 |
| 4,694,009 A | 9/1987 | Hubele et al. | 514/269 |
| 4,788,195 A | 11/1988 | Torley et al. | 514/252 |
| 4,792,561 A | 12/1988 | Walker et al. | 514/312 |
| 4,876,252 A | 10/1989 | Torley et al. | 514/224.8 |
| 4,897,396 A | 1/1990 | Hubele | 514/275 |
| 4,921,862 A | 5/1990 | Walker et al. | 514/312 |
| 4,966,622 A | 10/1990 | Rempfler et al. | 71/92 |

(List continued on next page.)

FOREIGN PATENT DOCUMENTS

| | | |
|---|---|---|
| DE | 250 1443 | 7/1975 |
| DE | 34 36 380 A1 | 4/1986 |
| EP | 0 233 461 A2 | 8/1987 |
| EP | 0 295 210 A1 | 12/1988 |
| EP | 0 337 943 A2 | 10/1989 |
| EP | 0 393 500 A1 | 10/1990 |
| EP | 0 490 823 A1 | 6/1991 |
| EP | 0 470 805 A1 | 2/1992 |
| EP | 0 497 564 A1 | 8/1992 |
| EP | 0 511 865 A1 | 11/1992 |
| EP | 0 537 742 A2 | 4/1993 |
| EP | 0 564 409 A1 | 10/1993 |
| FR | 1 285 932 | 8/1972 |
| FR | 2 545 356 A1 | 11/1984 |
| GB | 2 313 422 | 12/1976 |

(List continued on next page.)

OTHER PUBLICATIONS

Boschelli, Diane H.; et al, J. Med. Chem., 41(22), 4365–4377 1998.*

Schmidt, Hans Werner; Koitz, Gerald; Junek, Hans, J. Heterocycl. Chem., 24(5), 1305–7 (English) 1987.*

Hawley, Gessner, The Condensed Chemical Dictionary, 1977, Van Nostrand, New York.*

Aiello, L.P., et al., "Suppression of retinal neovascularization in vivo by inhibition of vascular endothelial growth factor (VEGF) using soluble VEGF–receptor chimeric proteins," *Proc. Natl. Acad. Sci.,* 1995, 92, 10457–10461.

Boschelli, D.H., et al., "Synthesis and tyrosine kinase inhibitory activity of a series of 2–amino–8H–pyrido[2,3–d] pyrimidines: identification of potent, selective platelet–derived growth factor receptor tyrosine kinase inhibitors," *J. Med. Chem.,* 1998, 41, 4365–4377.

Parangi, S., et al., "Antiangiogenic therapy of transgenic mice impairs de novo tumor growth," *Proc. Natl. Acad. Sci.,* 1996, 93, 2002–2007.

Schmidt, H., et al., "A convenient synthesis of 2–substituted 4–amino–5–pyrimidinecarbonitries," *Inst. of Organic Chemistry,* 1987, 1305–1307.

"The Condensed Chemical Dictionary," Library of Congress Publication Data, Cat. Card. No. 76–19024, 1977, p. 25.

Ames, D.E. et al., "Some Dipyridylalkanes", *J. Chem. Soc.,* 1962, 1475–1481.

(List continued on next page.)

*Primary Examiner*—Mukund J. Shah
*Assistant Examiner*—Thomas McKenzie
(74) *Attorney, Agent, or Firm*—Woodcock Washburn LLP

(57) ABSTRACT

Pyrimidines of formula (1) are described

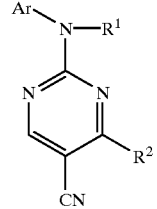

(1)

wherein

Ar is an optionally substituted aromatic or heteroaromatic group;

$R^1$ is a hydrogen atom or a straight or branched chain alkyl group;

$R^2$ is a —$X^1$—$R^3$ group where $X^1$ is a direct bond or a linker atom or group, and $R^3$ is an optionally substituted aliphatic, cycloaliphatic, heteroaliphatic, heterocycloaliphatic, aromatic or heteroaromatic group;

and the salts, solvates, hydrates and N-oxides thereof.

The compounds are selective KDR Kinase and/or FGFr Kinase inhibitors and are of use in the prophylaxis and treatment of disease states assoicated with angiogenesis.

5 Claims, No Drawings

U.S. PATENT DOCUMENTS

| | | | |
|---|---|---|---|
| 4,971,959 A | 11/1990 | Hawkins | 514/150 |
| 4,973,690 A | 11/1990 | Rempfler et al. | 544/279 |
| 4,987,132 A | 1/1991 | Mase et al. | 514/252 |
| 5,124,455 A | 6/1992 | Lombardo | 546/181 |
| 5,128,358 A | 7/1992 | Saccomano et al. | 514/392 |
| 5,159,078 A | 10/1992 | Rempfler et al. | 544/330 |
| 5,164,372 A | 11/1992 | Matsuo et al. | 514/19 |
| 5,175,167 A | 12/1992 | Zipperer et al. | 514/277 |
| 5,177,085 A | 1/1993 | Naef | 514/307 |
| 5,236,918 A | 8/1993 | Amschler et al. | 514/247 |
| 5,274,002 A | 12/1993 | Hawkins | 514/530 |
| 5,298,511 A | 3/1994 | Waterson | 514/311 |
| 5,326,898 A | 7/1994 | Chandraratna | 560/17 |
| 5,340,827 A | 8/1994 | Beeley et al. | 514/352 |
| 5,491,147 A | 2/1996 | Boyd et al. | 514/247 |
| 5,521,184 A | 5/1996 | Zimmermann | 514/252 |
| 5,550,137 A | 8/1996 | Beeley et al. | 514/354 |
| 5,580,888 A | 12/1996 | Warrellow et al. | 514/332 |
| 5,593,997 A | 1/1997 | Dow et al. | 514/258 |
| 5,608,070 A | 3/1997 | Alexander et al. | 546/270 |
| 5,622,977 A | 4/1997 | Warrellow et al. | 514/336 |
| 5,633,257 A | 5/1997 | Warrellow et al. | 514/277 |
| 5,674,880 A | 10/1997 | Boyd et al. | 514/307 |
| 5,691,376 A | 11/1997 | Caggiano et al. | 514/532 |
| 5,693,659 A | 12/1997 | Head et al. | 514/357 |
| 5,698,711 A | 12/1997 | Palfreyman | 549/66 |
| 5,716,967 A | 2/1998 | Kleinman | 514/313 |
| 5,723,460 A | 3/1998 | Warrellow et al. | 514/247 |
| 5,728,708 A | 3/1998 | Zimmermann | 514/275 |
| 5,739,144 A | 4/1998 | Warrellow et al. | 514/277 |
| 5,753,663 A | 5/1998 | Flippin et al. | 514/257 |
| 5,776,958 A | 7/1998 | Warrellow et al. | 514/345 |
| 5,780,477 A | 7/1998 | Head et al. | 514/277 |
| 5,780,478 A | 7/1998 | Alexander et al. | 514/277 |
| 5,786,354 A | 7/1998 | Warrellow et al. | 514/277 |
| 5,798,373 A | 8/1998 | Warrellow | 514/357 |
| 5,849,770 A | 12/1998 | Head et al. | 514/357 |
| 5,851,784 A | 12/1998 | Owens et al. | 435/19 |
| 5,859,034 A | 1/1999 | Warrellow et al. | 514/357 |
| 5,866,593 A | 2/1999 | Warrellow et al. | 514/336 |
| 5,891,896 A | 4/1999 | Warrellow et al. | 514/357 |
| 5,922,741 A | 7/1999 | Davis et al. | 514/341 |
| 6,057,329 A | 5/2000 | Davis et al. | 514/267 |
| 6,080,790 A | 6/2000 | Boyd et al. | 514/650 |
| 6,093,716 A | 7/2000 | Davis et al. | 514/253 |
| 6,096,747 A | 8/2000 | Beeley et al. | 514/256 |

FOREIGN PATENT DOCUMENTS

| | | |
|---|---|---|
| GB | 1588639 | 4/1981 |
| JP | 61/112059 A2 * | 5/1986 |
| JP | 61-112059 | 5/1986 |
| JP | 3-77872 | 4/1991 |
| JP | 3-77923 | 4/1991 |
| WO | WO 86/02353 | 4/1986 |
| WO | WO 87/06576 | 11/1987 |
| WO | WO 91/15451 | 10/1991 |
| WO | WO 91/16892 | 11/1991 |
| WO | WO 92/00968 | 1/1992 |
| WO | WO 92/06085 | 4/1992 |
| WO | WO 92/06963 | 4/1992 |
| WO | WO 92/07567 | 5/1992 |
| WO | WO 92/12961 | 8/1992 |
| WO | WO 92/19594 | 11/1992 |
| WO | WO 92/19602 | 11/1992 |
| WO | WO 93/10118 | 5/1993 |
| WO | WO 93/19748 | 10/1993 |
| WO | WO 94/02465 | 2/1994 |
| WO | WO 94/10118 | 5/1994 |
| WO | WO 94/12461 | 6/1994 |
| WO | WO 94/13661 | 6/1994 |
| WO | WO 94/14742 | 7/1994 |
| WO | WO 94/20446 | 9/1994 |
| WO | WO 94/20455 | 9/1994 |
| WO | WO 95/04046 | 2/1995 |
| WO | WO 95/09847 | 4/1995 |
| WO | WO 95/09851 | 4/1995 |
| WO | WO 95/09852 | 4/1995 |
| WO | WO 95/09853 | 4/1995 |
| WO | WO 95/17386 | 6/1995 |
| WO | WO 95/31451 | 11/1995 |
| WO | WO 95/33727 | 12/1995 |
| WO | WO 95/35281 | 12/1995 |
| WO | WO 95/35283 | 12/1995 |
| WO | WO 96/14843 | 5/1996 |
| WO | WO 97/09297 | 3/1997 |
| WO | WO 97/09325 | 3/1997 |
| WO | WO 98/28281 | 7/1998 |
| WO | WO 98/58926 | 12/1998 |
| WO | WO 99/31073 | 6/1999 |
| WO | 9931073 A1 * | 6/1999 |
| WO | WO 00/27825 | 5/2000 |
| WO | 2000027825 A1 * | 5/2000 |

OTHER PUBLICATIONS

Ashton, M.J., et al., "Selective Type IV Phosphodiesterase Inhibitors as Antiasthmatic Agents. The Syntheses and Biological Activities of 3–(Cyclopentyloxy)–4–methoxybenzamides and Analogues", *J. Med. Chem.*, 1994, 37, 1696–1703.

Barton, D. et al., "A useful synthesis of pyrroles from nitroolefins", *Tetrahedron*, 1990, 46(21), 7587–7598 (HCA-PLUS 1991:163917, 3 pages).

Beavo & Reifsnyder, "Primary Sequence of Cyclic Nucleotide Phosphodiesterase Isozymes and the Design of Selective Inhibitors" *TIPS*, 1990, 11, 150–155.

Buu–Hoi, N.P. et al., "Bromination of Some 1,2,2–Triarylethylenes" *J. Organic Chemistry*, 1958, 23, 1261–1263.

Buu–Hoi et al., "New Method for the Synthesis of ω,ω–Diarylacetophenones Aminated in the Aromatic Nucleus, Polynitration of Triarylethylenes", 1964, 61(13), 16006h, Reported on CAS, *Chem. Abst. Bull. Soc. Chim. France*, 1964, 8, 1842–1844.

Bortolus et al., "cis–trans Isomerization of azastilbenes photosensitized by biacetyl", *Mol. Photochem.*, 1970, 2(4), 311–321, CAPLUS accession No. 1971–434722, 2 pages.

Chan, A.C. et al., "The Role of Protein Tyrosine Kinases and Protein Tyrosine Phosphatases in T Cell Antigen Receptor Signal Transduction", *Annu. Rev. Immunol.*, 1994, 12, 555–592.

Chatterjee, A. et al., "Total Synthesis of Ring–C Aromatic 18–Nor Steroid", *Tetrahedron*, 1980, 36, 2513–2519.

Chemical Abstracts, "Hypoglycemic Pharmaceuticals Containing Manzammide Derivatives", *Chem. Abstr.*, 1983, 99(6), No. 43558Z, Reported as JP Patent.

Chemical Abstracts. Registry Handbook—Number Section. Printed Issues Columbus US *compounds with registry Nos. 95992–21–5 (CARHBT)RN1) 1RN–1648RN (1985); 95971–60–01 (CARHBT(RN1) 1RN–1648RN(1985); 90053–37–5 (CARHBT(RM1) 1RM–1426RM(1984); 82668–18–6 (CARHBT(RK2) 1515RK–2955RK(1982); 80395–25–1 (CARHBT(RK1) 1RK–1514RK(1982); 49610–49–3 (CARHBT(RC1) 1RC–1650RC(1974).

Chemical Abstracts, Registry No. 2732–15–2, prior to 1967, 1 page.

Chemical Abstracts, Registry No. 4593–13–9, prior to 1967, 1 page.

Clayton, S.E. et al., "Direct Aromatic tert–Butylation during the Synthesis of Thiochroman–4–ones", *Tetrahedron*, 1993, 49(4), 939–946.

Collins, R.F. et al., "The Chemotherapy of Schistosomiasis. Part IV. Some Ethers of 4–Amino–2–methoxyphenol", *J. Chem. Soc.,* 1961, 1863–1879.

Daves, G.D. et al., "Pyrimidines. XIII. 2– and 6–Substituted 4–Pyrimidinecarboxylic Acids", *J. Het. Chem.,* 1964, 1, 130–133.

Degani, I. et al., "Cationi etero–aromatici Nota VI—Sintesi di alcuni derivati del perclorato di tiacromilio", *Boll. Sci. Fac. Chim. Ind. Bologna,* 1966, 24(2–3), 75–91 (English Summary Only).

Dietl, F. et al., "Chinone von Benzo–und Dibenzokroneneth-ern", *Synthesis,* 1985, 626–631 (English summary only).

Dent, G., et al., "Inhibition of eosinophil cyclic nucleotide PDE activity and opsonised zymosan–stimulated respiratory burst by 'type IV'–selective PDE inhibitors", *Br. J. Pharmacol.,* 1991, 103, 1339–1346.

El Wakil et al., "Study of the proton magnetic resonance of methoxytamoxifen towards ortho–substitiution", *Chem. Abstr.,* 1992, 116, 255248t, Reported in CAS, Soectrisc, Kett,m 1992, 25(3), 401–407.

Fitzgerald, J.J. et al., "Reaction of benzocyclobutene oxides with nitriles: synthesis of hypecumine and other 3–substituted isoquinolines", *Tetrahedron Lett.,* 1994, 35(49), 9191–9194 (HCAPLUS 1995:272292, 2 pages).

Geissler, J.F. et al., "Thiazolidine–Diones. Biochemical and Biological Activity of a Novel Class of Tyrosine Protein Kinase Inhibitors", *J. Biol. Chem.,* 1990, 265(36), 22255–22261.

Grammaticakis, P., "Contribution A L'Etude de L'Absortion Dans L'Ultraviolet Moyen Et Le Visible Des N–Aroyl–Arylamines. IV. 2,3–, 3,4– et 2,4–, dimethoxybenzoylarylamines", *Bulletin dela Societa Chemique de France,* 1965, 848–858.

Griffin, R.W. et al., "1–Methyl–7–halo–2–naphthalenecarboxylic Acid Derivatives", *J. Organic Chem.,* 1964, 29(8), 2109–2116.

Gupta, A.S. et al., "Friedel–Crafts Condensation of Ethyl Allylmalonate with Anisole", *Tetrahedron,* 1967, 23, 2481–2490.

Hanks, S.K. et al., "The eukaryotic protein kinase superfamily: kinase (catalytic) domain structure and classification", *FASEB J.,* 1995, 9, 576–596.

Hanna, M.M. et al., "Synthesis and antimicrobial activity of some substituted 3–aryl–5–benzylidene–2–phenyl–4–imidazolone derivatives", *Bull. Fac. Pharm.,* 1994, 32(3), 353–359 (HCAPLUS 1996:586501, 2 pages).

Hart, H., et al., "Alkylation of Phenol with a Homoallylic Halide", *J. Am. Chem. Soc.,* 1963, 85, 3269–3273.

Heaslip, R.J., et al., "Phosphodiesterase–IV Inhibition, Respiratory Muscle Relaxation and Bronchodilation by WAY–PDA–641", *J. Pharm. Exper. Ther.,* 1994, 268(2), 888–896.

Hirose, H., et al., ."Styrene Derivatives and Electrophotoraphic Photoreceptor Containing Them", *Chem. Abstr.,* 1993, 118, 136183z, Japanese Patent.

Ife, R.J., "Aminopyrimidinone derivaties as histamine H1–antagonists", CAPLUS Abstract No. 101:211163, Registry No. 92993–05–0, Jul. 4, 1984, 2 pages, EPO Patent.

Ishikura, M. et al., "An Efficient Synthesis of 3–Heteroarylpyridines via Diethyl–(3–pyridyl)–borane" *Synthesis,* 1984, 936–938.

Iwashita, S. et al., "Signal Transduction System for Growth Factor Receptors Associated with Tyrosine Kinase Activity: Epidermal Growth Factor Receptor Signaling and Its Regulation", *Cellular Signalling,* 1992, 4(2), 123–132.

Johnson, A.T., et al., "Identification of Retinoic Acid Receptor β Subtype Specific Agonists", *J. Med. Chem.,* 1996, 39(26), 5027–5030.

Kaiser, E.M., et al., "Selective metalations of methylated pyridines and quinolones", *J. Org. Chem.,* 1973, 38(1), 71–75, CAPLUS accession No. 1973–71853, 2 pages.

Karlsson, J.A., et al., "Anti–inflammatory effects of novel selective cyclic nucleotide phosphodiesterase inhibitors," in "T–Lymphocyte and Inflammatory Cell Research in Asthma", Joller, G. et al. (eds.), Academic Press, 1993, 323–347.

Kefalas, P. et al., "Signalling by the $p60^{c-src}$ Family of Protein–Tyrosine Kinases", *Int. J . Biochem. Cell Biol.,* 1995, 1995, 27(6), 551–563.

Kroon, A.P., et al., "One the occurrence of an $S_n$(ANRORC) mechanism in the amination of 2–substituted 4–phenylpyrimidines with potassium amide in liquid ammonia," *J. Royal Netherlands Chem. Soc.,* 1974, 93(12), 325–328.

Lehmann, J. et al., "Lactones; XIII. Grignard Reaction Followed by Phase–Transfer Oxidation: A Convenient Synthesis of γ,γ–Distributed γ–Butyrolactones from γ–Butyrolactone", *Synthesis,* 1987, 1064–1067 (English abstract only).

Lisle, H. et al., "IL–5–Induced Eosinophilia in the Rat Pleural Cavity: the Effect of Dexamathasone and Indomethacin", *Br. J. Pharmacol.* 1993, 108, 230.

Livi, G.P., et al., "Cloning and Expression of cDNA for a Human Low–$K_m$, Rolipram–sensitive Cyclic AMP Phosphodiesterase", *Molecular and Cellular Biol.* 1990, 10(6), 2678–2686.

Manhas, M.S., et al., "heterocyclic Compounds XII. Quinazoline Derivatives as Potential Antifertility Agents(1)" *J. Heterocyclic Chem.,* 1979, 16, 711–715.

Mathison, I.W., et al., "Synthesis and Hypotensive Properties of Tetrahydroisoquinolines", *J. Med. Chem.,* 1973, 16(4), 332–336.

Meyers, A.I. et al., "Oxazolines. XI. Synthesis of Functionalized Aromatic and Aliphatic Acids. A Useful Protecting Group for Carboxylic Acids Against Grignard and Hydride Reagents", *J. Org. Chem.* 1974, 39(18), 2787–2793.

Meyers, A.I. et al., "The Synthesis of 2–Pyridones from Cyclic Cyano Ketones. A New Aromatization Procedure for Dihydro–2–pyridones", *J. Org. Chem.,* 1964, 29, 1435–1438.

Mezheritskaya, L. V., et al., "Synthesis and properties of carboxonium het=erocyclic systems. VII. Synthesis and properties of 2–benzyl–substituted 1,3–dioxolanium salts", *Chem. Abstr.,* 1980, 93, 95160j, 635, Zh. Org. Khim, 1980, 16(1), 183–188.

Mitsunobu, O., "The Use of Diethyl Azodicarboxylate and Triphenylphosphine in Synthesis and Transformation of Natural Products", *Synthesis,* 1981, 1–28.

Miyaura, N. et al., "The Palladium–Catalyzed Cross–Coupling Reaction of Phenylboronic Acid with Haloarenes in the Presence of Bases", *Synth. Comm.,* 1981, 11(7), 513–519.

Nanjo, K., et al., "Preparation of 2–anilinopyrimidines as agricultural fungicides", *Chem. Abstr.,* 1992, 116(21), No. 116:209703q, JP Patent.

Newton, A.C., "Protein Kinase C: Structure, Function, Regulation", *J. Biol. Chem.,* 1995, 270(48), 28495–28498.

Nicholson, C.D., et al., "Differential Modulation of Tissue Function and Therapeutic Potential of Selective Inhibitors of Cyclic Nucleotide Phosphodiesterase isoenzymes" *TIPS*, 1991, 12, 19–27.

O'Connor, J.J., et al., "Voltammetry and Controlled Potential Oxidation of 3,4–dimethoxypropenylbenzene at a rotating platinum electrode in unbuffered acetonitrile and in acetonitrile–pyridine solution" Reported in *Chem. Abstr.*, 1964, 60(8), #10203.4, J. Electrochem. Soc., 1964, 111(3), 335–343.

Ohtani, Y. et al., "Studies on Pitch Problems Caused by Pulping and Bleaching of Tropical Woods. XIV. Chemistry of the Aurone Derivatives at the Conventional Bleaching Stages", *Acta Chem. Scand.*, 1982, 613–621.

Pickett, W.C. et al., "Modulations of Eicosanoid Biosynthesis by Novel Pyridinylpyrimidines", *Ann. N.Y. Acad. Sci.*, 1994, 744, 299–305.

Pines, J., "Cyclins and cyclin–dependent kinases: take your partners", *TIBS*, 1993, 18, 195–197.

Plé, N. et al., "Metalation of Diazines. XI. Directed Ortho–Lithiation of Fluoropyrimidines and Application to Synthesis of an Azacarboline", *J. Heterocyclic Chem.*, 1994, 31, 1311–1315.

Porter, R.A., et al., "Preparation of 6–phenyl–3–(5–tetrazolyl)–2(H)–one Derivatives as Cyclic AMP–dependent Protein Kinase Agonists", *Chem. Abstr.*, 1992, 117(9), 90296n, PCT Application.

Ramalingam, T., et al., "Synthesis and Pharmacology of 2,5–Disubstituted 1,3,4–Oxadiazoles" J. *Indian Chem. Soc.*, 1981, 58(3), 269–271.

Reddy, K.B., et al., "Inhibition of Breast Cancer Cell Growth in Vitro by a Tyrosine Kinase Inhibitor", *Cancer Research*, 1992, 52, 3636–3641.

Sakakibara, K. et al., "Preparation of N–pyridyl–4–(benzyloxy)benzamides as Cardiotonics", *Chem. Abstr.*, 1988, 108, No. 131583p. JP Patent.

Sánchez, I.H., et al., "Formal Total Synthesis of β–Pipitzol", *Tetrahedron*, 1985, 41(12), 2355–2359.

Schneider, M.R., et al., "Catechol Estrogens of the 1,1,2–Triphenylbut–1–ene Type: Relationship Between Structure, Estradiol Receptor Affinity, Estrogenic and Antiestrogenic Properties, and Mammary Tumor Inhibiting Activities" *J. Med. Chem.*, 1986, 29, 1355–1362.

Seitz, D.E., et al., "Fluorotamoxifen. A Caveat on the Generality of Electrophilic Destannylation" Reported in *Chem. Abstr.*, 1989, 111, 57133k, Synth. Comm., 1988, 18(18), 2353–2357.

Sharp, M.J. et al., "Synthetic Connections to the Aromatic Directed Metalation Reaction. Functionalized Aryl Boronic Acids by pso Borodesilylation: General Synthesis of Unsymmetrical iphenyls and m–Terphenyls", *Tetrahedron Lett.*, 1987, 28(43), 5093–5096.

Spada, A.P. et al., "Small Molecule Inhibitors of Tyrosine Kinase Activity", *Exp. Opin. Ther. Patents*, 1995, 5(8), 805–817.

Takeuchi, I. et al., "On the Antimicrobial Activity and Syntheses of Carbanilide and Salicylanilide Derivatives", Reported in *Chem. Abstr.*, 1983, 98, No. 125577y, Yakugaku Zasshi, 1982, 102(11), 1028–1030.

Thompson, W.J. and Gaudino, J., "A General Synthesis of 5–Arylnicotinates" *J. Org. Chem.*, 1984, 49, 5237–5243.

Tollari, S. et al., "Intramolecular amination of olefins. Synthesis of 2–substituted–4–quinolones from 2–nitrochalcones catalyzed by ruthenium", *J. Chem. Soc. Chem Comm.*, 1994, 15, 1741–1742 (HCAPLUS 1994:605194, 2 pages).

Tominaga, Y., et al., "Polarized Ethylenes. IV. Synthesis of Polarized Ethylenes Using Thioamides and Methyl Dithiocarboxylates and Their Application to Syntheses of Pyrazoles, Pyrimidines, Pyrazolo[3,4–d]pyrimidines, and 5–Aza [2.2.3]cyclazines", *J. Het. Chem.*, 1990, 27, 647–660.

Trost and Fleming (eds.), *Comprehensive Organic Synthesis*, Pergamon Press, New York, 1991, 3, 531–541.

Tsutsumi, K. et al., "Preparation of (Dialkoxyphosphinoylmethyl) benzamides as Antihyperlipidemics", *Chem. Abstr.*, 1990, 113, No. 6599a, UK Patent.

Vidal, J., et al., "Electrophilic Amination: Preparation and Use of N–Boc–3–(4–cyanophenyl)oxaziridine, a New Reagent That Transfers a N–Boc Group to N– and C–Nucleophiles", *J. Org. Chem.*, 1993, 58, 4791–4793.

Yamaguchi, H., "Guanidinobenzene derivatives as anticoagulants", *Chem. Absts.*, 1989, 110, 655 (Abstract No. 94706z), JP Patent.

Yamato, M. et al., "Chemical structure and sweet tast of isocoumarin and related compounds. VI", *Chem. Pharm. Bull.*, 1975, 23(12), 3101–3105 (HCAPLUS 197699154, 2 pages).

Yeadon, M., et al., "Mechanisms Contributing to Ozone–Induced Bronchial Hyperreactivity in Guinea Pigs", *Pulmonary Pharm.*, 1992, 5, 39–50.

Yoneda, T., et al., "The Antiproliferative Effects of Tyrosine Kinase Inhibitors Tyrphostins on a Human Squamous Cell Carcinoma in Vitro and in Nude Mice" *Cancer Research* 1991, 51, 4430–4435.

Zimmerman, J., et al., "Phenylamino–Pyrimidine (PAP) Derivatives: A New Class of Potent and Selective Inhibitors of Protein Kinase C (PKC)", *Arch. Pharm. Pharm. Med. Chem.*, 1996, 329(7), 371–376.

Zimmerman, J., et al., "Phenylamino–Pyrimidine (PAP)— Derivatives: A New Class of Potent and Highly Selective PDGF–Receptor Autophosphorlation Inhibitors," *Bioorg. Med. Chem. Lett.*, 1996, 6(11), 1221–1226.

Zimmerman, J., et al., "Potent and Selective Inhibitors of the ABL–Kinase Phenylamino–Pyrimidine (PAP) Derivatives," *Bioorg. Med. Chem. Lett.*, 1997, 7(2), 187–192.

Per Borgstrom, et al., "Complete inhibition of angiogenesis and growth of microtumors by anti–vascular endothelial growth factor neutralizing antibody: novel concepts of angiostatic therapy from intravital videomicroscopy," *Cancer Res.*, 1996, 56, 4032–4039.

Breier, G., et al., "The role of vascular endothelial growth factor in blood vessel formation," *Trends in Cell Biology*, 1996, 6, 454–456.

Folkman, J., Angiogenesis in cancer, vascular, rheumatoid and other disease, *Nature Medicine*, 1995, 1, 27–31.

Shioiri, T., et al., "New Methods and Reagents in Organic Synthesis. 3. Diethyl Phosphorocyanidate: A New Reagent for C–Acylation", *J. Org. Chem.*, 1978, 43(18), 3631–3632.

* cited by examiner

5-CYANO-2-AMINOPYRIMIDINE DERIVATIVES

This invention relates to substituted 5-cyano-2-aminopyrimidines, to processes for their preparation, to pharmaceutical compositions containing them, and to their use in medicine.

Angiogenesis, the growth of capillaries from existing blood vessels, is an essential process in normal embryonic development, tissue repair and some aspects of female reproductive function. It is also associated with the development of several pathological disorders including solid tumour growth, metastasis, psoriasis and rheumatoid arthritis, as well as diabetic retinopathy and age related macular degeneration [Folkman, Nature Medicine, (1995) 1, 27–310].

Several growth factors have been shown to mediate angiogenesis through alteration of vascular permeability, including vascular endothelial growth factor [VEGF; G. Breier et al., Trends in Cell Biology, (1996), 6, 454–6], platelet derived growth factor (PDGF) and acidic and basic fibroblast growth factors (a & b FGF).

VEGF in dimeric form is a ligand that binds to two transmembrane tyrosine kinase associated receptors, expressed exclusively on proliferating endothelial cells, KDR (Flk-1 in mice) also known as VEGFR-2, and Flt-1 also known as VEGFR-1. Binding of VEGF to KDR/Flk and Flt leads to receptor dimerisation, kinase activation, autophosphorylation of the receptor and phosphorylation of intracellular substrates. An analogous series of events ensues after ligand occupancy of the more widely expressed tyrosine kinase associated FGFr receptor by aFGF or bFGF. Thus receptor tyrosine kinase activity initiates a cellular signalling pathway leading to proliferation.

Antagonism of VEGF with antibody completely suppresses neovascularisation and growth of human rhabdomyosarcoma A673 speroids in athymic mice [Borgstrom et al, Cancer Res., (1996), 56 4032–4039]. Suppression of bFGF gene expression by interferons a and b inhibits capillary density in mice, leading to pancreatic eyelet tumour suppression [Folkman et al, Proc. Natl. Acad.Sci. (1996), 93, 2002 and Singh et al Proc.Natl. Acad. Sci. (1995), 92, 10457). Other receptor associated kinases such as PDGF and EGFr may also have some role in mediating angiogenesis.

We have now found a series of substituted 5-cyano-2-aminopyrimidines which are potent and selective inhibitors of receptor tyrosine kinases involved in angiogenesis, especially KDR kinase and/or FGFr kinase. Selective inhibition of these kinases can be expected to have a beneficial effect and the compounds are thus of use in the prophylaxis and treatment of disease states associated with angiogenesis, as described hereinafter.

Thus, according to one aspect of the invention, we provide a compound of formula (1):

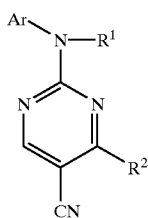

(1)

wherein
Ar is an optionally substituted aromatic or heteroaromatic group;
$R^1$ is a hydrogen atom or a straight or branched chain alkyl group;
$R^2$ is a —$X^1$—$R^3$ group where $X^1$ is a direct bond or a linker atom or group, and
$R^3$ is an optionally substituted aliphatic, cycloaliphatic, heteroaliphatic, heterocycloaliphatic, aromatic or heteroaromatic group; and the salts, solvates, hydrates and N-oxides thereof.

When Ar in the compounds of formula (1) is an aromatic group it may be for example an optionally substituted monocyclic or bicyclic fused ring $C_{6-12}$aromatic group, such as an optionally substituted phenyl, 1- or 2-naphthyl, 1- or 2-tetrahydronaphthyl, indanyl or indenyl group.

When the group Ar in compounds of the invention is a heteroaromatic group it may be an optionally substituted $C_{1-13}$ heteroaromatic group, such as a $C_{1-9}$ heteroaromatic group, containing for example one, two, three or four heteroatoms selected from oxygen, sulphur or nitrogen atoms.

In general, the heteroaromatic group may be for example an optionally substituted monocyclic heteroaromatic, or a bicyclic or tricyclic fused-ring heteroaromatic group. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered fused-ring heteroaromatic groups containing one, two or more heteroatoms selected from oxygen, sulphur or nitrogen atoms. Tricyclic heteroaromatic groups include for example ten- to fourteen-membered fused-ring heteroaromatic groups containing one, two or more heteroatoms selected from oxygen, sulphur or nitrogen atoms. The heteroaromatic group may be attached to the remainder of the compound of formula (1) through any of its ring carbon atoms.

Particular examples of heteroaromatic groups represented by Ar include optionally substituted pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,3,4-triazolyl, 1,2,5-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro] benzofuryl, isobenzofuryl, benzothienyl, benzotriazolyl, isobenzothienyl, indolyl, isoindolyl, 3H-indolyl, benzimidazolyl, indazolyl, imidazo[1,2-a]pyridyl, benzothiazolyl, benzoxazolyl, quinolizinyl, quinazolinyl, phthalazinyl, quinoxalinyl, cinnolinyl, naphthyridinyl, pyrido[3,4-b]pyridyl, pyrido[3,2-b]pyridyl, pyrido[4,3-b] pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

Optional substituents which may be present on the aromatic or heteroaromatic groups represented by Ar include one, two, three or more substituents, each represented by an atom or group —$R^4$ or -Alk($R^4)_m$, where $R^4$ is a halogen atom, or an amino (—$NH_2$), substituted amino, nitro, cyano, hydroxyl (—OH), substituted hydroxyl, formyl, carboxyl (—$CO_2H$), esterified carboxyl, thiol (—SH), substituted thiol, —$COR^5$ [where $R^5$ is a -Alk($R^4)_m$, aryl or heteroaryl group], —$CSR^5$, —$SO_3H$, —$S_2R^5$, —$SO_2NH_2$, —$SO_2NHR^5$, —$SO_2N[R^5]_2$, —$CONH_2$, —$CSNH_2$, —$CONHR^5$, —$CSNHR^5$, —$CON[R^5]_2$, —$CSN[R^5]_2$, —$NHSO_2H$, —$NHSO_2R^5$, —$N[SO_2R^5]_2$, —$NHSO_2NH_2$, —$NHSO_2NHR^5$, —NHSO$_2$N[R$^5$]$_2$, —NHCOR$^5$, —NHCONH$_2$, —NHCONHR$^5$, —NHCON[R$^5$]$_2$, —NHCSR$^5$, —NHC(O)OR$^5$, or optionally substituted cycloaliphatic, heteroycloaliphatic, aryl or heteroaryl group; Alk is a straight or branched C$_{1-6}$ alkylene, C$_{2-6}$ alkenylene or C$_{2-6}$ alkynylene chain, optionally interrupted by one, two or three —O— or —S— atoms atoms or groups selected from —S(O)—, —S(O)$_2$— or —N(R$^6$)— [where R$^6$ is a hydrogen atom or a straight or branched chain C$_{1-6}$ alkyl group]; and m is zero or an integer 1, 2 or 3.

When in the group -Alk(R$^4$)$_m$ m is an integer 1, 2 or 3, it is to be understood that the substituent or substituents R$^4$ may be present on any suitable carbon atom in -Alk. Where more than one R$^4$ substituent is present these may be the same or different and may be present on the same or different atom in -Alk or in R$^4$ as appropriate. Thus for example, -Alk(R$^4$)$_m$ may represent a —CH(R$^4$)$_2$ group, such as a —CH(OH)Ar$^1$ group where Ar$^1$ is an aryl or heteroaryl group as defined below. Clearly, when m is zero and no substituent R$^4$ is present the alkylene, alkenylene or alkynylene chain represented by Alk becomes an alkyl, alkenyl or alkynyl group.

When R$^4$ is a substituted amino group it may be for example a group —NHR$^5$ [where R$^5$ is as defined above] or a group —N[R$^5$]$_2$ wherein each R$^5$ group is the same or different.

When R$^4$ is a halogen atom it may be for example a fluorine, chlorine, bromine, or iodine atom.

When R$^4$ is a substituted hydroxyl or substituted thiol group it may be for example a group —OR$^5$ or —SR$^5$ respectively.

Esterified carboxyl groups represented by the group R$^4$ include groups of formula —CO$_2$Alk$^1$ wherein Alk$^1$ is a straight or branched, optionally substituted C$_{1-8}$ alkyl group such as a methyl, ethyl, n-propyl, i-propyl, n-butyl, i-butyl, s-butyl or t-butyl group; a C$_{6-12}$arylC$_{1-8}$alkyl group such as an optionally substituted benzyl, phenylethyl, phenylpropyl, 1-naphthylmethyl or 2-naphthylmethyl group; a C$_{6-12}$aryl group such as an optionally substituted phenyl, 1-naphthyl or 2-naphthyl group; a C$_{6-12}$ aryloxyC$_{1-8}$alkyl group such as an optionally substituted phenyloxymethyl, phenyloxyethyl, 1-naphthyloxymethyl, or 2-naphthyloxymethyl group; an optionally substituted C$_{1-8}$alkanoyloxyC$_{1-8}$alkyl group, such as a pivaloyloxymethyl, propionyloxyethyl or propionyloxypropyl group; or a C$_{6-12}$ aroyloxyC$_{1-8}$alkyl group such as an optionally substituted benzoyloxyethyl or benzoyloxypropyl group. Optional substituents present on the Alk$^1$ group include R$^4$ substituents described above.

When Alk is present in or as a substituent, it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^6$)— (where R$^6$ is a hydrogen atom or a straight or branched C$_{1-6}$alkyl group) groups.

When R$^4$is present in compounds of formula (1) as an optionally substituted cycloaliphatic group it may be an optionally substituted C$_{3-10}$ cycloaliphatic group. Particular examples include optionally substituted C$_{3-10}$cycloalkyl, e.g. C$_{3-7}$cycloalkyl, or C$_{3-10}$cycloalkenyl e.g. C$_{3-7}$cycloalkenyl groups.

Heterocycloaliphatic groups represented by R$^4$ include the aliphatic or cycloaliphatic groups just described for R$^4$ but with each group additionally containing one, two, three or four heteroatoms or heteroatom-containing groups selected from —O— or —S— atoms or —N(R$^6$)—, —C(O), —C(S)—, —S(O)— or —S(O$_2$)— groups.

Particular examples of R$^4$ cycloaliphatic and heterocycloaliphatic groups include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, 2,4-cyclopentadien-1-yl, 3,5,-cyclohexadien-1-yl, tetrahydrofuranyl, pyrroline, e.g. 2- or 3-pyrrolinyl, pyrrolidinyl, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, 1,4-dioxanyl, morpholinyl, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, oxathiazinyl, e.g. 1,2,5 or 1,2,6-oxathiazinyl, or 1,3,5-oxadiazinyl groups.

Optional substituents which may be present on R$^4$ cycloaliphatic and heterocycloaliphatic groups include one, two, three or more substituents selected from halogen atoms, e.g. fluorine, chlorine, bromine or iodine atoms, or hydroxyl, C$_{1-6}$alkoxy, e.g. methoxy or ethoxy, thiol, C$_{1-6}$alkylthio, e.g. methylthio or ethylthio, hydroxy, C$_{1-6}$alkyl, e.g. hydroxymethyl, hydroxyethyl, —CN, —NO$_2$, —NHR$^5$ or —N(R$^5$)$_2$ groups.

Aryl and heteroaryl groups represented by the groups R$^4$, R$^5$ or Ar$^1$ include for example optionally substituted monocyclic or bicyclic C$_{6-12}$ aromatic groups, e.g. phenyl groups, or C$_{1-9}$ heteroaromatic groups such as those described above in relation to the group Ar. Optional substituents which may be present on these groups include one, two or three R$^{4a}$ atoms or groups described below.

Particularly useful atoms or groups represented by R$^4$, -Alk(R$^4$)$_m$ or R$^{4a}$ as appropriate include fluorine, chlorine, bromine or iodine atoms, or C$_{1-6}$alkyl, e.g. methyl or ethyl, C$_{1-6}$alkylamino, e.g. methylamino or ethylamino, hydroxyC$_{1-6}$alkyl, e.g. hydroxymethyl or hydroxyethyl, hydroxyC$_{2-6}$alkoxy, e.g. 2-hydroxyethoxy or 3-hydroxyethoxy, C$_{1-6}$alkylthiol e.g. methylthiol or ethylthiol, C$_{1-6}$alkoxy, e.g. methoxy or ethoxy, C$_{5-7}$cycloalkoxy, e.g. cyclopentyloxy, haloC$_{1-6}$alkyl, e.g. trifluoromethyl, amino (—NH$_2$), aminoC$_{1-6}$alkyl, e.g. aminomethyl or aminoethyl, C$_{1-6}$dialkylamino, e.g. dimethylamino or diethylamino, aminoC$_{1-6}$alkoxy, C$_{1-6}$alkylaminoC$_{1-6}$alkoxy, diC$_{1-6}$alkylaminoC$_{1-6}$alkoxy, imido, such as phthalimido or naphthalimido, e.g. 1,8-naphthalimido, 1,1,3-trioxobenzo[d]thiazolidino, nitro, cyano, hydroxyl (—OH), formyl [HC(O)—], carboxyl (—CO$_2$H), —CO$_2$Alk$^1$ [where Alk$^1$ is as defined above], C$_{1-6}$ alkanoyl e.g. acetyl, thiol (—SH), thioC$_{1-6}$alkyl, e.g. thiomethyl or thioethyl, —SC(NH$_2$+)NH$_2$, sulphonyl (—SO$_3$H), C$_{1-6}$alkylsulphonyl, e.g. methylsulphonyl, aminosulphonyl (—SO$_2$NH$_2$), C$_{1-6}$alkylaminosulphonyl, e.g. methylaminosulphonyl or ethylaminosulphonyl, C$_{1-6}$dialkylaminosulphonyl, e.g. dimethylaminosulphonyl or diethylaminosulphonyl, phenylaminosulphonyl, carboxamido (—CONH$_2$), C$_{1-6}$alkylaminocarbonyl, e.g. methylaminocarbonyl or ethylaminocarbonyl, C$_{1-6}$dialkylaminocarbonyl, e.g. dimethylaminocarbonyl or diethylaminocarbonyl, sulphonylamino (—NHSO$_2$H), C$_{1-6}$alkylsulphonylamino, e.g. methylsulphonylamino or ethylsulphonylamino, C$_{1-6}$dialkylsulphonylamino, e.g. dimethylsulphonylamino or diethylsulphonylamino, optionally substituted phenylsulphonylamino, e.g. 2-, 3- or 4-substituted phenylsulphonylamino such as 2-nitrophenylsulphonylamino, aminosulphonylamino (—NHSO$_2$NH$_2$), C$_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, phenylaminosulphonylamino, aminocarbonylamino, $C_{1-6}$alkylaminocarbonylamino e.g. methylaminocarbonylamino or ethylaminocarbonylamino, $C_{1-6}$dialkylaminocarbonylamino, e.g. dimethylaminocarbonylamino or diethylaminocarbonylamino, phenylaminocarbonylamino, $C_{1-6}$alkanoylamino, e.g. acetylamino, optionally substituted phenylcarbonylamino, $C_{1-6}$alkanoylamino$C_{1-6}$alkyl, e.g. acetylaminomethyl, $C_{1-6}$alkoxycarbonylamino, e.g. methoxycarbonylamino, ethoxycarbonylamino or t-butoxycarbonylamino, optionally substituted hetero$C_{3-6}$cycloalkyl, e.g. piperidinyl, piperazinyl, 4-($C_{1-6}$alkyl)piperazinyl, e.g. 4-methylpiperazinyl, homopipeprazinyl, or morpholinyl, optionally substituted hetero$C_{3-6}$cycloalkyl$C_{1-6}$alkyl, e.g. piperidinyl$C_{1-6}$alkyl, piperazinyl$C_{1-6}$alkyl, 4-($C_{1-6}$alkyl)piperazinyl$C_{1-6}$alkyl, e.g. 4-methylpiperazinylmethyl, or morpholinyl$C_{1-6}$alkyl, optionally substituted hetero$C_{3-6}$cycloalkyl$C_{1-6}$alkoxy, e.g. morpholinyl$C_{1-6}$alkoxy, optionally substituted hetero$C_{3-6}$alkyl$C_{1-6}$alkylamino, optionally substituted hetero$C_{3-6}$cycloalkylamino, tetrazolyl, optionally substituted imidazolyl, optionally substituted triazolyl, e.g.1,2,4-, 1,2,3-, 1,3,4- or 1,2,5-triazolyl, optionally substituted imidazolyl$C_{1-6}$alkyl, optionally substituted imidazolyl$C_{1-6}$alkoxy, optionally substituted triazolyl$C_{1-6}$alkoxy, optionally substituted imidazolylamino$C_{1-6}$alkoxy, optionally substituted phenylamino, optionally substituted benzylamino, optionally substituted benzyloxy, or optionally substituted pyridylmethylamino group.

Where desired, two $R^4$ or -Alk($R^4$)$_m$ substituents may be linked together to form a cyclic group such as a cyclic ether, e.g. a $C_{2-6}$alkylenedioxy group such as ethylenedioxy.

It will be appreciated that where two or more $R^4$, -Alk($R^4$)$_m$ or $R^{4a}$ substituents are present, these need not necessarily be the same atoms and/or groups.

Especially useful $R^4$, -Alk($R^4$)$_m$ or $R^{4a}$ substituents include for example fluorine, chlorine, bromine or iodine atoms, or a methylamino, ethylamino, hydroxymethyl, hydroxyethyl, methylthiol, ethylthiol, methoxy, ethoxy, n-propoxy, 2-hydroxyethoxy, 3-hydroxypropoxy, 4-hydroxybutoxy, 2-aminoethoxy, 3-aminopropoxy, 2-(methylamino)ethoxy, 2-(dimethylamino)ethoxy, 3-(dimethyl-amino)propoxy, cyclopentyloxy, cyclohexyl, cyclohexylamino, 2-hydroxycyclohexylamino, trifluoromethyl, trifluoromethoxy, methylamino, ethylamino, amino (—NH$_2$), aminomethyl, aminoethyl, dimethylamino, diethylamino, ethyl(methyl)amino, propyl(methyl)amino, 2-hydroxyethylamino, 3-hydroxypropylamino, 4-hydroxybutylamino, 2-aminoethylamino, 3-aminopropylamino, 4-aminobutylamino, 2-(methylamino)ethylamino, 2-(ethylamino)ethylamino, 2-(i-propylamino)ethylamino, 3-(i-propylamino)propylamino, 2-(dimethylamino)ethylamino, 3-(dimethylamino)propylamino, 2-(diethylamino)ethylamino, 3-(diethylamino)propylamino, 2-(methylamino)ethyl(methyl)amino, 3-(methylamino)propyl(methyl)amino, 2-(dimethylamino)ethyl(methyl)amino, 2-(dimethylamino)ethyl(ethyl)amino, dimethylaminoethoxy, nitro, cyano, hydroxyl (—OH), formyl [HC(O)—], carboxyl (—CO$_2$H), —CH$_2$CO$_2$H, —OCH$_2$CO$_2$H, —CO$_2$CH$_3$, —CO$_2$CH$_2$CH$_3$, —CH$_2$CO$_2$CH$_3$, —CH$_2$CO$_2$CH$_2$CH$_3$, —CH$_2$CO$_2$CH$_2$phenyl, t-butoxycarbonylmethoxy, acetyl, phenacetyl thio (—SH), thiomethyl, thioethyl, —SC(NH)NH$_2$, sulphonyl (—SO$_2$H), methylsulphonyl, methylaminosulphonyl, ethylaminosulphonyl, dimethylaminosulphonyl, diethylaminosulphonyl, carboxamido (—CONH$_2$), methylaminocarbonyl, ethylaminocarbonyl, dimethylaminocarbonyl, diethylaminocarbonyl, methylaminocarbonylmethyl, —NHC(S)NH$_2$, sulphonylamino (—NHSO$_2$H), methylsulphonylamino ethylsulphonylamino, dimethylsulphonylamino, diethylsulphonylamino, sulphonylamino (—NHSO$_2$NH$_2$), methylaminosulphonylamino, ethylaminosulphonylamino, dimethylaminosulphonylamino, diethylaminosulphonylamino, methylaminocarbonylamino, ethylaminocarbonylamino, dimethylaminocarbonylamino diethylaminocarbonylamino, acetylamino, phenylcarbonylamino, aminomethylcarbonylamino, acetylaminomethyl, methoxycarbonylamino, ethoxycarbonylamino, t-butoxycarbonylamino, pyrrolidinyl, piperidinyl, piperazinyl, 4-methylpiperazinyl, 4-methylpiperazinyl$C_{1-6}$alkylphenylcarbonylamino, homopiperazinyl, morpholinyl, pyrrolidinyl$C_{1-6}$alkyl, piperidinyl$C_{1-6}$alkyl, piperazinyl$C_{1-6}$alkyl, 4-($C_{1-6}$alkyl)piperazinyl$C_{1-6}$alkyl, morpholinyl$C_{1-6}$alkyl, morpholinoethoxy, 2-pyrrolidinylethylamino, 2-(1-methylpyrrolidinyl)ethylamino, 1-ethylpyrrolidinylmethylamino, piperidinylamino, 1-benzylpiperidinylamino, imidazolyl, 1,2,4-triazolyl, 1,2,3-triazolyl, 1,3,4-triazolyl, 1,2,5-triazolyl, $C_{1-6}$alkylimidazolyl$C_{1-6}$alkyl, imidazolyl$C_{1-6}$alkoxy, triazolyl$C_{1-6}$alkyl, triazolyl$C_{1-6}$alkoxy, imidazolyl$C_{1-6}$alkyl such as imidazlylmethyl or imidazolylethyl, 4-(methoxy)phenylamino, 4-(3-hydroxypropyl)phenylamino, benzylamino, benzyloxy or pyridiylmethylamino group.

In the compounds of formula (1), when the group $R^1$ or the group $R^6$ [when present as —N($R^6$)—] is a straight or branched chain alkyl group it may be for example a $C_{1-6}$ straight or branched chain alkyl group such as a methyl, ethyl, n-propyl or isopropyl group.

Linker atoms represented by $X^1$ when present in compounds of formula (1) include —O— or —S— atoms. When $X^1$ is a linker group it may be for example a —C(O)—, —C(S)—, —S(O)—, —S(O)$_2$, —N(R)$^7$— [where $R^7$ is a hydrogen atom or a $C_{1-6}$ alkyl, e.g. methyl or ethyl, group], —C($R^7$)$_2$—, —CON($R^7$)—, —OC(O)N($R^7$)—, —CSN($R^7$)—, —N($R^7$)CO—, —N($R^7$)C(O)O—, —N($R^7$)CS—, —SON($R^7$), —SO$_2$N($R^7$), —N($R^7$)SO$_2$—, —N($R^7$)CON($R^7$)—, —N($R^7$)CSN($R^7$)—, —N($R^7$)SON($R^7$)— or —N($R^7$)SO$_2$N($R^7$) group.

In the compounds of formula (1), when $R^2$ is —$X^1R^3$ and $R^3$ is an optionally substituted aliphatic group, $R^3$ may be an optionally substituted $C_{1-10}$ aliphatic group for example an optionally substituted straight or branched chain $C_{1-6}$ alkyl, e.g. $C_{1-3}$ alkyl, $C_{2-6}$ alkenyl, e.g. $C_{2-4}$ alkenyl, or $C_{2-6}$ alkynyl, e.g. $C_{2-4}$ alkynyl group. Each of said groups may be optionally interrupted by one or two heteroatoms or heteroatom-containing groups represented by $X^2$ [where $X^2$ is an atom or group as just described for $X^1$], to form an optionally substituted $R^3$ heteroaliphatic group.

Particular examples of aliphatic groups represented by $R^3$ include optionally substituted —CH$_3$, —CH$_2$CH$_3$ —(CH$_2$)$_2$CH$_3$, —CH(CH$_3$)$_2$, —C(CH$_3$)$_3$, —(CH$_2$)$_3$CH$_3$, —CH(CH$_3$)CH$_2$CH$_3$, —CH$_2$CH(CH$_3$)$_2$, —C(CH$_3$)$_3$, —(CH$_2$)$_4$CH$_3$, —(CH$_2$)$_5$CH$_3$, —CHCH$_2$, —CHCHCH$_3$, —CH$_2$CHCH$_2$, —CHCHCH$_2$CH$_3$, —CH$_2$CHCHCH$_3$, —(CH$_2$)$_2$CHCH$_2$, —CCH, —CCCH$_3$, —CH$_2$CCH, —CCCH$_2$CH$_3$, —CH$_2$CCCH$_3$, or —(CH$_2$)$_2$CCH groups. Where appropriate each of said groups may be optionally interrupted by one or two atoms and/or groups $X^2$ to form an optionally substituted heteroaliphatic group. Particular examples include —$CH_2X^2CH_3$, —$CH_2X^2CH_2CH_3$, —$(CH_2)_2X^2CH_3$ and —$(CH_2)_2X^2CH_2CH_3$ groups.

The optional substituents which may be present on these aliphatic and/or heteroaliphatic groups include one, two, three or more substituents selected from halogen atoms, e.g. fluorine, chlorine, bromine or iodine atoms, or hydroxyl, $C_{1-6}$ alkoxy, e.g. methoxy or ethoxy, thiol, $C_{1-6}$ alkylthio, e.g. methylthio or ethylthio, —$SC(NH)NH_2$, —$CH_2C(NH)NH_2$, amino, substituted amino or cyclic amino groups.

Substituted amino groups include for example groups of formulae —$NR^8R^9$ [where $R^8$ is an optionally substituted $C_{1-6}$ alkyl, $C_{2-6}$ alkenyl or $C_{2-6}$ alkynyl group optionally interrupted by one or two heteroatoms or heteroatom-containing groups represented by $X^3$ (where $X^3$ is an atom or group as described above for $X^1$) and $R^9$ is a hydrogen atom or is a group as just defined for $R^8$], —$N(R^9)COR^8$, —$N(R^9)CSR^8$, —$N(R^9)SOR^8$, —$N(R^9)SO_2R^8$, —$N(R^9)CONH_2$, —$N(R^9)CONR^8R^9$, —$N(R^9)C(O)OR^8$, —$N(R^9)C(NH)NH_2$, —$N(R^9)C(N\ H)NR^8NR^9$, —$N(R^9)CSNH_2$, —$N(R^9)CSNR^8R^9$, —$N(R^9)SONH_2$, —$N(R^9)SONR^8R^9$, —$N(R^9)SONH_2$, —$N(R^9)SO_2NH_2$, —$N(R^9)SONR^8R^9$ or —$N(R^9)Cyc^1$ [where $Cyc^1$ is an optionally substituted $C_{3-7}$ monocyclic carbocyclic group optionally containing one or more —O— or —S— atoms or —$N(R^6)$—, —C(O)—, —C(S)—, —S(O)— or —$S(O_2)$— groups].

Cyclic amino substituents which may be present on $R^3$ aliphatic or heteroaliphatic groups include groups of formula —$NHet^1$, where —$NHet^1$ is an optionally substituted $C_{3-7}$ cyclic amino group optionally containing one or more other heteroatoms or heteroatom containing groups selected from —O— or —S— atoms or —$N(R^6)$—, —C(O), —C(S)—, —S(O)— or —$S(O_2)$— groups.

Particular examples of amino, substituted amino and cyclic amino groups include —$NH_2$, methylamino, ethylamino, dimethylamino, diethylamino, —$NHCyc^1$ where $Cyc^1$ is an optionally substituted cyclopentyl, cyclohexyl, pyrrolidinyl, imidazolidinyl, pyrazolidinyl, piperidinyl, morpholinyl, piperazinyl or thiomorpholinyl group, or —$NHet^1$ where —$NHet^1$ is an optionally substituted pyrrolidinyl, imidazolidinyl, pyrazolidinyl, piperidinyl, morpholinyl, piperazinyl or thiomorpholinyl group. Optional substituents which may be present on these groups and substituted and cyclic amino groups in general include one, two or three halogen atoms, e.g. fluorine, chlorine, bromine or iodine atoms, or $C_{1-4}$ alkyl, e.g. methyl or ethyl, —NH2-, —NHCH3-, —$N(CH_3)_2$, hydroxyl, or $C_{1-4}$ alkoxy, e.g. methoxy or ethoxy groups.

When $R^3$ is present in compounds of formula (1) as an optionally substituted cycloaliphatic group it may be an optionally substituted $C_{3-10}$ cycloaliphatic group. Particular examples include optionally substituted $C_{3-10}$ cycloalkyl, e.g. $C_{3-7}$ cycloalkyl, or $C_{3-10}$ cycloalkenyl e.g. $C_{3-7}$ cycloalkenyl groups.

Heteroaliphatic or heterocycloaliphatic groups represented by $R^3$ include the aliphatic or cycloaliphatic groups just described for $R^3$ but with each group additionally containing one, two, three or four heteroatoms or heteroatom-containing groups represented by $X^2$, where $X^2$ is as described above.

Particular examples of $R^3$ cycloaliphatic and heterocycloaliphatic groups include optionally substituted cyclopropyl, cyclobutyl, cyclopentyl, cyclohexyl, cycloheptyl, 2-cyclobuten-1-yl, 2-cyclopenten-1-yl, 3-cyclo-penten-1-yl, 2,4-cyclopentadien-1-yl, 3,5,-cyclohexadien-1-yl, tetrahydro-furanyl, pyrroline, e.g. 2- or 3-pyrrolinyl, pyrrolidinyl, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, 1,4-dioxanyl, morpholinyl, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, oxathiazinyl, e.g. 1,2,5 or 1,2,6-oxathiazinyl, or 1,3,5-oxadiazinyl groups.

Optional substituents which may be present on $R^3$ cycloaliphatic and heterocycloaliphatic groups include $C_{1-6}$ alkyl groups and those optional substituents described above for $R^3$ when it is an aliphatic group. The heterocycloaliphatic groups may be attached to the remainder of the molecule of formula (1) through any appropriate ring carbon or heteroatom.

When $R^3$ is present as an aromatic or heteroaromatic group in compounds of formula (1) it may be for example an optionally substituted aromatic or heteroaromatic group as described above in relation to the group Ar. Optional substituents which may be present on these aromatic or heteroaromatic groups include one, two or three $R^{4b}$ or -Alk $(R^{4b})_m$ substituents where $R^{4b}$ is an atom or group as described above for $R^4$, and Alk and m are as described previously. Particular substituents include optionally substituted $C_{1-6}$ alkyl groups [wherein the optional substituents include one, two or three of those optional substituents described above for $R^3$ when it is an aliphatic group and halogen atoms, e.g. fluorine, chlorine, bromine or iodine atoms or hydroxyl, $C_{1-6}$ alkoxy, e.g. methoxy or ethoxy, thiol, $C_{1-6}$ alkylthio, e.g. methylthio or ethylthio, —$SC(NH)NH_2$, —$CH_2C(NH)NH_2$, amino, substituted amino or cyclic amino groups as described above for the optinoal substituents on aliphatic $R_3$ groups.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, piperazine, dimethylamine or diethylamine salts.

Particularly useful salts of compounds according to the invention include pharmaceutically acceptable salts, especially acid addition pharmaceutically acceptable salts.

It will be appreciated that depending on the nature of the group Ar and the substituent $R^2$, the compounds of formula (1) may exist as tautomers and/or geometrical isomers and/or may have one or more chiral centres so that enantiomers or diastereomers may exist. It is to be understood that the invention extends to all such tautomers and isomers of the compounds of formula (1), and to mixtures thereof, including racemates.

In the compounds according to the invention the aromatic group represented by Ar is preferably a substituted phenyl group. The heteroaromatic group represented by Ar is preferably a substituted five- or six-membered monocyclic heteroaromatic group or a nine- or ten-membered fused-ring heteroaromatic group, each of said groups containing one or two oxygen, sulphur and/or nitrogen atoms. Particularly useful groups of these types include substituted pyridyl, indolyl, benzimidazolyl, indazolyl, benzothiazolyl, quinolyl, isoquinolyl and benzoxazolyl groups. Substituted quinolyl, indazolyl or benzothiazolyl groups are especially useful. The substituent(s) present on any of the above-mentioned preferred Ar groups may be any of those —$R^4$ or -Alk($R^4$)$_m$ atoms or groups, particularly one, two or three —$R^4$ and/or -Alk($R^4$)$_m$ atoms or groups, generally or particularly described above and hereinafter in the Examples. Particularly useful substituents are those which contain one or more basic centres, as described hereinafter. In one preference, at least one —$R^4$ or -Alk($R^4$)$_m$ substituent will contain a basic centre.

In general in compounds of the invention $R^1$ is preferably a hydrogen atom.

In one general preference, $R^2$ in compounds of formula (1) is a group —$X^1R^3$ in which $X^1$ is a direct bond. In these compounds $R^3$ is preferably an optionally substituted aromatic group or an optionally substituted heteroaromatic group containing one or two ring oxygen, sulphur and/or nitrogen atoms and is especially a monocyclic heteroaromatic group. Thus in particular $R^3$ may be an optionally substituted phenyl, thienyl, thiazolyl, indolyl or pyridyl group. The pyridyl group may in general be attached to the remainder of the compound of formula (1) through any available ring carbon atom and is in relation to that carbon atom, a 2-, 3- or 4-pyridyl group. Substituted 3-pyridyl groups are especially useful. Substituents which may be present on these $R^3$ aromatic and heteroaromatic groups include one, two or three —$R^{4b}$ or -Alk($R^{4b}$)$_m$ substituents as described in general and in particular above and hereinafter in the Examples. In one preference, at least one —$R^{4b}$ or -Alk($R^{4b}$)$_m$ substituent will contain a basic centre as described hereinafter.

A particularly useful group of compounds according to the invention has the formula (1) wherein Ar is a substituted phenyl, six-membered monocyclic heteroaromatic group or nine- or ten-membered fused-ring heteroaromatic group, each of said groups containing one or two oxygen, sulphur and/or nitrogen atoms; $R^1$ is a hydrogen atom and $R^2$ is an optionally substituted phenyl, thienyl, thiazolyl or monocyclic or bicyclic heteroaromatic group containing one or two oxygen, sulphur and/or nitrogen atoms.

In compounds of this type, Ar is especially a substituted phenyl, pyridyl, indolyl, indazolyl, benzimidazolyl, benzothiazolyl, quinolyl, isoquinolyl or benzoxazolyl group. Substituted phenyl groups are particularly useful. The group $R^2$ is preferably an optionally substituted thienyl, phenyl, indolyl or pyridyl group.

The substituents which may be present on Ar or $R^2$ groups of these types include one, two or three of those —$R^4$, -Alk($R^4$)$_m$, —$R^{4b}$ and/or -Alk($R^{4b}$)$_m$ substituents generally and particularly described above in relation to compounds of formula (1), especially substituents which contain one or more basic centres. Particularly useful substituents containing basic centres include nitrogen containing groups such as amino, substituted amino and cyclic amino groups, as described above in relation to optional substituents present on $R^3$ aliphatic groups, optionally substituted and nitrogen-containing heteroaromatic groups, particularly five- or six-membered nitrogen-containing monocyclic heteroaromatic groups such as optionally substituted imidazolyl groups.

Particular groups containing basic centres include —$X^{1a}$(Alk$^a$)$_p$NR$^{7a}$R$^{7b}$ (where $X^{1a}$ is a direct bond or a linker atom or group as defined above for $X^1$, Alk$^a$ is as defined above for Alk, p is zero or an integer 1) and $R^{7a}$ and $R^{7b}$ which may be the same or different is each a hydrogen atom or a straight or branched $C_{1-6}$alkyl group, —$X^{1a}$(Alk$^a$)$_p$NHet$^1$ (where —NHet$^1$ is as defined above) and —$X^{1a}$(Alk$^a$)$_p$Ar$^2$ (where Ar$^2$ is a nitrogen containing heteroaromatic group as described above for Ar). In these groups, NR$^{7a}$R$^{7b}$ may in particular be —NHCH$_3$, —N(CH$_3$)$_2$, —NHCH$_2$CH$_3$, —N(CH$_3$)(CH$_2$CH$_3$), or —N(CH$_2$CH$_3$)$_2$, —NHet$^1$ may in particular be optionally substituted pyrrolidinyl, piperidinyl, imidazolidinyl, piperazinyl, morpholinyl, thiomorpholinyl or pyrazolidinyl; Ar$^2$ may in particular be optionally substituted imidazolyl. $X^{1a}$ when present may in particular be an oxygen atom or a —NH— group.

Especially useful —$R^{4b}$ and -Alk($R^{4b}$)$_m$ substituents in compounds of the invention include —NH$_2$, —(CH$_2$)$_2$NH$_2$, —C(CH$_3$)$_2$NH$_2$, —C(CH$_3$)$_2$NHCH$_3$, —C(CH$_3$)$_2$N(CH$_3$)$_2$, —CH$_2$N(CH$_2$CH$_3$)$_2$, —CONH(CH$_2$)$_2$N(CH$_2$CH$_3$)$_2$, —C(CH$_3$)$_2$— pyrrolidinyl, dimethylaminopyrrolidinyl, imidazolyl, imidazolylmethyl, imidazolylethyl and piperidinylethyl groups. Particularly useful —$R^4$ and -Alk($R^4$)$_m$ substituents include fluorine and chlorine atoms and methyl, ethyl, methoxy, —CF$_3$, —CH$_2$F$_2$, —CH$_2$F, —OH, —OCF$_3$, —OCHF$_3$, —OCHF$_2$, —OCH$_2$F, —NO$_2$, —CN, —NH$_2$, —NHCH$_3$, —N(CH$_3$)$_2$, Ar$^{2a}$ where Ar$^{2a}$ is imidazolyl, $C_{1-3}$alkylimidazolyl, triazolyl or $C_{1-3}$alkyl-triazolyl, —$C_{1-3}$alkylAr$^{2a}$, —OC$_{1-3}$alkylAr$^{2a}$, —NHet$^{1a}$, where —NHet$^{1a}$ is piperidinyl, $C_{1-3}$alkylpiperidinyl, morpholinyl, $C_{1-3}$alkylmorpholinyl, pyrrolidinyl, $C_{1-3}$alkylpyrrolidinyl, piperazinyl, $C_{1-3}$alkylpiperazinyl, imidazolidinyl, $C_{1-3}$alkylimiazolidinyl, pyrazolidinyl or $C_{1-3}$alkylpyrazolidinyl, —$C_{1-3}$alkylNHet$^{1a}$, —OC$_{1-3}$alkylNHet$^{1a}$, and —NHCOAr$^3$where Ar$^3$ is phenyl optionally substituted by Ar$^{2a}$, —$C_{1-3}$alkylAr$^{2a}$, —OC$_{1-3}$alkylAr$^{2a}$, —NHet$^1$, —$C_{1-3}$alkylNHet$^1$ and —OC$_{1-3}$ alkyl-NHet$^1$.

In the above preferred groups the term triazolyl is intended to mean all possible isomers as described above in relation to the group Ar and especially includes 1,2,3- and 1,2,4-triazolyl groups.

Particularly useful compounds of the invention include:
5-Cyano-4-phenyl-N-(3,4,5-trimethoxyphenyl)pyrimidine-2-amine;
5-Cyano-N-[4-(2-imidazol-1-ylethyl)phenyl]-4-(4-methoxcarbonylphenyl)pyrimidine-2-amine;
5-Cyano-4-(4-hydroxymethylphenyl)-N-(3,4,5-trimethoxyphenyl)pyrimidine-2-amine;
5-Cyano-4[(4-N,N-diethylaminomethyl)phenyl]-N-(3,4,5-trimethoxyphenyl)pyrimidine-2-amine;
5-Cyano-4-[2-(3(R)-dimethylaminopyrrolidin-1-yl)pyridin-5-yl]-N-(indazol-5-yl)pyrimidine-2-amine;
4-[4-(1-Amino-1-methylethyl)phenyl]-5-cyano-N-(indazol-5-yl)pyrimidine-2-amine;
4-[4-(1-Amino-1-methylethyl)phenyl]-5-cyano-N-(3,4,5-trimethoxyphenyl)pyrimidine-2-amine;
5-Cyano-N-[4-(2-N,N-diethylaminoethylaminocarboxy)phenyl]-4-phenylpyrimidine-2-amine;
5-Cyano-4-phenyl-N-{4-[2-(2-ethylimidazol-1-yl)ethyl]phenyl}-pyrimidine-2-amine;
4-[4-(1-Amino-1-methylethyl)phenyl]-5-cyano-N-4(1,2,3-triazol-1-yl)-phenyl]pyrimidine-2-amine;
4-[4-(1-Amino-1-methylethyl)phenyl]-5-cyano-N-{4-[2-(2-ethylimidazol-1-yl)ethyl]phenyl}pyrimidine-2-amine;
N-[3-(5-Cyano-4-thiophen-2-ylpyrimidin-2-ylamino)phenyl]-4-(4-methylpiperazin-1-ylmethyl)benzamide;
4-[3-(1-Amino-1-methylethyl)phenyl]-5-cyano-N-{4-[2-(2-methylimidazol-1-yl)ethyl]phenyl}pyrimidine-2-amino;

5-Cyano-4-[4-(imiadzol-1-yl)methyl]phenyl-N-(3,4,5-trimethoxyphenyl)pyrimidine-2-amino;
and the salts, solvates, hydrates and N-oxides thereof.

Especially useful compounds according to the invention include:
4-[4-(1-Amino-1-methylethyl)phenyl]-5-cyano-N-[4(1,2,4-triazol-1-yl)phenyl]pyrimidine-2-amine;
5-Cyano-N-[4-(1,2,4-triazol-1-yl)phenyl]-4-[4-(1-dimethylamino-1-methylethyl)phenyl]pyrimidine-2-amine;
4-[4-(1-Amino-1-methylethyl)phenyl]-5-cyano-N-(4-fluorophenyl)pyrimidine-2-amine;
4-[4-(1-Amino-1-methylethyl)phenyl]-5-cyano-N-{4-[2-piperidin-1-ylethyl]phenyl}pyrimidine-2-amine;
4-[4-(1-Amino-1-methylethyl)phenyl]-5-cyano-N-[4-(2-imidazol-1-ylethyl)phenyl]pyrimidine-2-amine;
4-[4-(1-Amino-1-methylethyl)phenyl]-5-cyano-N-[4-(2-morpholinoethyl)phenyl]pyrimidine-2-amine;
4-[4-(1-Amino-1-methylethyl)phenyl]-5-cyano-N-[3-(2-morpholinoethyl)phenyl]pyrimidine-2-amine;
5-Cyano-4-[4-(1-methyl-1-pyrrolidin-1-ylethyl)phenyl]-N-(4-fluorophenyl)pyrimidine-2-amine;
5-Cyano-4-{2-([2-(diethylamino)ethyl]amino)pyridin-5-yl}-N-(4-fluorophenyl)pyrimidine-2-amine;
4-[4-(1-Amino-1-methylethyl)phenyl]-5-cyano-N-(3-fluorophenyl)pyrimidine-2-amine;
and the salts, solvates, hydrates and N-oxides thereof.

Compounds according to the invention are potent and selective inhibitors of KDR and/or FGFr kinases as demonstrated by differential inhibition of these enzymes when compared to inhibition of other protein kinases such as EGFr kinase, p56$^{lck}$ kinase, ZAP-70 kinase, protein kinase C, Csk kinase and p59$^{fyn}$ kinase. The ability of the compounds to act in this way may be simply determined by employing tests such as those described in the Examples hereinafter.

The compounds according to the invention are thus of particular use in the prophylaxis and treatment of diseases in which inappropriate KDR kinase action plays a role, for example in disease states associated with angiogenesis. The compounds are then of use for example in the prophylaxis and treatment of cancer, prosiasis, rheumatoid arthritis, Kaposi's Sarcoma, ischemic heart disease, atherosclerosis and occular diseases, such as diabetic retinopathy, involving retinal vessl proliferation and the invention is to be understood to extend to such uses and to the use of a compound of formula (1) in the preparation of a medicament for the prophylaxis and treatment of such diseases.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection, including bolus injection or infusion or particle mediated injection. Formulations for injection may be presented in unit dosage form, e.g. in glass ampoule or multi dose containers, e.g. glass vials or a device containing a compressed gas such as helium for particle mediated administration. The compositions for bolus injection or infusion may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use. For particle mediated administration the complex may be coated on particles such as microscopic gold particles.

In addition to the formulations described above, the compounds of formula (1) may also be formulated as a depot preparation. Such long acting formulations may be administered by implantation or by intramuscular injection. Where desired, the compounds according to the invention may also be conjugated to a polymer, e.g. a naturally occuring polymer such as albumin, to prolong the half life of the compounds when in use. Such conjugates may be formulated and delivered as described above.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $R^1$, $R^2$, Alk, $Alk^1$ and Ar when used in the text or formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, (1991)]. In some instances, deprotection may be the final step in the synthesis of a compound of formula (1) and the processes according to the invention described hereinafter are to be understood to extend to such removal of protecting groups.

Thus according to a further aspect of the invention, a compound of formula (1) may be prepared by reaction of a guanidine of formula (2):

$$Ar-N(R^1)C(=NH)NH_2 \qquad (2)$$

or a salt thereof
with an enaminone of formula (3):

$$R^2COC(CN)CHN(R^{10})(R^{11}) \qquad (3)$$

where $R^{10}$ and $R^{11}$, which may be the same or different is each a $C_{1-6}$ alkyl group.

The reaction may be performed in a solvent, for example a protic solvent such as an alcohol, e.g. ethanol, methoxyethanol or propan-2-ol, optionally in the presence of a base e.g. an alkali metal base, such as sodium hydroxide or potassium carbonate, at an elevated temperature, e.g. the reflux temperature.

Salts of the compounds of formula (2) include acid salts such as inorganic acid salts e.g. hydrochlorides or nitrates.

Intermediate guanidines of formula (2) may be prepared by reaction of the corresponding amine $ArNH_2$ with cyanamide at an elevated temperature. The reaction may be performed in a solvent such as ethanol at an elevated temperature, e.g. up to the reflux temperature. Where it is desired to obtain a salt of a guanidine of formula (2), the reaction may be performed in the presence of a concentrated acid, e.g. hydrochloric or nitric acid.

The amines $ArNH_2$ are either known compounds or may be obtained by conventional procedures, for example by hydrogenation of the corresponding nitro derivatives using for example hydrogen in the presence of a metal catalyst in a suitable solvent, for example as more particularly described in the interconversion reactions discussed below. The nitrobenzenes for this particular reaction are either known compounds or may be prepared using similar methods to those used for the preparation of the known compounds.

Intermediate enaminones of formula (3) are either known compounds or may be prepared by reaction of an acetyl derivative $R^2COCH_2CN$ with an acetal $(R^{10})(R^{11})NCH(OR^{12})_2$ (where $R^{12}$ is a $C_{1-6}$alkyl group such as a methyl or ethyl group) at an elevated temperature. The starting materials for this reaction are either known compounds or may be prepared by methods analogous to those used for the preparation of the known compounds.

One particularly useful method for the preparation of acetyl derivatives $R^2COCH_2CN$ involves treating a corresponding isoxazole of formula (4):

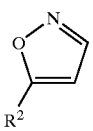

(4)

with a base such as an alkoxide, e.g. sodium ethoxide, in a solvent such as an alcohol, e.g. ethanol, at ambient temperature. Intermediate isoxazoles of formula (4) may be obtained by reaction of the corresponding aminopropenone $(R^2COCHCHN(R^{10})(R^{11}))$ with hydroxyl-amine in a solvent such as an alcohol, e.g. MeOH at ambient temperature. The aminopropenone starting material for this rection may be obtained by reaction of the corresponding methyl ketone $R^2COCH_3$ with an acetal $(R^{10})(R^{11})NCH(OR^{12})_2$ as described above.

In another process according to the invention, a compound of formula (1) may be prepared by displacement of a chlorine atom in a pyrimidine of formula (5):

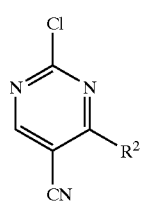

(5)

with an amine $ArNH_2$.

The reaction may be performed at an elevated temperature, for example the reflux temperature, where necessary in the presence of a solvent, for example an alcohol, such as 2-ethoxyethanol or isopopanol, a cyclic ether, e.g. dioxane or a substituted amide such as dimethylformamide, optionally in the presence of a base, for example an organic amine such as pyridine.

Intermediate pyrimidines of formula (5) may be obtained by reaction of a corresponding pyrimidine of formula (6):

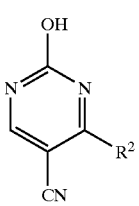

(6)

with phosphorous oxychloride optionally in a solvent such as a substituted amide e.g. dimethylformamide at an elevated temperature, for example the reflux temperature.

Intermediates of formula (6) may be prepared from the corresponding amine of formula (7):

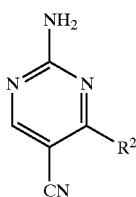

(7)

with sodium nitrite in an aqueous acid, e.g. aqueous sulphuric acid at around ambient temperature.

Amines of formula (7) may be prepared by reaction of an enaminone of formula (3) with a guanidine salt, e.g. guanidine carbonate, as described above for the preparation of compounds of formula (1).

Compounds of formula (1) may also be prepared by interconversion of other compounds of formula (1) and it is to be understood that the invention extends to such interconversion processes. Thus, for example, standard substitution approaches employing for example alkylation, arylation, heteroarylation, acylation, thioacylation, sulphonylation, formylation or coupling reactions may be used to add new substitutents to and/or extend existing substituents in compounds of formula (1). Alternatively existing substituents in compounds of formula (1) may be modified by for example oxidation, reduction or cleavage reactions to yield other compounds of formula (1).

The following describes in general terms a number of approaches which can be employed to modify existing Ar and/or $R^2$ groups in compounds of formula (1). It will be appreciated that each of these reactions will only be possible where an appropriate functional group exists in a compound of formula (1).

Where desired, these reactions may also be performed on intermediates to compounds of formula (1), for example in the preparation of intermediate amines, $ArNH_2$ or acetyl derivatives $R^2COCH_2CN$, and the description which follows is intended to apply to these intermediates even though only a compound of formula (1) is mentioned.

Thus, for example alkylation, arylation or heteroarylation of a compound of formula (1) may be achieved by reaction of the compound with a reagent AlkL or $Ar^3L$, where Alk is an alkyl group and $Ar^3$ is an aryl or heteroaryl group as defined above in relation to compounds of formula (1) and L is a leaving atom or group such as a halogen atom, e.g. a chlorine or bromine atom, or a sulphonyloxy group, e.g. an arylsulphonyloxy group such as a p-toluenesulphonyloxy group.

The alkylation, arylation or heteroarylation reaction may be carried out in the presence of a base, e.g. an inorganic base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran, at around 0° C. to around 40° C.

In a variation of this process the leaving group L may be alternatively part of the compound of formula (1) and the reaction performed with an appropriate nucleophilic reagent at an elevated temperature. Particular nucleophilic reagents include cyclic amines, such as piperazine or imidazole. Where appropriate the reaction may be performed in a solvent such as an aprotic solvent, e.g. a substituted amide such as dimethylformamide.

In another general example of an interconversion process, a compound of formula (1) may be acylated orthioacylated. The reaction may be performed for example with an acyl halide or anhydride in the presence of a base, such as a tertiary amine e.g. triethylamine in a solvent such as a halogenated hydrocarbon, e.g. dichloromethane or chloroform at for example ambient temperature, or by reaction with a thioester in an inert solvent such as tetrahydrofuran at a low temperature such as around 0° C. Alternatively, the reacton may be performed with an acid, in the presence of a condensing agent, for example a diimide such as 1-(3-dimethylaminopropyl)-3-ethylcarbodiimide, advantageously in the presence of a catalyst such as a N-hydroxy compound, e.g. a N-hydroxytriazole such as 1-hydroxybenzotriazole in the presence of a base, e.g. a cyclic amine such as N-methylmorpholine. The reaction is particularly suitable for use with compounds of formula (1) containing primary or secondary amino groups.

In a further general example of an interconversion process, a compound of formula (1) may be formylated, for example by reaction of the compound with a mixed anhydride $HCOOCOCH_3$ or with a mixture of formic acid and acetic anhydride.

Compounds of formula (1) may be prepared in another general interconversion reaction by sulphonylation, for example by reaction of the compound with a reagent $AlkS(O)_2L$, or $Ar^2S(O)_2L$ in the presence of a base, for example an inorganic base such as sodium hydride in a solvent such as an amide, e.g. a substituted amide such as dimethylformamide at for example ambient temperature. The reaction may in particular be performed with compounds of formula (1) possessing a primary or secondary amino group.

In further examples of interconversion reactions according to the invention compounds of formula (1) may be prepared from other compounds of formula (1) by modification of existing functional groups in the latter.

Thus in one example, ester groups $—CO_2Alk^1$ in compounds of formula (1) may be converted to the corresponding acid $[—CO_2H]$ by acid- or base-catalysed hydrolysis or by catalytic hydrogenation depending on the nature of the group $Alk^1$. Acid- or base-catalysed hydrolysis may be achieved for example by treatment with an organic or inorganic acid, e.g. TFA acid in an aqueous solvent or a mineral acid such as hydrochloric acid in a solvent such as dioxan or an alkali metal hydroxide, e.g. lithium hydroxide in an aqueous alcohol or ether e.g. aqueous MeOH or tetrahydrofuran. Catalytic hydrogenation may be carried out using for example hydrogen in the presence of a metal catalyst, for example palladium on a support such as carbon in a solvent such as an ether, e.g. tetrahydrofuran or an alcohol, e.g. MeOH.

In a second example, $—OAlk^2$ [where $Alk^2$ represents an alkyl group such as a methyl group] groups in compounds of formula (1) may be cleaved to the corresponding alcohol —OH by reaction with boron tribromide in a solvent such as a halogenated hydrocarbon, e.g. dichloromethane at a low temperature, e.g. around −78° C.

In another example, alcohol —OH groups in compounds of formula (1) may be converted to a corresponding —OAlk or —OAr group by coupling with a reagent AlkOH or ArOH in a solvent such as tetrahydrofuran in the presence of a phosphine, e.g. triphenylphosphine and an activator such as diethyl-, diisopropyl-, or dimethylazodicarboxylate.

Aminosulphonylamino $[—NHSO_2NH_2]$ groups in compounds of formula (1) may be obtained, in another example, by reaction of a corresponding amine $[—NH_2]$ with sulphamide in the presence of an organic base such as pyridine at an elevated temperature, e.g. the reflux temperature.

In another example of an interconversion process secondary amine groups in compounds of formula (1) may be alkylated using an alcohol, e.g. ethanol and catalytic hydrogenation, employing for example hydrogen in the presence of a metal catalyst such as palladium on a support such as carbon.

In a further example, amine [—$NH_2$] groups in compounds of formula (1) may be obtained by hydrolysis from a corresponding imide by reaction with hydrazine in a solvent such as an alcohol, e.g. ethanol at ambient temperature. In an alternative, amine groups may also be generated by reduction of the corresponding nitrile, for example using a reducing agent such as a borohydride, e.g. sodium borohydride or cerium trichloride. Alternatively, amine groups may be obtained by $Ce^{IV}$ oxidation of the corresponding p-anisyl- or p-anisylmethylamines using for example ceric ammonium nitrate in a solvent such as acetonitrile.

In another example cyclic amino groups in compounds of formula (1) may be prepared by cyclisation of a corresponding compound containing an amine [—$NH_2$] group with a reagent $L^1AlkL^2$ where $L^1$ and $L^2$ which may be the same or different is each a leaving atom or group as described above L and may for example each be a halogen atom such as a bromine atom. The reaction may advantageously be carried out in the presence of a base e.g. an inorganic base such as potassium carbonate, at an elevated temperature.

In another example, a nitro [—$NO_2$] group may be reduced to an amine [—$NH_2$], for example by catalytic hydrogenation as just described, or by chemical reduction using for example a metal, e.g. tin or iron, in the presence of an acid such as hydrochloric acid.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Where salts of compounds of formula (1) are desired, these may be prepared by conventional means, for example by reaction of a compound of formula (1) with an appropriate acid or base in a suitable solvent or mixture of solvents, e.g. an organic solvent such as an ether, e.g. diethylether, or an alcohol, e.g. ethanol.

The following Examples illustrate the invention. In the Examples all $^1$Hnmr were run at 300 MHz unless specified otherwise. All temperatures are in ° C.

The following abbreviations are used:
THF—tetrahydrofuran;
DMSO—dimethylsulphoxide;
DIBAL-H—diisobutylaluminium hydride;
DMF—dimethylformamide;
TFA—trifluoroacetic acid;
MeOH—methanol.

Intermediate 1

4-[2-(1,2,3-Triazol-1-yl)ethoxy]phenylguanidinium nitrate

The title compound was prepared from 4-[2-(1,2,3-triazol-1-yl)ethoxy]aniline (4.91 g, 24.07 mmol), cyanamide (1.56 g, 40.97 mmol) and concentrated $HNO_3$ (1.58 mL, 26.47 mmol) in a manner similar to the guanidine of Example 1 to give the desired material (4.7 g) as an off-white solid, m.p.>250°. δH ($d^6$DMSO) 9.33 (1H, s), 8.20 (1H, s), 7.74 (1H, s), 7.17–7.14 (6H, m), 7.00–6.97 (2H, m), 4.79 (2H, t, J 4.95 Hz) and 4.41 (2H, t, J 4.95 Hz).

4-[2-(1,2,3-Triazol-1-yl)ethoxy]aniline was prepared from 4-[2-(1,2,3-triazol-1-yl)ethoxy]nitrobenzene (5.98 g, 25.5 mmol) and 10% palladium on charcoal (1.5 g) in a manner similar to the aniline intermediate of Example 12 to give the desired material (4.91 g) as a yellow solid m.p. 141°. δH ($CDCl_3$) 7.69 (1H, d, J 0.5 Hz), 7.62 (1H, d J 0.5 Hz), 6.65 (2H, d, J 5.8 Hz), 6.58 (2H, d, J 5.8 Hz), 4.71 (2H, t, J 5.0 Hz), 4.24 (2H, t, J 5.0 Hz) and 3.43 (2H, s).

4-[2-(1,2,3-Triazol-1-yl)ethoxy]nitrobenzene was prepared from 4-[(2-p-toluenesulphonyloxy)ethoxy]nitrobenzene (10 g, 29.7 mmol) and 1,2,3-triazole, sodium salt (2.46 mmol) in a manner similar to the analogous reaction of Example 24 to give the desired material (2.25 g) as yellow solid, m.p. 123°. δH ($d^6$DMSO) 8.21 (1H, s), 8.20 (2H, d, J 2.3 Hz), 7.74 (1H, d, J 0.5 Hz), 7.14 (2H, d, J 2.4 Hz), 4.84 (2H, t, J 4.9 Hz) and 4.57 (2H, t, J 4.9 Hz). The reaction also yielded 4-[2-(1,2,3-triazol-2-yl)ethoxy]nitrobenzene (4.36 g) as a yellow solid, m.p. 111°. δH ($d^6$DMSO) 8.17 (2H, d, J 9.3 Hz), 7.80 (2H, s), 7.11 (2H, d, J 9.3 Hz), 4.86 (2H, t, J 4.8 Hz) and 4.64 (2H, t, J 4.8 Hz).

Intermediate 2

4-[2-(1,2,3-Triazol-2-yl)ethoxy]phenylguanidinium nitrate

The title compound was prepared from 4-[2-(1,2,3-triazol-2-yl)ethoxy]aniline (8.85 g, 43.4 mmol), cyanamide (2.82 g, 73.78 mmol) and concentrated HNO3 (1.58 mL, 26.47 mmol) in a manner similar to the guanidine of Example 1 to give the desired material (7.95 g) as an off-white solid, m.p.>250°. δH ($d^6$DMSO) 9.32 (1H, s), 7.80 (2H, s), 7.16–7.13 (6H, m), 7.00–6.97 (2H, m), 4.79 (2H, t, J 4.95 mmol) and 4.41 (2H, t, J 4.95 mmol).

4-[2-(1,2,3-Triazol-2-yl)ethoxy]aniline was prepared from 4-[2-(1,2,3-triazol-2-yl)ethoxy]nitrobenzene (10.5 g, 44.8 mmol) and 10% palladium on charcoal (1.5 g) in a manner similar to the aniline intermediate of Example 12 to give the desired material (4.91 g) as a yellow solid m.p. 159°. δH ($CDCl_3$) 7.62 (2H, s), 6.73–6.58 (4H, m), 4.77 (2H, t, J 5.8 Hz), 4.40 (2H, t, J 5.8 Hz) 3.43 (2H, s).

Intermediate 3

4-[2-(1,2,4-Triazol-1-yl)ethoxy]phenylguanidinium nitrate

The title compound was prepared from 4-[2-(1,2,4-triazol-1-yl)ethoxy]aniline (5.30 g, 25.9 mmol), cyanamide (1.86 g, 44.11 mmol) and concentrated $HNO_3$ (1.88 mL, 28.54 mmol) in a manner similar to the guanidine of Example 1 to give the desired material (6.62 g) as an off-white solid, m.p. 280–282°. δH ($d^6$DMSO) 9.33 (1H, bs), 8.56 (1H, s), 7.97 (1H, s), 7.17 (4H, bs), 7.16–7.12 (2H, s), 6.98–6.94 (2H, m), 4.58 (2H, t, J 5.0 Hz) and 4.34 (2H, t, J 2.0 Hz).

4-[12-(1,2,4-Triazol-1-yl)ethoxy]aniline was prepared from 4-[2-(1,2,4-triazol-1-yl)ethoxy]nitrobenzene (6.28 g, 26.8 mmol) and 10% palladium on charcoal (0.5 g) in a manner similar to the aniline intermediate of Example 12 to give the desired material (5.31 g) as a yellow solid m.p. 85–86°. δH ($CDCl_3$) 8.21 (1H, s), 7.94 (1H, s), 6.69–6.58 (4H, m), 4.51 (2H, t, J 5.0 Hz), 4.24 (2H, 5.2 Hz) and 3.45 (2H, bs).

4-[2-(1,2,4-Triazol-1-yl)ethoxy]nitrobenzene was prepared from 4-[(2-p-toluenesulphonyloxy)ethoxy]

nitrobenzene (10 g, 30.7 mmol) and 1,2,4-triazole, sodium salt (3.36 g, 36.8 mmol) in a manner similar to the analogous reaction of Example 24 to give the desired material (6.45 g) as yellow solid, m.p. 118–120°. δH (CDCl$_3$) 8.21–8.17 (3H, m), 7.97 (1H, s), 6.93–6.90 (2H, m), 4.62 (2H, t, J 5.2 Hz) and 4.45 (2H, t, J 5.3 Hz).

Intermediate 4

2-Cyano-3-dimethylamino-1-pyridin-3-ylpropen-1-one

2-Hydroxy-2-pyridin-3-ylacrylonitrile, sodium salt (1.0 g, 5.95 mmol) was dissolved in methanol (20 mL) and dimethylformamide diethylacetal (1.2 mL, 7.0 mmol) followed by 1M hydrochloric acid in diethyl ether (5.95 mL) were added. The reaction was stirred at room temperature for 1.5 h and then concentrated under reduced pressure. The resulting residue was subjected to column chromatography (silica 3% methanol in dichloromethane) to give the desired product (560 mg) as yellow solid. δH (CDCl3) 8.98 (1H, dd, J 2.3, 0.8 Hz), 8.69 (1H, dd, 4.8, 1.6 Hz), 8.08 (1H, dt, J 7.9, 2.2 Hz), 7.98 (1H, s), 7.37–7.33 (1H, m), 3.50 (3H, s) and (3H, s).

2-Hydroxy-2-pyridin-3-ylacrylonitrile was prepared by adding a solution of ethyl nicotinate (22.67 g, 0.15 mol) and acetonitrile (15.6 mol, 0.3 mol) in toluene (100 mL) and DMF (25 mL) to a suspension of sodium ethoxide (9.70 g, 0.143 mol) and the resulting mixture heated at reflux for 2 h with vigorous stirring. On cooling the reaction was diluted with ether (400 mL) and the resulting precipitate collected and washed further with ether to give the desired material (20.1 g) which was used without purification.

EXAMPLE 1

5-Cyano-4-phenyl-N-(3,4,5-trimethoxyphenyl)pyrimidine-2-amine

A mixture of 3,4,5-trimethoxyphenylguanidinium nitrate (1.44 g, 5.0 mmol), 1-phenyl-2-cyano-3-dimethylaminopropen-1-one (1.0 g, 5.0 mmol) and sodium hydroxide (0.22 g, 5.5 mmol) in ethanol (20 ml) was heated at reflux for 18 h. On cooling the resulting precipitate was collected by filtration, washed with water and diethyl ether, then dried to give the title compound (895 mg) as a green solid m.p. 246°. δH (d$^6$DMSO) 10.37 (1H, br s), 8.93 (1H, s), 7.99 (2H, m), 7.60 (3H, m), 7.25 (2H, m), 3.75 (6H, s) and 3.63 (3H, s).

The propenone used as starting material was prepared by refluxing benzoylacetonitrile (4.50 g, 31.0 mmol) in dimethylformamide diethylacetal (20 ml) for 12 h. On cooling the resulting solid was collected and washed with diethyl ether to give the desired product (4.50 g) as a beige solid m.p. 98°.

3,4,5-Trimethoxyphenylguanidinium nitrate was prepared by heating a solution of 3,4,5-trimethoxyaniline (5.49 g, 30.0 mmol), cyanamide [Aldrich, 50% solution in water w/v] (3.50 ml, 34.5 mmol) and concentrated HNO$_3$ (2.1 ml, 30.0 mmol) in ethanol (30 ml). The solid which formed on cooling to room temperature was collected by filtration, washed with ethanol and dried to give the desired material (4.60 g) as a grey solid m.p. 187°.

EXAMPLE 2

5-Cyano-N-[4-(2-hydroxyethyl)phenyl]-4-methoxycarbonylphenylpyrimidine-2-amine

In a similar manner to the compound of Example 1, from 4-(2-hydroxyethyl)phenylguanidinium nitrate (1.88 g, 7.75 mmol), 1-(4-methoxycarbonylphenyl)-2-cyano-3-dimethylaminopropen-1-one (2.07 g, 7.75 mmol) and sodium hydroxide (310 mg, 7.75 mmol)to give the title compound (2.40 g) as a yellow solid m.p. 194–196°. δH (d$^6$DMSO) 10.52 (1H, br s), 8.96 (1H, s), 8.15 (2H, d, J 8.2 Hz), 8.04 (2H, d, J 8.2 Hz), 7.63 (2H, d, J 7.9 Hz), 7.18 (2H, d, J 7.9 Hz), 4.61 (1H, t, J 5.1 Hz), 3.90 (3H, s), 3.57 (2H, m), and 2.68 (2H, d, J 7.0 Hz).

The propenone used as starting material in the above process was prepared in a similar manner to the analogous compound of Example 1, to give a yellow solid m.p. 118°.

4-(2-Hydroxyethyl)phenylguanidinium nitrate was prepared in a similar manner to the guanidine of Example 1 as an off-white solid.

EXAMPLE 3

5-Cyano-4-(4-methoxycarbonylphenyl)-N-(3,4,5-trimethoxyphenyl)pyrimidine-2-amine In a similar manner to the compound of Example 1, from 3,4,5-trimethoxyphenylguanidinium nitrate (1.12 g, 3.88 mmol), 2-cyano-1-(4-methoxycarbonylphenyl)-3-dimethylaminopropen-1-one (1.0 g, 3.9 mmol) and sodium hydroxide (258 mg, 3.88 mmol) to give the title compound (760 mg) as a yellow solid m.p. 206–208°. δH (d$^6$DMSO) 10.46 (1H, s), 8.97 (1H, s), 8.15 (4H, m), 7.23 (2H, br s), 3.89 (3H, s), 3.74 (6H, s) and 3.62 (3H, s).

EXAMPLE 4

5-Cyano-N-[4-(2-imidazol-1-ylethyl)phenyl]-4-(4-methoxcarbonylphenyl)pyrimidine-2-amine To a solution of the compound of Example 2 (750 mg, 2.0 mmol) in pyridine (10 ml) was added 4-toluenesulphonyl chloride (458 mg, 2.0 mmol) and the mixture stirred at ambient temperature for 2.5 h. The reaction was diluted with dichloromethane (50 ml), washed with 1M hydrochloric acid (2×50 ml) followed by saturated Na$_2$CO$_3$ (1×25 ml), dried (MgSO$_4$) and then concentrated under reduced pressure. The residue was subjected to column chromatography (silica gel; 5% methanol-dichloromethane) to give the desired tosylate (600 mg) as a yellow solid. This material was dissolved in dry DMF (15 ml) containing imidazole (272 mg, 4.0 mmol) and the resulting mixture was stirred under a nitrogen atmosphere at 80° for 6 h. To the reaction was added saturated brine (150 ml) and 2M NaOH (10 ml) and this was extracted with dichloromethane (1×100 ml). The organic phase was dried (MgSO$_4$) and concentrated under reduced pressure. The residue was recrystallised from ethyl acetate/propan-2-ol (10:1) to give the title compound (185 mg) as a pale yellow solid m.p. 216–218°. δH (d$^6$DMSO) 10.55 (1H, br s), 8.97 (1H, s), 8.15 (2H, d, J 8.0 Hz), 8.04 (2H, d, J 8.0 Hz), 7.64 (2H, d, J 6.9 Hz), 7.48 (1H, s), 7.13 (3H, br s), 6.83 (1H, s), 4.18 (2H, m), 3.90 (3H, s), and 3.30 (2H, m).

EXAMPLE 5

5-Cyano-4-(4-hydroxymethylphenyl)-N-(3,4,5-trimethoxyphenyl)pyrimidine-2-amine

To a solution of the compound of Example 3 (210 mg, 0.5 mmol) in dry THF (20 ml) at 0°, under a nitrogen atmosphere, was added DIBAL-H (1M in THF) (2.5 ml, 2.5 mmol) and the reaction was allowed to warm to ambient temperature over 4.5 h. The reaction was quenched with 1M potassium-sodium tartrate (75 ml) and extracted with ethyl acetate (2×75 ml). The organic phase was dried (MgSO$_4$), concentrated under reduced pressure and the residue subjected to column chromatography (silica gel; 3% methanol-dichloromethane) to give the title compound (150 mg) as a yellow solid m.p.188–191°. δH (d$^6$DMSO) 10.46 (1H, br s), 8.92 (1H, s), 7.99 (2H, br m), 7.54(2H, d, J 8.0 Hz), 7.23 (2H, br s), 5.37 (2H, t, J 4.1 Hz), 4.58 (2H, d, J 4.1 Hz), 3.73 (6H, s) and 3.53 (3H, s).

EXAMPLE 6

5-Cyano-4-[(4-N,N-diethylaminomethyl)phenyl]-N-(3,4,5-trimethoxy-phenyl)pyrimidine-2-amine The compound of Example 5 was dissolved in chloroform (10 mL), thionyl chloride (37 μl) added and the resulting solution heated at reflux for 0.1 h. The reaction was concentrated under reduced pressure and the residue taken up in acetonitrile (6 ml) to which N,N-diethylamine (150 μl) was added. After heating at reflux for 5 h the mixture was concentrated under reduced pressure and the residue was subjected to column chromatography (silica gel; 5% methanol-dichloromethane) to give the title compound as a yellow solid m.p. 137°. δH (d$^6$DMSO) 8.68 (1H, s), 8.05 (2H, d, J 8.0 Hz), 7.55–7.51 (3H, m), 7.00 (2H, br s), 3.88 (6H, s), 3.85 (3H, s), 2.56 (4H, q, J 7.1 Hz) and 1.07 (6H, t, J 7.1 Hz).

EXAMPLE 7

5-Cyano-4-[2-(3-(R)-dimethylaminopyrrolidin-1-yl) pyridin-5-yl]-N-(indazol-5-yl)pyrimidine-2-amine 4-(2-Chloropyridin-5-yl)-5-cyano-N-(indazol-5-yl) pyrimidine-2-amine (522 mg, 1.5 mmol) and 3-(R)-dimethylaminopyrrolidine were heated together at 140° in a sealed flask for 2 h. On cooling the reaction mixture was triturated with water to give a brown solid which was collected and subjected to column chromatography (silica gel; 1% triethylamine-10% methanol-89% dichloromethane) to give the title compound (417 mg) as a yellow solid m.p.249–250°. δH (d$^6$DMSO) 13.00 (1H, br s), 10.32 (1H, s), 8.81 (2H, d, J 9.2 Hz), 8.15–8.12 (2H, m), 8.04 (1H, s), 7.59 (1H, m), 7.52 (1H, d, J 9.8 Hz), 6.63 (1H, d, J 9.0 Hz), 3.77–3.67 (2H, m), 3.41–3.24 (2H, m), 2.82 (1H, br m), 2.22 (6H, s), 2.21 (1H, m) and 1.84 (1H, m).

The chloropyridine used as starting material was prepared from indazol-5-ylguanidinium nitrate (1.51 g, 6.36 mmol), 1-(2-chloropyridin-5-yl)-2-cyano-3-dimethylaminopropen-1-one (1.50 g, 6.36 mmol) and sodium hydroxide (254 mg, 6.36 mmol) to give the desired product (1.49 g) as a white solid m.p.>285° (decomp).

The propenone was prepared from 3-(2-chloropyridin-5-yl)-3-oxopropio-nitrile (4.2 g, 23.3 mmol) and dimethylformamide diethylacetal (13 ml) to give the desired material (5.05 g) as an off-white solid m.p. 130–132°.

3-(2-Chloropyridin-5-yl)-3-oxopropionitrile was prepared by treating a solution of cyanoacetic acid (9.10 g, 53.5 mmol) and 2,2'-bipyridyl (5 mg) in dry THF (500 ml), cooled to –70° under a nitrogen atmosphere, dropwise with n-butyllithium (85.6 ml, 214 mmol of a 2.5M solution in hexane). The reaction was allowed to warm to 0° over a period of 1 h and then recooled to –70°, at which point a solution of 6-chloronicotinyl chloride (9.42 g, 53.5 mmol) in THF (75 ml) was added to the resulting red slurry. The reaction was stirred at –70° for a further 1 h upon complete addition, and then allowed to reach 0° where upon 2M hydrochloric acid (250 ml) was added. The reaction was extracted with chloroform (2×400 ml) and the combined organic phases were then washed with saturated aqueous NaHCO$_3$ (1×250 ml) and saturated brine (1×250 ml), dried (MgSO$_4$) and concentrated under reduced pressure. The resulting solid was triturated with diethyl ether/n-hexane (1:5) to give the desired material (4.20 g) as a pale yellow powder m.p. 122–123°.

Indazol-5-ylguanidinium nitrate was prepared from 5-aminoindazole (4.0 g, mmol), cyanamide (1.89 g, 45.1 mmol) and concentrated HNO$_3$ (2.8 ml) to give the desired material as a solid m.p. 252–254°.

EXAMPLE 8

4-[4-(1-Amino-1-methylethyl)phenyl]-5-cyano-N-(indazol-5-yl)pyrimidine-2-amine

A mixture of indazol-5-ylguanidinium nitrate (524 mg, 2.2 mmol), 1-[4-(1-tert-butoxycarbonylamino-1-methylethyl)phenyl]-2-cyano-3-dimethylaminopropen-1-one (714 mg, 2.0 mmol) and powdered sodium hydroxide (96 mg, 2.4 mmol) in propan-2-ol (30 ml) was heated at reflux for 6 h. The reaction was concentrated in vacuo and the residue purified by column chromatography (silica, 60% ethyl acetate in hexane, loading the crude material in dichloromethane) to give 4-[4-(1-tert-butoxycarbonylamino-1-methylethyl)phenyl]-5-cyano-N-(indazol-5-yl)-pyrimidine-2-amine as a yellow solid (850 mg). δH (CDCl$_3$) 8.69 (1H, s), 8.18 (1H, s), 8.11 (1H, s), 8.05 (2H, d, J 8.4 Hz), 7.93 (1H, bs), 7.57 (2H, d, J 8.4 Hz), 7.50 (2H, m), 5.10 (1H, bs), 1.66 (6H, s), 1.40 (9H, bs). MS (ESI) 492 (MNa+, 61%), 470 (MH+, 100%), 414 (19%). This product was dissolved in a mixture of TFA acid (20 ml) and CH$_2$Cl$_2$ (20 ml) and was stirred for 30 mins at room temperature before concentrating the reaction in vacuo. The residue was dissolved in 10% MeOH in CH$_2$Cl$_2$ (200 ml) and the organic phase washed with sat. Na$_2$CO$_3$ (aq) (50 ml), dried (MgSO$_4$) and concentrated in vacuo to give the title compound as a bright yellow solid (541 mg) m.p. 267–271° (dec.). δH (d$^6$DMSO) 13.03 (1H, bs), 10.46 (1H, s), 8.91 (1H, s), 8.16 (1H, s), 8.04 (1H, s), 7.94 (2H, d, J 8.4 Hz), 7.74 (2H, d, J 8.4 Hz), 7.61 (1H, m), 7.52 (1H, d, J 8.9 Hz), 3.44 (2H, bs), 1.48 (6H, s). MS (ESI) 392 (MNa+, 11%), 370 (MH+, 23%), 353 (100%).

The 1-[4-(1-tert-butoxycarbonylamino-1-methylethyl) phenyl]-2-cyano-3-dimethyl-aminopropen-1-one used in the above process was prepared as follows:

A mixture of 4-acetylbenzonitrile (51.84 g, 0.357 mol) and N,N-dimethylformamide dimethyl acetal (142 ml, 1.07 mol) was heated to reflux for 1.5 h. The reaction was cooled to room temperature and the resultant crystalline mass collected by filtration and washed with diethyl ether (4×100 ml) to give 1-(4-cyanophenyl)-3-dimethylaminopropen-1-one as an orange solid (44.56 g). An additional crop of this product (11.40 g) could be obtained by partially concentrating the filtrate. δH (d$^6$DMSO) 8.01 (2H, d, J 8.2 Hz), 7.87 (2H, d, J 8.2 Hz), 7.75 (1H, d, J 12.2 Hz), 5.83 (1H, d, J 12.2 Hz), 3.15 (3H, bs), 2.92 (3H, bs). MS (ESI) 201 (MH+, 100%).

Hydroxylamine hydrochloride (21.40 g, 308 mmol) was added to a suspension of 1-(4-cyanophenyl)-3-dimethylaminopropen-1-one (55.96 g, 280 mmol) in MeOH (450 ml) and the reaction stirred at room temperature for 24 h. The reaction was diluted with water (400 ml) and the resultant precipitate collected by filtration, washed with water (5×150 ml) and dried in vacuo to give 4-(5-isoxazolyl)-benzonitrile as a pale yellow solid (42.53 g) m.p.

148–149°. δH (CDCl$_3$) 8.35 (1H, d, J 1.8 Hz), 7.91 (2H, d, J 8.3 Hz), 7.77, (2H, d, J 8.3 Hz), 6.66 (1H, d, J 1.8 Hz).

Cerium trichloride heptahydrate (112.6 g, 302 mmol) was dried under vacuum (0.6 mbar) at 140–150° (oil bath) for 4 h in a flask fitted with a large magnetic stirring bar. The flask was refilled with nitrogen, cooled to 0° with an ice bath and anhydrous THF (500 ml) introduced with stirring. On complete addition the ice bath was removed and the milky suspension stirred at room temperature for 16 h. The reaction was cooled to −78° and methyl lithium (188 ml of a 1.6M solution in diethyl ether, 300 mmol) added dropwise with stirring. After 45 mins a solution of 4-(5-isoxazolyl)-benzonitrile (17.0 g, 100 mmol) in anhydrous THF (100 ml) was added and the reaction mixture left to warm in the cooling bath from −78° to −10° over 3 h. The reaction was quenched with 33% ammonium hydroxide (250 ml) and filtered through a pad of Celite® to remove the resultant solids. The Celite® pad was washed thoroughly with ethyl acetate (4×100 ml) and the combined filtrates concentrated to approximately 200 ml. These filtrates were diluted with brine (200 ml) and extracted with ethyl acetate (2×150 ml), the organic extracts were dried (MgSO$_4$) and concentrated in vacuo to give 1-[4-(5-isoxazolyl)phenyl]-1-methylethylamine as a yellow solid (19.53 g). δH (CDCl$_3$) 8.27 (1H, d, J 1.9 Hz), 7.76 (2H, dt, J 8.7, 2.0 Hz), 7.62 (2H, d, dt, J 8.7, 2.0 Hz), 6.49 (1H, d, J 1.9 Hz), 1.94 (2H, bs), 1.53 (6H, s). This compound was used in the following step without purification. A mixture of 1-[4-(5-isoxazolyl) phenyl]-1-methylethylamine (23.87 g, 118.2 mmol) and di-tert-butyl dicarbonate (28.37 g, 130 mmol) in toluene (200 ml) was heated to reflux for 1 h before removing solvent in vacuo. The resultant solid was recrystallised from ethanol to give tert-butyl N-{1-[4-(5-isoxazolyl)phenyl]-1-methylethyl}carbamate as bright yellow crystals (24.90 g) m.p. 145–146°. δH (CDCl$_3$) 8.27 (1H, d, J 1.8 Hz), 7.75 (2H, d t, J 8.7, 2.1 Hz), 7.50 (2H, d t, J 8.7, 2.1 Hz), 6.49 (1H, d, J 1.8 Hz), 4.97 (1H, bs), 1.64 (6H, s), 1.37 (9H, bs). MS (ESI) 325 (MNa+, 42%), 303 (MH+, 56%), 186 (100%).

A freshly prepared solution of sodium ethoxide (3.77 g, 164 mmol of sodium in 150 ml of ethanol) was added to a suspension of tert-butyl N-{1-[4-(5-isoxazolyl)phenyl]-1-methylethyl}carbamate (24.76 g, 82 mmol) in ethanol (150 ml) and the reaction stirred at room temperature for 1 h. Ethanol was removed in vacuo and the residue partitioned between ethyl acetate (150 ml) and cold 1M hydrochloric acid (250 ml). The aqueous layer was re-extracted with ethyl acetate (2×80 ml) and the combined ethyl acetate extracts washed with brine (100 ml), dried (MgSO$_4$) and concentrated in vacuo to give tert-butyl N-{1-[4-(2-cyanoacetyl) phenyl]-1-methylethyl} carbamate as an off-white solid m.p.122–123°. This crude product was dissolved in THF (150 ml), N,N-dimethylformamide diethyl acetal (14.48 g, 98.4 mmol) added and the mixture heated to 50° for 1 h. Solvent was removed in vacuo and the residue purified by column chromatography (silica, 2–4% MeOH in CH$_2$Cl$_2$) to give 1-[4-(1-tert-butoxycarbonyl-amino-1-methylethyl) phenyl]-2-cyano-3-dimethylaminopropen-1-one as a pale yellow solid (24.46 g) m.p. 160–162°. δH (CDCl$_3$) 7.94 (1H, s), 7.77 (2H, dt, J 8.6, 1.9 Hz), 7.45 (2H, dt, J 8.6, 1.9 Hz), 5.08 (1H, bs), 3.48 (3H, s), 3.28 (3H, s), 1.63 (6H, s), 1.32 (9H, bs). MS (ESI) 380 (MNa+, 63%), 358 (MH+, 32%), 302 (96%), 241 (100%).

EXAMPLE 9

4-[4-(1-Amino-1-methylethyl)phenyl]-5-cyano-N-(3, 4,5-trimethoxyphenyl)pyrimidine-2-amine The title compound was prepared from 3,4,5-trimethoxyphenylguanidinium nitrate (576 mg, 2.0 mmol), 1-[4-(1-tert-butoxycarbonylamino-1-methylethyl)phenyl]-2-cyano-3-dimethylaminopropen-1-one (660 mg, 1.8 mmol) and powdered sodium hydroxide (89 mg, 2.2 mmol) following the method described for the compound of Example 8. This gave the intermediate 4-[4-(1-tert-butoxycabonylamino-1methylethyl)phenyl]-5-cyano-N-(3, 4,5-trimethoxyphenyl)pyrimidine-2-amine as a yellow solid (769 mg) after column chromatography (silica, 40% ethyl acetate in hexane). This compound was treated with TFA acid in CH$_2$Cl$_2$ as descibed for the analogous compound of Example 8 to give the title compound as a pale yellow solid (597 mg) m.p. 167–168°. δH (d$^6$ DMSO) 10.34 (1H, bs), 8.90 (1H, s), 7.96 (2H, bd, J 7.8 Hz), 7.73 (2H, d, J 8.2 Hz), 7.24 (2H, bs), 3.76 (6H, s), 3.63 (3H, s), 3.18 (2H, bs), 1.42 (6H, s). MS (ESI) 442 (MNa+, 16%), 420 (MH+, 57%), 403 (100%).

Except where otherwise indicated, the following compounds of Examples 10–23 and their respective intermediates were prepared in a manner to the compound of Example 8 and its intermediates:

EXAMPLE 10

4-[4-(1-Amino-1-methylethyl)phenyl]-5-cyano-N-[(4-imidazol-1-yl)phenyl]pyrimidine-2-amine From 4-(imidazol-1-yl)phenylguanidinium nitrate (916 mg, 2.8 mmol), 1-[4-(1-tert-butoxycarbonylamino-1-methylethyl)phenyl]-2-cyano-3-dimethylaminopropenone (1.0 g, 2.8 mmol) and powdered sodium hydroxide (224 mg, 3.6 mmol) to give 4-[4-(1-tert-butoxycarbonylamino-1-methylethyl)phenyl]-5-cyano-N[(4-imidazol-1-yl)phenyl] pyrimidine-2-amine as a yellow solid (675 mg) after column chromatography (silica, 2% MeOH in dichloromethane). This compound was treated with TFA acid in CH$_2$Cl$_2$ as described for Example 8 to give the title compound as a pale yellow solid (471 mg) m.p. 232–233°. δH (d$^6$ DMSO) 10.51 (1H, bs), 8.95 (1H, s), 8.19 (1H, s), 7.93–7.89 (4H, m), 7.76–7.61 (5H, m), 7.08 (1H, s), 2.20 (2H, bs) and 1.41 (6H, s).

EXAMPLE 11

4-[4-(1-Amino-1-methylethyl)phenyl]-5-cyano-N-[4-(1,2,4-triazol-1-yl)phenyl]pyrimidine-2-amine From 4-(1,2,4-triazol-1-yl)phenylguanidinium nitrate (750 mg, 2.8 mmol), 1-[4-(1-tert-butoxycarbonylamino-1-methylethyl)phenyl]-2-cyano-3-dimethyl-aminopropenone (1.0 g, 2.8 mmol) and powdered sodium hydroxide (150 mg, 3.75 mmol) to give 4-[4-(1-tert-butoxycarbonylamino-1-methylethyl)phenyl]-5-cyano-N[4-(1,2,4-triazol-1-yl) phenyl]pyrimidine-2-amine as a yellow solid (380 mg) after column chromatography (silica, 2% MeOH in dichloromethane). This compound was treated with TFA acid in CH$_2$Cl$_2$ as described for Example 8 to give the title compound as a pale yellow solid (224 mg) m.p. 208–209°. δH (d$^6$ DMSO) 10.67 (1H, bs), 9.21 (1H, s), 8.97 (1H, s), 8.20 (1H, s), 7.97–7.94 (4H, m), 7.82 (2H, d, J 9.1 Hz), 7.76 (2H, d, J 8.9 Hz), 2.09 (2H, bs) and 1.41 (6H, s).

The guanidine used as starting material in the above process was prepared from 4-(1,2,4-triazol-1yl)aniline (1.60 g, 10.0 mmol). cyanimide (715 mg, 17 mmol) and concentrated HNO$_3$ (725 mL, 11 mmol), in a manner similar to the corresponding starting material of Example 1, as a beige solid (1.50 g) m.p.>310°(decomp). 4-(1,2,4-triazol-1yl) aniline was prepared by suspending 4-(1,2,4-triazol-1-yl) nitobenzene (2.25 g, 11.83 mmol) with 10% palladium on charcoal in ethanol (125 ml), containing 4M hydrochloric acid (75 mL). The resulting mixture was stirred under a hydrogen atmosphere at normal pressure and room temperature for 16 h. The reaction was filtered through a pad of Celite® washing thoroughly with ethanol. The filtrate was concentrated to 50 mL in volume and 2M NaOH added until the pH was >10. The solution was again concentrated to 50 mL and cooled to 00. The resulting solid was collected by filtration and washed sparingly with water to give the desired material (1.65 g) as an off-white solid, m.p. 150–152°.

The nitrobenzene used in the above process was prepared by heating a mixture of 4-fluornitrobenzene (40 g, 28.3 mmol) and 1,2,4-triazole, sodium salt (28.4 g, 31.2 mmol) in DMF (250 mL) at 80° for 4 h. On cooling the reaction was poured into cooled saturated brine (600 mL) and 2M NaOH (400 mL). The resulting solid was collected by filtration, washed with 2M NaOH (2×150 mL), water (3×100 mL) then ethanol (2×75 mL) and dried under high vacuum. The product was purified by column chromatography (silica 3% MeOH in dichloromethane) to give the desired material as a yellow solid (9.05 g).

EXAMPLE 12

4-[4-(1-Amino-1-methylethyl)phenyl]-5-cyano-N-[4-(1,2,3-triazol-1-yl)phenyl]pyrimidine-2-amine From 4-(1,2,3-triazol-1-yl)phenylguanidinium nitrate (750 mg, 2.8 mmol), 1-[4-(1-tert-butoxycarbonylamino-1-methylethyl)phenyl]-2-cyano-3-dimethylaminopropenone (1.0 g, 2.8 mmol) and powdered sodium hydroxide (150 mg, 3.75 mmol) to give 4-[4-(1-tert-butoxycarbonylamino-1-methylethyl)phenyl]-5-cyano-N[4-(1,2,4-triazol-1-yl) phenyl]pyrimidine-2-amine as a yellow solid (380 mg) after column chromatography (silica, 2% MeOH in dichloromethane). This compound was treated with TFA acid in $CH_2Cl_2$ as described for Example 8 to give the title compound as a pale yellow solid (224 mg) m.p. 208–209°. δH ($d^6$ DMSO) 10.67 (1H, bs), 9.21 (1H, s), 8.97 (1H, s), 8.20 (1H, s), 7.97–7.94 (4H, m), 7.82 (2H, d, J 9.1 Hz), 7.76 (2H, d, J 8.9 Hz), 2.09 (2H, bs) and 1.41 (6H, s).

4-(1,2,3-triazol-1-yl)phenylguanidinium nitrate was prepared from 4-(1,2,3-triazol-1-yl)aniline (1.42 g, 8.87 mmol), cyanamide (635 mg, 15.1 mmol) and concentrated $HNO_3$ (645 ml, 9.67 mmol) in a manner similar to the corresponding starting material of Example 1, as a white solid (1.0 g), m.p.>320°.

The aniline used in the above process was prepared by hydrogenation of 4-(1,2,3-triazol-1-yl)nitrobenzene (1.86 g, 9.78 mmol) in ethanol (75 mL) over 10% palladium on charcoal (500 mg) at atmospheric pressure and room temperature for 20 h. The catalyst was removed by filtration through Celite® and the filtrate concentrated to give the desired product as an off-white solid (1.43 g), m.p. 139–140°.

EXAMPLE 13

4-[4-(1-Amino-1-methylethyl)phenyl]-5-cyano-N-(3,5-difluorophenyl)pyrimidine-2-amine From 3,5-difluorophenylguanidinium nitrate (983 mg, 2 mmol), 1-[4-(1-tert-butoxycarbonylamino-1-methylethyl) phenyl]-2-cyano-3-dimethylaminopropenone (1.5 g, 4.2 mmol) and powdered sodium hydroxide (176 mg, 4.3 mmol) to give 4-[4-(1-tert-butoxycarbonylamino-1-methylethyl) phenyl]-5-cyano-N-[3,5-difluorophenyl]pyrimidine-2-amine as a yellow solid (510 mg) after column chromatography (silica, 2% MeOH in dichloro-methane). This compound was treated with TFA acid in $CH_2Cl_2$ as described for Example 8 to give the title compound as a pale yellow solid (332 mg) m.p. 209°. δH ($d^6$ DMSO) 9.06 (1H, s), 8.00 (2H, d, J 8.5 Hz), 7.78 (2H, d, J 8.5 Hz), 7.62–7.54 (2H, m), 6.93–6.86 (1H, m) and 1.60 (6H, s).

EXAMPLE 14

4-[4-(1-Amino-1-methylethyl)phenyl]-5-cyano-N-(3-fluoro-4-methylphenyl)pyrimidine-2-amine From 3-fluoro-4-methylphenylguanidinium nitrate (1.15 g, 5.0 mmol), 1-[4-(1-tert-butoxycarbonylamino-1-methylethyl)phenyl]-2-cyano-3-dimethylaminopropenone (1.78 g, 4.98 mmol) and powdered sodium hydroxide (176 mg, 4.2 mmol) to give 4-[4-(1-tert-butoxycarbonylamino-1-methylethyl)phenyl]-5-cyano-N-[3-fluoro-4-methylphenyl] pyrimidine-2-amine as a yellow solid (1.47 g) after column chromatography (silica, 2% MeOH in dichloromethane). This compound was treated with TFA acid in $CH_2Cl_2$ as described for Example 8 to give the title compound as a pale yellow solid (1.16) m.p. 209°. δH ($d^6$ DMSO) 8.96 (1H, s), 7.91 (2H, d, J 8.5 Hz), 7.76 (2H, d, J 8.5 Hz), 7.70 (1H, m), 7.46–7.43 (1H, m), 7.27–7.21 (1H, m) and 1.60 (6H, s).

EXAMPLE 15

4-[4-(1-Amino-1-methylethyl)phenyl]-5-cyano-N-(3,4,5-trifluorophenyl)pyrimidine-2-amine From 3,4,5-trifluorophenylguanidinium nitrate (1.06 g, 4.2 mmol), 1-[4-(1-tert-butoxycarbonylamino-1-methylethyl)phenyl]-2-cyano-3-dimethylaminopropenone (1.5 g, 4.2 mmol) and powdered sodium hydroxide (176 mg, 4.2 mmol) to give 4-[4-(1-tert-butoxycarbonylamino-1-methylethyl)phenyl]-5-cyano-N-[3,4,5-trifluoro-phenyl] pyrimidine-2-amine as a yellow solid (597 mg) after column chromatography (silica, 2% MeOH in dichloro-methane). This compound was treated with TFA acid in $CH_2Cl_2$ as described for Example 8 to give the title compound as a pale yellow solid (401 mg) m.p. 220°. δH ($d^6$ DMSO) 9.01(1H, s), 7.91 (2H, m), 7.78–7.71 (4H, m) and 1.40 (6H, s).

EXAMPLE 16

4-[4-(1-Amino-1-methylethyl)phenyl]-5-cyano-N-4-fluoro-3-trifluoromethylphenyl)pyrimidine-2-amine From 4-fluoro-3-trifluoromethylphenylguanidinium nitrate (1.19 g, 4.2 mmol), 1-[4-(1-tert-butoxycarbonylamino-1-methylethyl)phenyl]-2-cyano-3-dimethylamino-propenone (1.5 g, 4.2 mmol) and powdered sodium hydroxide (176 mg, 4.2 mmol) to give 4-[4-(1-tert-butoxycarbonylamino-1-methylethyl)phenyl]-5cyano-N-[4-fluoro-3-trifluoromethylphenyl]pyrimidine-2-amine as a yellow solid (648 mg) after column chromatography (silica, 2% MeOH in dichloromethane). This compound (211 mg) was treated with TFA acid in $CH_2Cl_2$ as described for Example 8 to give the title compound as a pale yellow solid (157 mg) m.p. 181°. δH ($d^6$ DMSO) 8.91 (1H, s), 8.32 (1H, dd, J 6.5, 2.6 Hz), 8.06–8.00 (1H, s), 7.99 (2H, d, J 8.8 Hz), 7.77 (2H, d, J 8.8 Hz), 7.44 (1H, m) and 1.47 (6H, s).

EXAMPLE 17

4-[4-(1-Amino-1-methylethyl)phenyl]-5-cyano-N-(2,4-difluorophenyl)pyrimidine-2-amine From 2,4-difluorophenylguanidinium nitrate (0.98 g, 4.2 mmol), 1-[4-(1-tert-butoxycarbonylamino-1-methylethyl)

phenyl]-2-cyano-3-dimethylaminopropenone (1.5 g, 4.2 mmol) and powdered sodium hydroxide (176 mg, 4.3 mmol) to give 4-[4-(1-tert-butoxycarbonylamino-1-methylethyl)phenyl]-5-cyano-N-[2,4,-difluoro-phenyl]pyrimidine-2-amine as a yellow solid (648 mg) after column chromatography (silica, 2% MeOH in dichloromethane). This compound was treated with TFA acid in $CH_2Cl_2$ as described for Example 8 to give the title compound as a pale yellow solid (460 mg) m.p. 203°. $\delta H$ ($d^6$ DMSO) 8.65 (1H, s), 7.82 (2H, d, J 6.6 Hz), 7.70 (2H, d, J 8.3 Hz), 7.61–7.55 (1H, m), 7.38–7.32 (1H, m), 7.14–7.09 (1H, m) and 1.39 (6H, s).

EXAMPLE 18

4-[4-(1-Amino-1-methylethyl)phenyl]-5-cyano-N-(3,4-difluorophenyl)pyrimidine-2-amine From 3,4-difluorophenylguanidinium nitrate (0.98 g, 4.2 mmol), 1-[4-(1-tert-butoxycarbonylamino-1-methylethyl)phenyl]-2-cyano-3-dimethylaminopropenone (1.5 g, 4.2 mmol) and powdered sodium hydroxide (176 mg, 4.3 mmol) to give 4-[4-(1-tert-butoxycarbonylamino-1-methylethyl)phenyl]-5-cyano-N-[3,4-difluorophenyl]pyrimidine-2-amine as a yellow solid (631 mg) after column chromatography (silica, 2% MeOH in dichloromethane). This compound was treated with TFA acid in $CH_2Cl_2$ as described for Example 8 to give the title compound as a pale yellow solid (412 mg) m.p. 192°. $\delta H$ ($d^6$ DMSO) 10.66 (1H, bs), 8.97 (1H, s), 7.99–7.92 (1H, m), 7.90 (2H, d, J 8.5 hz), 7.76 (2H, d, J 8.5 hz), 7.53–7.38 (2H, m) and 1.41 (6H, s).

EXAMPLE 19

4-[4-(1-Amino-1-methylethyl)phenyl]-5-cyano-N-(3-chloro-4-fluorophenyl)pyrimidine-2-amine From 3-chloro-4-fluorophenylguanidinium nitrate (1.05 g, 4.2 mmol), 1-[4-(1-tert-butoxycarbonylamino-1-methylethyl)phenyl]-2-cyano-3-dimethylaminopropenone (1.5 g, 4.2 mmol) and powdered sodium hydroxide (176 mg, 4.3 mmol) to give 4-[4-(1-tert-butoxycarbonylamino-1-methylethyl)phenyl]-5-cyano-N-[3-chloro-4-fluorophenyl]pyrimidine-2-amine as a yellow solid (895 mg) after column chromatography (silica, 2% MeOH in dichloromethane). This compound was treated with TFA acid in $CH_2Cl_2$ as described for Example 8 to give the title compound as a pale yellow solid (501 mg) m.p. 237°. $\delta H$ ($d^6$DMSO) 10.60 (1H, bs), 8.97 (1H, s), 8.07 (1H, d, J 6.8, 2.5 Hz), 7.91 (2H, dapp, J 8.5 Hz), 7.75 (2H, d, J 8.5 Hz), 7.73–7.69 (1H, m), 7.41 (1H, tapp, J 9.1 Hz) and 1.41 (6H, s).

EXAMPLE 20

4-[4-(1-Amino-1-methylethyl)phenyl]-5-cyano-N-(4-fluorophenyl)pyrimidine-2-amine From 4-fluorophenylguanidinium nitrate (0.91 g, 4.2 mmol), 1-[4-(1-tert-butoxycarbonylamino-1-methylethyl)phenyl]-2-cyano-3-dimethylaminopropenone (1.5 g, 4.2 mmol) and powdered sodium hydroxide (176 mg, 4.3 mmol) to give 4-[4-(1-tert-butoxycarbonylamino-1-methylethyl)phenyl]-5-cyano-N-[4-fluorophenyl]pyrimidine-2-amine as a yellow solid (1.28 g) after column chromatography (silica, 2% MeOH in dichloromethane). This compound was treated with TFA acid in $CH_2Cl_2$ as described for Example 8 to give the title compound as a pale yellow solid (607 mg) m.p. 228–229°. $\delta H$ ($d^6$ DMSO) 10.59 (1H, s), 9.02 (1H, s), 8.00 (2H, d, J 8.4 Hz), 7.86–7.83 (4m), 7.32–7.27 (2H, m) and 1.51 (6H, s).

EXAMPLE 21

4-[4-(1-Amino-1-methylethyl)phenyl]-5-cyano-N-(3-trifluoromethylphenyl)pyrimidine-2-amine From 3-trifluoromethylphenylguanidinium nitrate (1.12 g, 4.2 mmol), 1-[4-(1-tert-butoxycarbonylamino-1-methylethyl)phenyl]-2-cyano-3-dimethylaminopropenone (1.5 g, 4.2 mmol) and powdered sodium hydroxide (176 mg, 4.3 mmol) to give 4-[4-(1-tert-butoxycarbonylamino-1-methylethyl)phenyl]-5-cyano-N-[3-trifluoromethyl]pyrimidine-2-amine as a yellow solid (1.32 g) after column chromatography (silica, 2% MeOH in dichloromethane). This compound was treated with TFA in $CH_2Cl_2$ as described for Example 8 to give the title compound as a pale yellow solid (607 mg) m.p. 192°. $\delta H$ ($d^6$ DMSO) 10.70 (1H, bs), 8.93 (1H, s), 7.92 (1H, d, J 8.3 Hz), 7.87 (2H, d, J 8.3 Hz), 7.68 (2H, d, J 8.3 Hz), 7.51 (1 H, t, J 8.0 Hz), 7.33 (1 H, d, J 7.7 Hz) and 1.34 (6H, s).

EXAMPLE 22

4-[4-(1-Amino-1-methylethyl)phenyl]-5-cyano-N-(3-fluorophenyl)pyrimidine-2-amine From 3-fluorophenylguanidinium nitrate (0.91 g, 4.2 mmol), 1-[4-(1-tert-butoxycarbonylamino-1-methylethyl)phenyl]-2-cyano-3-dimethylaminopropenone (1.5 g, 4.2 mmol) and powdered sodium hydroxide (176 mg, 4.3 mmol) to give 4-[4-(1-tert-butoxycarbonylamino-1-methylethyl)phenyl]-5-cyano-N-[3-fluorophenyl]pyrimidine-2-amine as a yellow solid (381 mg) after column chromatography (silica, 2% MeOH in dichloromethane). This compound was treated with TFA acid in $CH_2Cl_2$ as described for Example 8 to give the title compound as a pale yellow solid (161 mg) m.p. 209°. $\delta H$ ($d^6$ DMSO) 10.66 (1H, s), 8.98 (1H, s), 7.92 (2H, dapp, J 8.5 Hz), 7.76 (2H, dapp, J 8.5 Hz), 7.74 (1H, m), 7.56–7.54 (1H, m), 7.40–7.34 (1H, m), 6.91–6.86 (1H, m), 2.48 (2H, bs) and 1.41 (6H, s).

EXAMPLE 23

4-[4-(1-Amino-1-methylethyl)phenyl]-5-cyano-N-(phenyl)pyrimidine-2-amine

From phenylguanidinium nitrate (0.45 g, 2.8 mmol), 1-[4-(1-tert-butoxycarbonylamino-1-methylethyl)phenyl]-2-cyano-3-dimethylaminopropenone (1.0 g, 2.8 mmol) and powdered sodium hydroxide (112 mg, 2.8 mmol) to give 4-[4-(1-tert-butoxycarbonylamino-1-methylethyl)phenyl]-5-cyano-N-[phenyl]pyrimidine-2-amine as a yellow solid (820 mg) after column chromatography (silica, 2% MeOH in dichloromethane). This compound was treated with TFA acid in $CH_2Cl_2$ as described for Example 8 to give the title compound as a pale yellow solid (589 mg) m.p. 303–304°. $\delta H$ ($d^6$ DMSO) 8.72 (1H, s), 8.09 (2H, d, J 8.0 Hz), 7.69–7.58 (5H, m), 7.43–7.38 (2H, m), 7.15 (1H, t, J 7.7 Hz), 2.32 (2H, bs) and 1.68 (6H, s).

EXAMPLE 24

4-[4-(1-Amino-1-methylethyl)phenyl]-5-cyano-N-{4-[2-piperidin-1-ylethyl]phenyl}pyrimidine-2-amine 4-[4-(1-tert-butoxycarbonylamino-1-methylethyl)phenyl]-5-cyano-N-[4-(2-piperidin-1-ylethyl)phenyl]pyrimidine-2-amine (380 mg) was stirred in 50% v/v $CH_2Cl_2$-TFA (5 mL) at room temperature for 30 min. The solvent was removed under reduced pressure and the resulting residue was redissolved in CH$_2$Cl$_2$, washed with saturated aqueous NaHCO$_3$, dried (MgSO$_4$) and evaporated to give the title compound (240 mg) as a yellow solid, m.p. 150°. δH (CDCl$_3$) 8.70 (1H, s), 8.01 (2H, d, J 8.0 Hz), 7.73 (2H, d, J 8.0 Hz), 7.55 (2H, d, J 8.0 Hz), 7.22 (2H, d, J 8.0 Hz), 2.84 (2H, m), 2.63 (2H, m), 2.52 (4H, m) and 1.51 (6H, s).

The pyrimidine used in the above process was prepared by stirring 4-[4-(1-tert-butoxycarbonylamino-1-methylethyl)phenyl]-5-cyano-N-[4-(2-p-toluenesulphonyloxyethyl)phenyl]pyrimidine-2-amine (500 mg, 0.8 mmol) with piperidine (400 ml, 4 mmol) in DMF (5 mL) at 70° for 4 h. The solvent was then removed under reduced pressure and the resulting residue was redissolved in CH$_2$Cl$_2$, washed with saturated aqueous NaHCO$_3$, saturated brine, dried (MgSO$_4$) and concentrated under reduced pressure. The resulting residue was subjected to column chromatography (silica 7% MeOH in dichloromethane) to give the desired material (392 mg) as a yellow solid, m.p. 142°. δH (CDCl$_3$) 8.67 (1H, s), 8.05 (2H, d, J 8.3 Hz), 7.58–7.55 (4H, m), 7.22 (2H, d, J 8.5 Hz), 5.00 (1H, s), 2.88–2.82 (2H, m), 2.63–2.52 (6H, m), 1.66 (12H, bs) and 1.48–1.39 (9H, m).

The tosylate used in the above process was prepared by stirring 4-[4-(1-tert-butoxycarbonylamino-1-methylethyl)phenyl]-5-cyano-N-[4-(2-hydroxyethyl)phenyl]pyrimidine-2-amine (4.02 g, 8.5 mmol), 4-toluene-sulphonyl chloride (2.43 g, 12.7 mmol) and 4-dimethylaminopyridine (150 mg) in dichloromethane (70 ml) at ambient temperature for 12 h. The reaction was diluted with dichloromethane (70 mL) and washed with 2M hydrochloric acid (150 mL). The organic phase was separated and washed with 2M hydrochloric acid, brine and water, dried (MgSO$_4$) and concentrated under reduced pressure. The resulting residue was subjected to column chromatography (silica 40% ethyl acetate-hexane) to give the desired material (3.6 g) as a yellow solid 134°. δH (CDCl$_3$) 8.68 (1H, s), 8.05 (2H, m), 7.72 (2H, d, J 8.4 Hz), 7.57 (4H, t, J 8.5 Hz), 7.29 (2H, d, J 8.0 Hz), 7.15 (2H, d, J 8.5 Hz), 5.00 (1H, s), 4.22 (2H, t, J 7.1 Hz), 2.96 (2H, t, J 7.1 Hz), 2.42 (3H, s), 1.67 (6H, bs) and 1.56 (9H).

The pyrimidine used in the above process was prepared from 4-(2-hydroxyethyl)phenylguanidinium nitrate (3.73 g, 15.4 mmol), 1-[4-(1-tert-butoxy-carbonylamino-1-methylethyl)phenyl]-2-cyano-3-dimethylaminopropenone (5.0 g, 14.0 mmol) and powdered sodium hydroxide (672 mg 16.8 mmol) to give the desired product (7.7 g) as a pale yellow solid, m.p. 114°.

The following compounds of Examples 25–41 and their respective intermediates were prepared in an analogous manner to those in Example 24 except where othewise indicated:

EXAMPLE 25

4-[4-(1-Amino-1-methylethyl)phenyl]-5-cyano-N-[4-(2-imidazol-1-ylethyl)phenyl]pyrimidine-2-amine From 4-[4-(1-tert-butoxycarbonylamino-1-methylethyl)phenyl]-5-cyano-N-[4-(2-imidazol-1-ylethyl)phenyl]pyrimidine-2-amine (370 mg, 0.71 mmol) to give the title compound (290 mg) as a pale yellow solid m.p. 184°. δH (d$^6$ DMSO) 10.51 (1H, s), 8.90 (1H, s), 8.02 (2H, d, J 8.0 Hz), 7.73 (2H, d, J 8.0 Hz), 7.62 (2H, d, J 8.0 Hz), 7.41 (1H, s), 7.13 (3H, m), 6.81 (1H, s), 4.22 (2H, t, J 7.0 Hz), 3.0 (2H, t, J 7.0 Hz) and 1.6 (6H, s).

4-[4-(1-tert-Butoxycarbonylamino-1-methylethyl)phenyl]-5-cyano-N-[4-(2-imidazol-1-ylethyl)phenyl]pyrimidine-2-amine was prepared from 4-[4-(1-tert-butoxy butoxy carbonyl-amino-1-methylethyl)phenyl]-5-cyano-N-[4-(2-p-toluenesulphonyloxyethyl)phenylpyrimidine-2-amine (500 mg,0.8 mmol) and imidazole (272 mg, 4.0 mmol) as a yellow solid (380 mg), m.p. 124°. δH (CDCl$_3$) 8.68 (1H, s), 8.04 (2H, m), 7.66–7.56 (4H, m), 7.32 (1 H, s), 7.04 (3H, m), 6.85 (1H, t, J 1.3 Hz), 5.03 (1H, s), 4.18 (2H, t, J 7.0 Hz), 3.05 (2H, t, J 7.0 Hz), 1.66 (6H, bs) and 1.39 (9H, bs).

EXAMPLE 26

4-[4-(1-Amino-1-methylethyl)phenyl]-5-cyano-N-[4-(2-morpholinoethyl)phenyl]pyrimidine-2-amine From 4-[4-(1-tert-butoxycarbonylamino-1-methylethyl)phenyl]-5cyano-N-[4-(2-morpholinoethyl)phenyl]pyrimidine-2-amine (430 mg) to give the title compound (392 mg) as a pale yellow solid m.p. 156°. δH (d$^6$ DMSO) 10.40 (1H, s), 8.91 (1H, s), 7.93 (2H, d, J 8.4 Hz), 7.74 (2H, d, J 8.4 Hz), 7.64 (2H, d, J 7.8 Hz), 7.19 (2H, d, J 8.5 Hz), 3.56 (4H, m), 3.36 (8H, bm), 2.70 (2H, t, J 7.5 Hz), 2.51–2.46 (2H, m) and 1.49 (6H, s).

4-[4-(1-tert-Butoxycarbonylamino-1-methylethyl)phenyl]-5-cyano-N-[4-(2-morpholinoethyl)phenyl]pyrimidine-2-amine was prepared from 4-[4-(1-tert-butoxy carbonyl-amino-1-methylethyl)phenyl]-5-cyano-N-[4-(2-ptoluene-sulphonyloxyethyl)phenyl]pyrimidine-2-amine (500 mg, 0.80 mmol) and morpholine (350 μL, 4.0 mmol) as a yellow solid (440 mg), m.p. 200°. δH (CDCl$_3$) 8.66 (1H, s), 8.05 (2H, d, J 8.3 Hz), 7.69 (1H, s), 7.58–7.55 (4H, m), 7.21 (2H, d, J 8.5 Hz), 5.04 (1H, s), 3.74 (4H, t, J4.7 hz), 2.83–2.78 (2H, m), 2.63–2.57 (2H, m), 2.53 (4H, t, J 4.7 Hz), 1.65 (6H, bs) and 1.38 (9H, bs).

EXAMPLE 27

4-[4-(1-Amino-1-methylethyl)phenyl]5-cyano-N-{4-[2-(2-ethylimidazol -1-yl)ethyl]phenyl}pyrimidine-2-amine From 4-[4-(1-tert-butoxycarbonylamino-1-methylethyl)phenyl]-5-cyano-N-{4-[2-(2-ethylimidazol-1-yl)ethyl]phenyl}pyrimidine-2-amine to give the title compound (310 mg) as a yellow solid m.p. 138°. δH (d$^6$ DMSO) 10.51 (1H, s), 8.91 (1H, s), 8.00 (2H, d, J 8.0 Hz), 7.71 (2H, d, J 8.0 Hz), 7.62 (2H, d, J 8.0 Hz), 7.11 (2H, d, J 8.0 Hz), 7.03 (1H, s), 6.71 (1H, s), 4.12 (2H, t, J 7.0 Hz), 3.33 (bs), 2.91 (2H, t, J 7.0 Hz), 2.40 (2H, t, J 7.0 Hz), 1.62 (6H, s) and 1.11 (3H, t, J 7.0 Hz).

4-[4-(1-tert-Butoxycarbonylamino-1-methylethyl)phenyl]-5-cyano-N-{4-[2-(2-ethyl-imidazol-1-yl)ethyl]phenyl}pyrimidine-2-amine was prepared from 4-[4-(1-tert-butoxycarbonyl-amino-1-methylethyl)phenyl]-5-cyano-N-[4-(2-p[toluene-sulphonyloxyethyl)phenyl]pyrimidine-2-amine (500 mg, 0.80 mmol) and 2-ethylimidazole (383 mg) to give the title compound (400 mg) as a yellow solid, m.p. 210°. δH (CDCl$_3$) 8.68 (1H, s), 8.05 (2H, d, J 8.4 Hz), 7.60–7.56 (5H, bm), 7.05 (2H, d, J 8.4 Hz), 6.94 (1H, d, J 1.3 Hz), 6.76 (1H, d, J 1.3 Hz), 5.00 (1H, s), 4.07 (2H, t, J 7.1 Hz), 3.00 (2H,t, J 7.1 Hz), 2.49 (2H, q, J 7.5 Hz), 1.67 (6H, bs), 1.39–1.23 (9H,bm) and 0.88 (3H, t, J 7.0 Hz).

EXAMPLE 28

4-[4-(1-Amino-1-methylethyl)phenyl]-5-cyano-N-4-(2-imidazol-1-ylethoxy)phenylpyrimidine-2-amine From 4-[4-(1-tert-butoxycarbonylamino-1-methylethyl)phenyl]-5-cyano-N-[4-(2-imidazol-1-ylethoxy)phenyl]

pyrimidine-2-amine (857 mg, 1.59 mmol) to give the title compound (566 mg) as a yellow solid, m.p. 208–209°. δH (d⁶ DMSO) 10.32 (1H, bs), 8.86 (1H, s), 7.89 (2H, d, J 8.5 Hz), 7.73 (2H, d, J 8.5 Hz), 7.67–7.63 (3H, m), 7.23 (1H, s), 6.94–6.88 (3H, m), 4.33 (2H, t, J 5.0 Hz), 4.22 (2H, t, J 5.1 Hz), 2.01 (2H, bs) and 1.40 (6H, s).

4-[4-(1-tert-Butoxycarbonylamino-1-methylethyl)phenyl]-5-cyano-N-[4-(2-imidazol-1-yl-ethoxy)phenyl]pyrimidine-2-amine was prepared from 4-[4-(1-tert-butoxycarbonyl amino-1-methyl-ethyl)phenyl]-5-cyano-N-{4-[(2-p-toluene-sulphonyloxy)ethoxy]phenyl}pyrimidine-2-amine (2.0g, 3.1 mmol) and imidazole (1.02 g, 15 mmol) as a yellow solid (870 mg). δH (d⁶ DMSO) 10.34 (1H, s), 8.88 (1H, s), 7.90 (2H, d, J 8.5 Hz), 7.68–7.64 (3H, m), 7.53 (2H, d, J 8.5 Hz), 7.31 (1H, bs), 7.24 (1H, t, J 1.1 Hz), 6.93 (2H, d, J 9.0 Hz), 6.89 (1H, t, J 1.0 Hz), 4.35 (2H, t, J 5.2 Hz), 4.23 (2H, t, J 5.2 Hz), 1.54 (6H, s) and 1.34 (9H, bs).

4-[4-(1-tert-butoxycarbonylamino-1-methylethyl)phenyl]-5-cyano-N-{4-[(2-p-toluenesulphonyloxy)ethoxyl]phenyl}pyrimidine-2-amine was prepared from 4-[4-(1-tert-butoxy-carbonylamino-1-methylethyl)phenyl]-5-cyano-N-[4-(2-hydroxyethoxy)phenyl]-pyrimidine-2-amine (2.1g, 4.29 mmol) and 4-toluene sulphonylchloride (1.24 g, 6.5 mmol) as a yellow solid (2.10 g), m.p. 145–146°.

4-[4-(1-tert-butoxycarbonylamino-1-methylethyl)phenyl]-5-cyano-N-[4-(2-hydroxyethoxy)phenyl]pyrimidine-2-amine was prepared from 1-[4-(1-tert-butoxycarbonyl amino-1-methylethyl)phenyl]-5-cyano-3-dimethylaminopropenone (2.16 g, 8.0 mmol), 4-(2-hydroxyethoxy)phenylguanidinium nitrate (2.08 g, 8.0 mmol) and sodium hydroxide (320 mg, 8.0 mmol) as a pale green solid (2.28 g), m.p. 126–127°. δH (CDCl₃) 8.64 (1H, s), 8.06–8.02 (2H, m), 7.58–7.51 (5H, m), 6.97–6.94 (2H, m), 5.03 (1H, bs), 4.14 (2H,t, J 5.2 Hz), 4.00–3.95 (2H, bm), 2.12 (1H, bs), 1.68 (6H, s) and 1.38 (9H, bs).

The guanidine used in the above process was prepared by heating a solution of 4-(2-hydroxyethoxy)aniline (38.0 g, 0.25 mmol), cyanamide (1 7.67 g, 0.421 g) in 25 mL water, and concentrated HNO₃ (17.8 mL, 0.27 mmol) in ethanol (350 mL) for 24 h. The reaction was cooled to 0° and diluted with ether (350 mL). The resulting solid was collected by filtration and dried to give the desired material as a purple solid (42.45 g). δH (d⁶ DMSO) 9.34 (1H, s), 7.18 (4H, bs), 7.16–7.12 (2H, m), 7.01–6.96 (2H, m), 4.85 (1H, t, J 5.3 Hz), 3.98 (2H, t, J 5.2 Hz) and 3.70 (2H, t, J 5.0 Hz).

EXAMPLE 29

4-[4-(1-Amino-1-methylethyl)phenyl]-5-cyano-N-[3-(2-morpholinoethyl)phenyl]pyrimidine-2-amine From 4-[4-(1-tert-butoxycarbonylamino-1-methylethyl)phenyl]-5-cyano-N-[3-(2-morpholinoethyl)phenyl]pyrimidine-2-amine (400 mg, 0.73 mmol) to give the title compound (250 mg) as a pale yellow solid m.p. 166–167°. δH (CDCl₃) 8.69 (1H, s), 8.05 (2H, d, J 8.5 Hz), 7.68 (2H, d, J 8.7 Hz), 7.61 (1H, bs), 7.53–7.4 (2H, m), 7.30 (1H, t, J 7.8 Hz), 7.00 (1H, d, J 7.5 Hz), 3.76–3.73 (4H, m), 2.87–2.81 (2H, m), 2.67–2.61 (2H, m), 2.55–2.52 (4H, m), 1.83 (2H, bs) and 1.54 (6H, s).

4-[4-(1-tert-butoxycarbonylamino-1-methylethyl)phenyl]-5-cyano-N-[3-(2-morpholinoethyl)phenyl]pyrimidine-2-amine was prepared from 4-[4-(1-tert-butoxy carbonyl-amino-1-methylethyl)phenyl]-5-cyano-N-[3-(2-p-toluene-suphonyloxyethyl)phenyl]pyrimidine-2-amine (500 mg, 0.84 mmol) and morpholine (293 μL, 3.36 mmol) as a yellow solid (413 mg). δH (CDCl₃) 8.68 (1H, s), 8.06 (2H, d, J 8.2 Hz), 7.58–7.51 (5H, m), 7.30 (1H, t, J 7.8 Hz), 7.00 (1H, d, J 7.7 Hz), 5.04 (1H, bs), 3.76–3.73 (4H, m), 2.86–2.81 (2H, m), 2.66–2.61 (2H, m), 2.55–2.52 (4H, m), 1.65 (6H, s) and 1.39 (9H, bs).

4-[4-(1-tert-butoxycarbonylamino-1-methylethyl)phenyl]-5-cyano-N-[3-(2-p-toluenesuphonyloxyethyl)phenyl]pyrimidine-2-amine was prepared from 4-[4-(1-tert-butoxy-carbonylamino-1-methylethyl)phenyl]-5-cyano-N-[3-(2-hydroxyethyl phenyl]pyrimidine-2-amine (880 mg) and 4-toluenesulphonylchloride (572 mg, 3.0 mmol) as yellow solid (945 mg). δH (CDCl₃) 8.68 (1H, s), 8.06 (2H, d, J 7.9 Hz), 8.06 (2H, d, J 7.9 Hz), 7.60–7.53 (4H, m), 7.43 (1H, bs), 7.29–7.24 (3H, m), 6.90 (1H, d, J 7.0 Hz), 5.04 (1H, bs), 4.26 (2H, t, J 6.8 Hz), 2.98 (2H, t, J 7.0 Hz), 2.39 (3H, s), 1.66 (6H, s) and 1.39 (9H, bs).

4-[4-(1-tert-butoxycarbonylamino-1-methylethyl)phenyl]-5-cyano-N-[3-(2-hydroxyethyl)phenyl]pyrimidine-2-amine was prepared from 4-[4-(1-tert-butoxycarbonyl amino-1-methyl-ethyl)phenyl]-5-cyano-N-[3-(hydroxyethoxy)phenyl]pyrimidine-2-amine (2.0 g, 5.6 mmol), 3-(2-hydroxyethyl)phenylguanidinium nitrate (1.6 g, 5.6 mmol) and sodium hydroxide (336 mg, 8.4 mmol) as a yellow solid (980 mg), m.p. 164–164°. δH (CDCl₃) 8.66 (1H, s), 8.05 (2H, d, J 8.4 Hz), 7.71 (1H, bs), 7.59–7.51 (4H, m), 7.32 (1H, t, J 7.9 Hz), 7.01 (1H, d, J 7.7 Hz), 5.06 (1H, bs), 3.89 (2H, t, J 6.5 Hz), 2.89 (2H, t, J 6.5 Hz), 1.65 (6H, s) and 1.39 (9H, bs).

EXAMPLE 30

5-Cyano-4-phenyl-N-[4-(2-piperidin-1-ylethyl)phenyl]pyrimidine-2-amine

From 5-cyano-4-phenyl-N-[4-(2-p-toluenesulphonyloxyethyl)phenyl]pyrimidine-2-amine (800 mg, 1.70 mmol) and piperidine (0.84 mL, 8.5 mmol) to give the title compound (367 mg) as a pale yellow solid, m.p. 124–125°. δH (CDCl₃) 8.69 (1H, s), 8.05 (2H, d, J 6.8 Hz), 7.60–7.51 (6H, m), 7.22 (2H, d, J 8.4 Hz), 2.87–2.83 (2H, m), 2.61–2.50 (6H, m), 1.66 (4H, bs) and 1.48–1.43 (2H, m).

5-Cyano-4-phenyl-N-[4-(2-p-toluenesulphonyloxyethyl)phenyl]pyrimidine-2-amine was prepared from 5-cyano-4-phenyl-N-[4-(2-hydroxyethyl)phenyl]pyrimidine-2-amine (3.30 g, 10.43 mmol) and 4-toluenesulphonylchloride (2.19 g, 11.47 mmol) as a pale yellow solid (3.91 g) m.p. 134–135°. δH (d⁶ DMSO) 8.69 (1H, s), 8.05 (2H, dd, J 6.0, 2.0 Hz), 7.72 (2H, d, J 8.3 Hz), 7.61–7.51 (6H, m), 7.29 (2H, d, J 8.1 Hz), 7.14 (2H, d, J 8.5 Hz), 4.21(2H, t, J 7.0 Hz), 2.95 (2H, t, J 7.0 Hz) and 2.41 (3H, s).

5-Cyano-4-phenyl-N-[4-(2-hydroxyethyl)phenyl]pyrimidine-2-amine was prepared from 1-phenyl-2-cyano-3-dimethylaminopropen-1-one (4.0 g, 20 mmol), 4-(2-hydroxyethyl)phenyl-guanidinium nitrate (4.24 g,20 mmol) and sodium hydroxide (800 mg, 20.0 mmol) as a yellow solid (3.50 g), m.p. 142–143°. δH (CDCl₃) 8.68 (1H, s), 8.03 (2H, dd, J 6.0, 2.0 Hz), 7.66 (1H, bs), 7.59–7.51 (5H, m), 7.23 (2H, m), 3.88 (2H, t, J 6.5 Hz), 2.87 (2H, t, J 6.5 Hz) and 1.62 (2H, bs).

EXAMPLE 31

5-Cyano-4-phenyl-N-[4-(2-imidazol-1-ylethyl)phenyl]pyrimidine-2-amine

From 5-cyano-4-phenyl-N-[4-(2-p-toluenesulphonyloxyethyl)phenyl]-pyrimidine-2-amine (800 mg, 1.70 mmol) and imidazole (578 mg, 8.50 mmol) to give the title compound (378 mg) as a yellow solid m.p.

210–211°. δH (CDCl₃/d⁶ DMSO) 10.28 (1H, bs), 8.74 (1H, s), 7.99 (1H, s), 7.94 (1H, d, J 6.7 Hz), 7.65 (2H, d, J 8.74 Hz), 7.57–7.49 (2H, d, J 6.7 Hz), 7.03 (2H, d, J 8.4 Hz), 6.98 (1H, s), 6.85 (1H, t, J 0.9 Hz), 4.16 (2H, t, J 7.1 Hz) and 2.97 (2H, t, J 7.1 Hz).

EXAMPLE 32

5-Cyano-4-phenyl-N-{4-[2-(2-ethylimidazol-1-yl)ethyl]phenyl}-pyrimidine-2-amine

From 5-cyano4-phenyl-N-[4-(2-p-toluenesulphonyloxyethyl)phenyl]pyrimidine-2-amine (800 mg, 1.70 mmol) and 2-ethylimidazole (817 mg, 8.5 mmol) to give the title compound (480 mg) as a yellow solid, m.p. 190–192°. δH (CDCl₃) 8.72 (1H, s), 8.07 (2H, dd, J 5.4, 1.4 Hz), 7.75 (1H, bs), 7.62–7.54 (5H, m), 7.06 (2H, d, J 8.5 Hz), 6.98 (1H, d, J 1.3 Hz), 6.79 (1H, d, J 1.3 Hz), 4.09 (2H, t, J 7.0 Hz), 3.02 (2H, t, J 7.0 Hz), 2.51 (2H, q, J 7.6 Hz) and 1.27 3H, t, J 7.6 Hz).

EXAMPLE 33

5-Cyano-4-phenyl-N-{4-[2-(1,2,4-triazol-1-ylethyl)phenyl}pyrimidine-2-amine

From 5-cyano-4-phenyl-N-[4-(2-p-toluenesulphonyloxyethyl)phenyl]-pyrimidine-2-amine (500 mg,1.12 mmol) and 1,2,4-triazole, sodium salt (122 mg, 1.35 mmol) to give the title compound (188 mg) as a yellow solid, m.p. 217–218°. δH (d⁶ DMSO) 10.48 (1H, s), 8.94 (1H, s), 8.33 (1H, s), 7.96 (3H, m), 7.68–7.59 (5H, m), 7.11 (2H, d, J 8.5 Hz), 4.42 (2H, t, J 7.1 Hz) and 3.08 (2H, t, J 7.1 Hz).

EXAMPLE 34

5-Cyano-4-phenyl-N[4-(2-imidazol-1-ylethoxy)phenyl]pyrimidine-2-amine

From 5-cyano-4-phenyl-N-[4-(2-p-toluenesulphonyloxyethoxy)phenyl]pyrimidine-2-amine (1.54 g,3.17 mmol) and imidazole (1.08 g, 15.8 mmol) to give the title compound (790 mg) as a yellow solid, m.p. 185°. δH (CDCl₃) 8.67 (1H, s), 8.04 (2H, d, J 8.1 Hz), 7.60 (1H, s), 7.58–7.52 (5H, m), 7.45 (1H, s) 7.07 (1H, s), 7.05 (1H, t, J 1.2 Hz), 6.91 (1H, d, J 2.2 Hz), 6.88 (1H, d, J 2.2 Hz), 4.35 (2H, t, J 5.0 Hz) and 4.23 (2H, t, J 5.0 Hz).

5-cyano-4-phenyl-N-[4-(2-p-toluenesulphonyloxyethoxy)phenyl]pyrimidine-2-amine was prepared from 5-cyano-4-phenyl-N-[4-(2-hydroxy-ethoxy)phenyl]pyrimidine-2-amine (1.42 g,4.28 mmol) and 4-toluene-sulphonyl chloride (1.23 g, 6.4 mmol) as a yellow solid, m.p. 147°. δH (CDCl₃) 8.67 (1H, s), 8.05–8.03 (2H, m), 7.83 (2H, dd, J 6.5, 1.8 Hz), 7.58–7.49 (6H, m), 7.35 (2H, dd, J 8.6, 0.9 Hz), 6.83 (2H, d, J 0.9 Hz), 4.38–4.36 (2H, m), 4.18–4.16 (2H, m) and 2.45 (3H, s). 5-cyano-4-phenyl-N-[4-(2-hydroxyethoxy)phenyl]pyrimidine-2-amine was prepared from 1-phenyl-2-cyano-3-dimethylaminopropen-1-one (1.41 g, 7.0 mmol), 4-(2-hydroxy-ethoxy) phenylguanidinium nitrate (2.0 g, 7.7 mmol) and sodium hydroxide (340 mg, 8.4 mmol) to give a yellow solid (1.54 g), m.p. 151°. δH (CDCl) 8.67 (1H, s), 8.04 (2H, d, J 7.7 Hz), 7.58–7.52 (5H, m), 7.45 (1H, s), 6.95 (2H, dd, J 6.7,2.3 Hz), 4.12–4.09 (2H, m), 4.00–3.97 (2H, m) and 2.05–2.01 (1H, m).

EXAMPLE 35

5-Cyano-N-{4-[2-(2-ethylimidazol-1-yl)ethoxy]phenyl}-4-thien-2-yl pyrimidine-2-amine From 5-cyano-N-[4-(2-p-toluenesulphonyloxyethoxy)phenyl]-4-thien-2-yl pyrimidine-2-amine (1.5 g, 3.0 mmol) and 2-ethylimidazole (1.46 g, 15.2 mmol) to give the title compound (0.94 g) as a pale yellow solid, m.p. 205°. δH (CDCl₃) 8.59 (1H, s), 8.41 (1H, d, J 4.0 Hz), 7.63 (1H, d, J 5.0 Hz), 7.53 (2H, m), 7.37 (1H, s), 7.22 (1H, m), 6.97 (2H, d, J 6.5 Hz), 6.88 (2H, d, J 9.0 Hz), 4.24 (4H, dd, J 6.8, 4.3 Hz), 2.78 (2H, q, J 7.8 Hz) and 1.39 (3H, t, J 7.5 Hz).

5cyano-N-[4-(2-p-toluenesulphonyloxyethoxy)phenyl]-4-thien-2-ylpyrimidin-2-amine was prepared from 5-cyano-N-[4-(2-hydroxyethoxy)-phenyl]-4-thien-2-ylpyrimidine-2-amine (8.02 g, 23.7 mmol) and 4-toluene-sulphonylchloride (9.0 g, 47.4 mmol) to give a yellow solid (4.97 g), m.p. 160°. δH (d⁶ DMSO) 10.32 (1H, s), 8.84 (1H, s), 8.26 (1H, d, J 3.9 Hz), 7.99 (1H, d, J 5.0 Hz), 7.80 (2H, d, J 8.3 Hz), 7.64 (2H, m), 7.47 (2H, d, J 8.3hz), 7.33 (1H, t, J 4.5 Hz), 6.85 (2H, d, J 9.0 Hz), 4.33 (2H, t, J 4.0 Hz), 4.15 (2H, m) and 2.41 (3H, s).

EXAMPLE 36

5-Cyano-N-[4-{2-(2-methylimidazol-1-ylethoxy}phenyl]-4-thien-2-ylpyrimidine-2-amine From 5-cyano-N-[4-(2-p-toluenesulphonyloxyethoxy)phenyl]-4-thien-2-yl pyrimidin-2-amine (2.0 g, 4.07 mmol) and 2-methylimidazole (1.67 g, 5 mmol) to give the title compound (0.87 g) as a yellow solid, m.p. 190°. δH (d⁶ DMSO) 10.30 (1H, bs), 8.83 (1H, s), 8.25 (1H, d, J 3.8 Hz), 7.97 (1H, d, J 5.0 Hz), 7.65 (1H, bs), 7.32 (1H, t, J 4.0hz), 7.10 (1H, s), 6.93 (2H, d, J 8.7 Hz), 6.72 (1H, s), 4.23 (4H, m) and 2.32 (3H, s).

EXAMPLE 37

5-Cyano-N-[4-(2-imidazol-1-ylethoxy)phenyl]-4-thien-2-ylpyrimidine-2-amine

From 5-cyano-N-[4-(2-p-toluenesulphonyloxyethoxy)phenyl]-4-thien-2-yl pyrimidin-2-amine (2.45 g,5.0 mmol) and imidazole (1.7 g, 25 mmol) to give the title compound (1.0 g) as a yellow solid, m.p. 199–200°. δH (d⁶ DMSO) 9.90 (1H, bm), 8.76 (1H, d, J 1.0 Hz), 8.26 (1H, m), 7.92 (1H, dd, J 5.0, 1.1 Hz), 7.65 (3H, m), 7.31 (1H, dd, J 5.0, 3.8 Hz), 7.20 (1H, t, J 1.2 Hz), 6.94 (3H, m), 4.36 (2H, m) and 4.30 (2H, m).

EXAMPLE 38

5-Cyano-N-[4-(2-(1,2,4-triazol-1-yl)ethoxy)phenyl]-4-thien-2-ylpyrimidine-2-amine From 5-cyano-N-[4-(2-p-toluenesulphonyloxyethoxy)phenyl[-4-thien-2-yl pyrimidin-2-amine (1.29 g, 3.6 mmol) and 1,2,4-triazole sodium salt (990 mg, 10.9 mmol) to give the title compound (500 mg) as a yellow solid, m.p. 180–182°. δH (d⁶ DMSO) 8.84 (1H, s), 8.56 (1H, s), 8.24 (1H, d, J 4.0 Hz), 7.98–7.99 (2H, m), 7.63 (2H, bs), 7.32 (1H, dd, J 4.0 Hz), 6.92 (2H, d, J 8.8 Hz), 4.57 (2H, t, J 5.1 Hz) and 4.34 (2H, t, J 5.1 Hz).

EXAMPLE 39

5-Cyano-N-[4-(2-(1,3,4-triazol-1-yl)ethoxy)phenyl]-4-thien-2-ylpyrimidine-2-amine From the same reactants in Example 38 and produced as as a side product the title compound was obtained (100 mg) as a yellow solid, m.p. 228°. δH (d⁶ DMSO) 8.84 (1H, s), 8.56 (2H, s), 8.25 (1H, d, J 3.9 Hz), 7.98 (1H, d, J 4.9 Hz), 7.65 (2H, bs), 7.33 (1H, t, J 4.5 Hz), 6.95 (2H, d, J 8.9 Hz), 4.44 (2H, t, J 5.0 Hz) and 4.26 (2H, t, J 5.0 Hz).

EXAMPLE 40

5-Cyano-N-{4-[2-(1H-imidazol-2-ylamino)ethoxy]phenyl}-4-thien-2-ylpyrimidine-2-amine From 5-cyano-N-[4-(2-p-toluenesulphonyloxyethoxy)phenyl]-4-thien-2-yl pyrimidin-2-amine (500 mg, 0.78 mmol), and 2-aminoimidazole sulphate (500 mg, 3.78 mmol) and potassium carbonate (522 mg, 3.78 mmol) to give the title compound (170 mg) as a yellow solid, m.p. 140°. δH 8.84 (1H, s), 8.25 (1H, d, J 4.0 Hz), 7.98 (1H, d, J 5.0 Hz), 7.76–7.60 (2H, m), 7.35–7.32 (1H, m), 6.93 (2H, d, J 8.7 Hz), 6.64 (1H, s), 6.36 (1H, s), 5.34 (1H, m) and 4.08 (4H, m).

EXAMPLE 41

5-Cyano-N-[4-(2-imidazol-1ylethylphenyl]4-thien-2-ylpyrimidine-2-amine

From 5-cyano-[4-thien-2-yl-N-[4-(2-p-toluenesulphonyloxyethyl)phenyl]pyrimidine-2-amine (550 mg,1.15 mmol) and imidazole (393 mg,5.77 mmol) to give the title compound (300 mg) as a yellow solid, m.p. 187°. δH (CDCl$_3$) 8.62 (1H, s), 8.43 (1H, dd, J 3.2, 1.0 Hz), 7.65 (1H, dd, J 5.9, .0 Hz), 7.59 (2H, d, J 8.2 Hz), 7.51 (1H, s), 7.35 (1H, s), 7.24 (1H, dd, J 4.0,1.0 Hz), 7.10–7.05 (3H, m), 6.85 (1H, s), 4.19 (2H, t, J 7.0 Hz) and 3.06 (2H, t, J 7.0 Hz).

5-Cyano4-thien-2-yl-N-[4-(2-p-toluenesulphonyloxyethyl)phenyl]pyrimidine-2-amine was prepared from 5-cyano-N-[4-(2-hydroxyethyl)-phenyl]-4-thien-2-ylpyrimidine-2-amine (1.39 g, 4.30 mmol) and 4-toluenesulphonylchloride (1.23 g, 6.5 mmol) as a yellow solid (1.15 g), m.p. 190°. δH (CDCl$_3$) 8.62 (1H, s), 8.43 (1H, dd, J 3.1, 1.0 Hz), 7.66–7.61 (3H, m), 7.45 (1H, s), 7.28–7.22 (3H, m), 3.73 (2H, t, J 7.3 Hz) and 3.09 (2H, t, J 7.3 Hz).

5-cyano-N-[4-(2-hydroxyethyl)phenyl]4-thien-2-ylpyrimidine-2-amine was prepared from 1-thien-2-yl-2-cyano-3-dimethylaminopropen-1one (2.17 g, 10.5 mmol), 4-(2-hydroxy-ethyl)phenylguanidinium nitrate (2.8 g, 11.6 mmol) and powdered sodium hydroxide (505 mg) as a yellow solid, m.p. 178°. δH (d$^6$ DMSO) 10.36 (1H, s), 8.86 (1H, s), 8.26 (1H, m), 8.00 (1H, d, J 4.1 Hz), 7.64 (2H, m), 7.33 (1H, dd, J 4.0, 1.0 Hz), 7.20 (2H, d, J 8.4 Hz), 4.60 (1H, t, J 5.2 Hz), 3.58 (2H, t, J 7.0 Hz) and 2.69 (2H, t, J 7.0 Hz).

The compounds following Examples 42–71 were prepared in a similar manner to the compound of Example 1:

EXAMPLE 42

5-Cyano-N-[4-(imidazol-1-yl)phenyl]-4-phenylpyrimidine-2-amine

From 1-phenyl-2-cyano-3-dimethylaminopropen-1-one (1.5 g, 7.49 mmol), 4-imidazol-1-ylphenylguanidinium nitrate (2.45 g,7.40 mmol) and sodium hydroxide (600 mg, 15 mmol) to give the title compound (1.40 g) as a yellow solid, m.p. 278–280°. δH 10.69 (1H, bs), 9.00 (1H, s), 8.21 (1H, s), 7.98–7.91 (4H, m), 7.70–7.60 (6H, m) and 7.10 (1H, s).

EXAMPLE 43

5-Cyano-N-[4-(2-dimethylaminoethoxy)phenyl]-4-phenyl pyrimidine-2-amine

From 1-phenyl-2-cyano-3-dimethylaminopropen-1-one (250 mg,1.25 mmol),4-(2-dimethylaminoethoxy) phenylguanidinium nitrate (523 mg, 1.25 mmol) and sodium hydroxide (108 mg, 2.7 mmol) to give the title compound (230 mg) as a yellow solid, m.p. 152–153°. δH (d$^6$ DMSO) 10.37 (1H, s), 8.40 (1H, s), 7.94 (2H, m), 7.62 (5H, m), 6.94 (2H, dt, J 9.0, 2.0 Hz), 4.02 (2H, t, J 5.8 Hz), 2.61 (2H, t, J 5.8 Hz) and 2.21 (6H, s).

EXAMPLE 44

5-Cyano-N-[3,5-dimethyl-4-(2-morpholinoethoxy)phenyl]-4-phenylpyrimidine-2-amine From 1-phenyl-2-cyano-3-dimethylaminopropen-1-one (250 mg, 1.25 mmol), 3,5-dimethyl-4-(2-morpholinoethoxy)phenylguanidinium nitrate (523 mg, 1.25 mmol) and sodium hydroxide (108 mg, 2.7 mmol) to give the title compound (317 mg) as a yellow solid, m.p. 160–162°. δH (d$^6$ DMSO) 10.32 (1H, s), 8.92 (1H, s), 7.96 (2H, m), 7.64–7.59 (3H, m), 7.42 (2H, bs), 3.83 (2H, t, J 5.7 Hz), 3.59 (4H, t, J 4.6 Hz), 2.68 (2H, t, J 5.7 Hz), 2.50 (4H, m) and 2.23 (6H, s).

EXAMPLE 45

5-Cyano-N-[3,5-dimethoxyphenyl]-4-phenylpyrimidine-2-amine

From 1-phenyl-2-cyano-3-dimethylaminopropen-1-one (250 mg,1.25 mmol), 3,5-dimethoxyphenylguanidinium nitrate (321 mg, 1.4 mmol) and sodium hydroxide (56 mg, 1.4 mmol) to give the title compound (280 mg) as a yellow solid m.p. 206–207°. δH (d$^6$ DMSO) 10.47 (1H, s), 8.98 (1H, s), 7.99 (2H, m), 7.63 (3H, m), 7.13 (2H, bs), 6.25 (1H, t, J 2.2 Hz) and 3.78 (3H, s).

EXAMPLE 46

5-Cyano-N-[3,4-dimethoxyphenyl]-4-phenylpyrimidine-2-amine

From 1-phenyl-2-cyano-3-dimethylaminopropen-1-one (250 mg, 1.25 mmol), 3,4-dimethoxyphenylguanidinium nitrate (348 mg, 1.25 mmol) and sodium hydroxide (56 mg) to give the title compound (107 mg) as an orange solid, m.p. 155–157°. δH (d$^6$ DMSO) 9.78 (1H, bs), 8.80 (1H, s), 8.00 (2H, m), 7.63–7.51 (3H, m), 7.25 (1H, dd, J 8.7, 2.5 mmol), 6.94 (1H, d, J 8.7 mmol), 3.79 (3H, s) and 3.78 (3H, s).

EXAMPLE 47

5-Cyano-4-phenyl-N-[phenyl]pyrimidine-2-amine

From 1-phenyl-2-cyano-3-dimethylaminopropen-1-one (1.0 g, 5.0 mmol), phenylguanidinium nitrate (830 mg, 2.5 mmol) and sodium hydroxide (200 mg, 5.0 mmol) to give the title compound (660 mg) as a yellow solid, m.p. 160–161°. δH (CDCl$_3$) 8.71 (1H, s), 8.08–8.05 (2H, m), 7.66–7.51 (6H, m), 7.42–7.36 (2H, m) and 7.19–7.13 (1H, m).

EXAMPLE 48

5-Cyano-4-indol-3-yl-N-(3,4,5-trimethoxyphenyl)pyrimidine-2-amine

From 1-indol-3-yl-2-cyano-3-dimethylaminopropen-1-one (1.0 g, 4.18 mmol), 3,4,5-trimethoxyphenylguanidinium nitrate (1.20 g, 4.18 mmol) and sodium hydroxide (167 mg, 4.18 mmol) to give the title compound (475 mg) as a yellow solid, m.p. 200–201°. δH (d$^6$ DMSO) 12.04 (1H, bs), 10.04

(1H, s), 8.77 (1H, s), 8.52 (1H, s), 8.50 (1H, bs), 7.52 (1H, d, J 8.1 Hz), 7.24 (2H, t, J 7.4 Hz), 7.12 (2H, bs), 3.70 (6H, s) and 3.66 (3H, s).

1-indol-3-yl-2-cyano-3-dimethylaminopropen-1-one was prepared from 3-(cyanoacetyl) indole (4.0 g, mmol) and dimethylformamide dimethylacetal (4.1 mL, 23.9 mmol) as a yellow solid (2.4 g), m.p. 187–188°. δH (d⁶ DMSO) 11.73 (1H, bs), 8.26 (1H, s), 8.12 (1H, dd, J 6.8, 1.3 Hz), 7.98 (1H, s), 7.47–7.44 (1H, m), 7.20–7.09 (2H, m), 3.35 (3H, s) and 3.26 (3H, s).

3-(Cyanoacetyl)indole was prepared by suspending indole (11.71 g, 0.10 mmol) and potassium cyanoacetate (24.6 g, 0.2 mmol) in acetonitrile (300 mL), and to this methanesulphonylchloride (7.7 mL, 0.1 mmol) was added. The resulting mixture was stirred at ambient temperature for 1 h, and then sodium carbonate (10 g in 50 mL water) was added. After 5 min, the organic phase was separated, dried (Na₂SO₄) and concentrated under reduced pressure. The residue was recrystallised from ethanol (100 mL) to give the desired material as an orange solid (4.31 g), m.p. 226–227°. δH (d⁶ DMSO) 12.20 (1H, bs), 8.38 (1H, d, J 2.8 Hz), 8.14–8.10 (1H, m), 7.53–7.50 (1H, m), 7.25–7.21 (2H, m) and 4.49 (2H, s).

EXAMPLE 49

5-Cyano-4-indol-3-yl-N-[4-(1,2,4-triazol-1-yl)phenyl]pyrimidine-2-amine

From 1-indol-3-yl-2-cyano-3-dimethylaminopropen-1-one (289 mg, 1.2 mmol), 4-(1,2,4-triazol-1-yl) phenylguanidinium nitrate (320 mg,1.2 mmol) and sodium hydroxide (48 mg, mmol) to give the title compound (270 mg) as a yellow solid, m.p. 329–330°. δH (d⁶ DMSO) 12.00 (1H, bs), 10.39 (1H, bs), 9.26 (1H, s), 8.84 (1H, s), 8.55 (2H, bm), 8.28–8.21 (1H, m), 7.96 (2H, d, J 8.8 Hz), 7.86 (2H, d, J 8.8 Hz), 7.56–7.52 (1H, m), 7.28–7.15 (2H, m) and 3.30 (1H, bs).

EXAMPLE 50

5-Cyano-4-thiazol-2-yl-N-(3,4,5-trimethoxyphenyl)pyrimidine-2-amine

From 2-cyano-3-dimethylamino-1-thiazol-2-ylpropen-1-one (300 mg, 13.8 mmol), 3,4,5-trimethoxyphenylguanidinium nitrate (436 mg, 15.2 mmol) and sodium hydroxide (61 mg, 15.2 mmol) to give the title compound (324 mg) as a yellow solid, m.p. 223°. δH (d⁶ DMSO) 10.52 (1H, bs), 9.03 (1H, s), 8.28 (1H, d, J 3.0 Hz), 8.22 (1H, d, J 3.0 Hz), 7.23 (2H, s), 3.88 (6H, s) and 3.72 (3H, s).

2-Cyano-3-dimethylamino-1-thiazol-2-ylpropen-1-one was prepared from 2-cyanoacetyl thiazole (400 mg,2.94 mmol) and dimethylformamide dimethylacetal (1.5 mL) as a yellow solid, m.p. 126° δH (CDCl₃) 8.89 (1H, s), 7.96 (1H, d, J 3.3 Hz), 7.60 (1H, d, J 3.1 Hz), 3.54 (3H, s) and 3.35 (3H, s).

2-Cyanoacetylthiazole was prepared by heating a solution of 2-ethoxycarbonyl-thiazole (1.08 g, 6.88 mmol), acetonitrile (360 mL, 7.57 mmol) and sodium hydride [60% dispersion in oil] (303 mg, 7.57 mmol) in benzene (20 mL) and DMF (2 mL) at 800 for 90 min. On cooling the resulting precipitate was collected by filtration and dissolved in water (60 mL). The solution was poured into cold 2M hydrochloric acid (100 mL) and the resulting precipitate collected by filtration to give the desired product (200 mg) as a yellow solid, m.p. 109° δH (CDCl₃) 8.06 (1H, d, J 2.9 Hz), 7.82 (1H, d, J 2.9 Hz) and 4.32 (2H, s).

EXAMPLE 51

5-Cyano-4-thiazol-2-yl-N-[41 2,4-triazol-1-yl)phenyl]pyrimidine-2-amine

From 2-cyano-3-dimethylamino-1-thiazol-2-ylpropen-1-one (300 mg, 1.38 mmol), 4-(1,2,4-triazol-1-yl) phenylguanidinium nitrate (425 mg, 1.38 mmol) and sodium hydroxide (61 mg, 1.52 mmol) to give the title compound (381 mg) as a yellow solid, m.p. 331°. δH (d⁶ DMSO) 10.86 (1H, bs), 9.30 (1H, s), 9.10 (1H, s), 8.31–8.25 (3H, m), 8.01 (2H, dapp, J 8.6 Hz) and 7.93 (2H, dapp, J 8.6 Hz).

EXAMPLE 52

5-Cyano-N-[3,4-dimethoxyphenyl]-4-thiazol-2-ylpyrimidine-2-amine

From 2-cyano-3-dimethylamino-1-thiazol-2-ylpropen-1-one (500 mg, 2.3 mmol), 3,4-dimethoxyphenylguanidinium nitrate (585 mg, 2.3 mmol) and sodium hydroxide (100 mg, 2.3 mmol) to give the title compound (721 mg) as yellow solid, m.p. 258°. δH (d⁶ DMSO) 9.98 (1H, bs), 8.66 (1H, s), 7.96 (1H, d, J 3.1 Hz), 7.87 (1H, d, J 3.1 Hz), 7.20 (1H, d, J 1.8 Hz), 6.96–6.93 (1H, m) and 6.67 (1H, d, J 8.4 Hz) and 5.79 (2H, s).

EXAMPLE 53

5-Cyano-4-thiazol-2-yl-N-{4-[2-(1,2,4triazol-1-yl)ethoxy]phenyl}pyrimidine-2-amine From 2-cyano-3-dimethylamino-1-thiazol-2-ylpropen-1-one (500 mg, 2.3 mmol), 4-[2-(1,2,4-triazol-1-yl)ethoxy]phenylguanidinium nitrate (714 mg, 2.3 mmol) and sodium hydroxide (100 mg, 2.3 mmol) to give the title compound (812 mg) as a yellow solid, m.p. 224°. δH (d⁶ DMSO) 10.02 (1H, s), 8.70 (1H, s), 8.33 (1H, s), 8.01 (1H, d, J 3.1 Hz), 7.91 (1H, d, J 3.1 Hz), 7.77 (1H, s), 7.47 (2H, d, J 8.8 Hz), 6.79–6.76 (2H, m), 4.41 (2H, t, J 5.2 Hz) and 4.23 (2H, t, J 5.2 Hz).

EXAMPLE 54

5-Cyano-4-thiazol-2-yl-N-{4-[2-(1,2,3-triazol-1-yl)ethoxy]phenyl}pyrimidine-2-amine From 2-cyano-3-dimethylamino-1-thiazol-2-ylpropen-1-one (700 mg, 3.2 mmol), 4-[2-(1,2,3-triazol-1-yl)ethoxy]phenylguanidinium nitrate (1.0 g, 3.2 mmol) and sodium hydroxide (136 mg, 3.2 mmol) to give the title compound (0.98 g) as a yellow solid, m.p. 203°. δH (d⁶ DMSO) 10.21 (1H, bs), 8.90 (1H, s), 8.21 (1H, d, J 2.9 Hz), 8.14 (1H, s), 8.11 (1H, d, J 2.9 Hz), 7.73 (1H, s), 7.68–7.66 (2H, m), 6.99–6.95 (2H, m), 4.81 (2H, t, J 5.1 Hz) and 4.47 (2H, t, J 5.1 Hz).

EXAMPLE 55

5-Cyano-4-thiazol-2-yl-N-{4-[2-(1,2,3-triazol-2-yl)ethoxy]phenyl}pyrimidine-2-amine From 2-cyano-3-dimethylamino-1-thiazol-2-ylpropen-1-one (700 mg, 3.2 mmol), 4-[2-(1,2,3-triazol-2-yl)ethoxy]phenylguanidinium nitrate (1.0 g, 3.2 mmol) and sodium hydroxide (136 mg, 3.2 mmol) to give the title compound (1.1 g) as a yellow solid, m.p. 203°. δH (d⁶ DMSO) 10.19 (1H, s), 8.87 (1H, s), 8.19 (1H, d, J 3.1 Hz), 8.09 (1H, d, J 3.1 Hz), 7.76 (2H, s), 7.66–7.62 (2H, m), 6.95–6.91 (2H, m), 4.804.78 (2H, m) and 4.52 (2H, t, J 5.5 Hz).

EXAMPLE 56

5-Cyano-N-[4-(2-imidazol-1-ylethoxy)phenyl]4-thiazol-2-ylpyrimidine-2-amine

From 2-cyano-3-dimethylamino-1-thiazol-2-ylpropen-1-one (700 mg, 3.2 mmol), 4-(2-imidazol-1-ylethoxy) phenylguanidinium nitrate (1.0 g, 3.2 mmol) and sodium hydroxide (160 mg, 3.8 mmol) to give the title compound (981 mg) as a yellow solid, m.p. 221°. δH (d$^6$ DMSO) 9.93 (1H, s), 8.83 (1H, s), 8.16 (1H, d, J 3.12 Hz), 8.03 (1H, d, J 3.1 Hz), 7.67–7.62 (3H, m),7.18 (1H, d, J 1.0 Hz), 6.99–6.91 (3H, m) and 4.374.29 (4H, m).

EXAMPLE 57

5-Cyano-N-[4-fluorophenyl]-4-thiazol-2-ylpyrimidine-2-amine

From 2-cyano-3-dimethylamino-1-thiazol-2-ylpropen-1-one (700 mg, 3.2 mmol), 4-fluorophenylguanidinium nitrate (700 mg, 3.2 mmol) and sodium hydroxide (160 mg, 3.2 mmol) to give the title compound (891 mg) as a yellow solid, m.p. 263°. δH (d$^6$ DMSO) 10.10 (1H, s), 8.88 (1H, s), 8.17 (1H, d, J 3.1 Hz), 8.05 (1H, d, J 3.1 Hz), 7.78–7.75 (2H, m), 7.20–7.15 (2H, m).

EXAMPLE 58

5-Cyano-4-phenyl-N-{4-[2-(1,2,4-triazol-1-yl)ethoxy]phenyl}pyrimidine-2-amine

From 1-phenyl-2-cyano-3-dimethylaminopropen-1-one (470 mg, 2.35 mmol), 4-[2-(1,2,4-triazol-1-yl)ethoxy] phenylguanidinium nitrate (800 mg, 2.6 mmol) and sodium hydroxide (113 mg, 2.8 mmol) to give the title compound (390 mg) as a yellow solid m.p. 105°. δH (d$^6$ DMSO) 10.36 (1H, s), 8.89 (1H, s), 7.97 (1H, s), 7.92 (2H, d, J 7.9 Hz), 7.61–7.58 (5H, m), 6.90 (2H, d, J 9.1 Hz), 4.56 (2H, t, J 5.0 Hz) and 4.32 (2H, t, J 5.0 Hz).

EXAMPLE 59

5-Cyano-4-phenyl-N-{4-[2-(1,2,3-triazol-1-yl)ethoxy]phenyl}pyrimidine-2-amine

From 1-phenyl-2-cyano-3-dimethylaminopropen-1-one (412 mg, 2.05 mmol), 4-[2-(1,2,3-triazol-1-yl)ethoxy] phenylguanidinium nitrate (700 mg, 2.06 mmol) and sodium hydroxide (100 mg, 2.5 mmol) to give the title compound (300 mg) as a yellow solid m.p. 178°. δH 10.37 (1H, s), 8.90 (1H, s), 7.92 (2H, d, J 7.9 Hz), 7.73 (1H, s), 7.61–7.58 (5H, m), 6.92 (2H, d, J 9.1 Hz), 4.77 (2H, t, 5.1 Hz) and 4.38 (2H, t, J 5.1 Hz).

EXAMPLE 60

5-Cyano-4-phenyl-N-{4-[2-(1,2,3-triazol-2-yl)ethoxy]phenyl}pyrimidine-2-amine

From 1-phenyl-2-cyano-3-dimethylaminopropen-1-one (470 mg, 2.55 mmol), 4-[2-(1,2,3-triazol-1-yl)ethoxy] phenylguanidinium nitrate (800 mg, 2.56 mmol) and sodium hydroxide (113 mg, 2.8 mmol) to give the title compound (430 mg) as a yellow solid m.p. 156°. δH (d$^6$ DMSO) 10.30 (1H, s), 8.89 (1H, s), 7.92 (2H, d, J 7.9 Hz), 7.79 (2H, s), 7.61–7.58 (5H, m), 6.89 (2H, d, J 9.1 Hz), 4.78 (2H, t, J 5.1 Hz) and 4.46 (2H, t, J 5.1 Hz).

EXAMPLE 61

5-Cyano-N-[4-hydroxyphenyl]-4-phenylpyrimidine-2-amine

From 1-phenyl-2-cyano-3-dimethylaminopropen-1-one (1.51 g, 7.55 mmol), 4-hydroxyphenylguanidinium nitrate (1.78 g, 8.3 mmol) and sodium hydroxide (362 mg, 9.06 mg) to give the title compound (1.23 g) as a yellow solid, m.p. 201°. δH (d$^6$ DMSO) 10.23 (1H, s), 9.26 (1H, s), 8.85 (1H, d, J 1.0 Hz), 7.92 (2H, dd, J 7.0, 1.0 Hz), 7.59 (3H, m), 7.48 (2H, d, J 8.0 Hz) and 6.73 (2H, d, J 8.0 Hz).

EXAMPLE 62

5-Cyano-N-[4-(2-hydroxyethoxy)phenyl]-4-pyridin-3-ylpyrimidine-2-amine

From 2-cyano-3-dimethylamino-1-pyridin-3-ylpropen-1-one (1.20 g, 5.95 mmol), 4-(2-hydroxyethoxy) phenylguanidinium nitrate (1.54 g, 5.95 mmol) and sodium hydroxide (262 mg, 6.34 mmol) to give the title compound (1.28 g) as a yellow solid, m.p. 209–210°. δH (d$^6$ DMSO) 10.43 (1H, bs), 9.07 (1H, d, J 1.9 Hz), 8.93 (1H, s), 8.77 (1H, dd, J 4.8, 1.6 Hz), 8.31–8.28 (1H, m), 7.65–7.60 (3H, m), 6.92 (2H, d, J 9.0 Hz), 4.82 (1H, t, J 5.6 Hz), 3.96 (2H, t, J 5.0 Hz) and 3.69 (2H, q, J 5.1 Hz).

EXAMPLE 63

5-Cyano-4-pyridin-3-yl-N-[4-(1,2,4-triazol-1-yl)phenyl]pyrimidine-2-amine

From 2-cyano-3-dimethylamino-1-pyridin-3-ylpropen-1-one (516 mg, 2.56 mmol), 4-(1,2,4-triazol-1-yl) phenylguanidinium nitrate (679 mg, 2.56 mmol) and sodium hydroxide (113 mg, 2.82 mmol) to give the title compound (425 mg) as a yellow solid, m.p. 250–251°. δH 10.79 (1H, bs), 9.20 (1H, s), 9.12 (1H, s), 9.04 (1H, s), 8.81 (1H, bm), 8.35–8.32 (1H, bm), 8.20 (1H, s), 7.93 (2H, d, J 8.6 Hz), 7.82 (2H, d, J 8.6 Hz) and 7.65 (1H, bs).

EXAMPLE 64

5-Cyano-N-[4-morpholinophenyl]-4-pyridin-3-ylpyrimidine-2-amine

From 2-cyano-3-dimethylamino-1-pyridin-3-ylpropen-1-one (516 mg, 2.56 mmol), 4-morpholinophenylguanidinium nitrate (725 mg, 2.56 mmol) and sodium hydroxide (113 mg, 2.82 mmol) to give the title compound (707 mg) as an orange solid, m.p. 199–200°. δH (d$^6$ DMSO) 10.39 (1H, bs), 9.07 (1H, d, J 1.8 Hz), 8.91 (1H, s), 8.78 (1H, dd, J 4.9,1.6 Hz), 8.31–8.28 (1H, m), 7.65–7.56 (3H, m), 6.93 (2H, d, J 9.1 Hz), 3.74–3.70 (4H, m) and 3.07–3.04 (4H, m)

EXAMPLE 65

5-Cyano-N-[4-fluorophenyl]-4-indol-3-ylpyrimidine-2-amine

From 1-indol-3-yl-2-cyano-3-dimethylaminopropen-1-one (950 mg, 3.97 mmol), 4-fluorophenylguanidinium nitrate (858 mg, 3.97 mmol) and sodium hydroxide (176 mg) to give the title compound (200 mg) as an off-white solid, m.p. 256–257°. δH (d$^6$DMSO) 11.83 (1H, bs), 9.91 (1H, s), 8.73 (1H, s), 8.51 (1H, s), 8.50–8.47 (1H, m), 7.78–7.73 (2H, m), 7.53 (1H, dt, J 7.2, 0.8 Hz) and 7.27–7.13 (4H, m).

EXAMPLE 66

5-Cyano-N-[4-(2-imidazol-1-ylethoxy)phenyl]-4-indol-3-ylpyrimidine-2-amine

From 1-indol-3-yl-2-cyano-3-dimethylaminopropen-1-one (300 mg, 1.25 mmol), 4-(2-imidazol-1-ylethoxy)

phenylguanidinium nitrate (465 mg, 1.25 mmol) and sodium hydroxide (100 mg, 2.5 mmol) to give the title compound (150 mg) as a yellow solid, m.p. 238–239°. δH (d$^6$ DMSO) 12.02 (1H, bs), 10.04 (1H, s), 8.72 (1H, s), 8.55 (1H, s), 8.33 (1H, bm), 7.68 (1H, s), 7.63–7.55 (3H, m), 7.28–7.23 (2H, m), 7.22–7.05 (2H, bm), 6.98–6.91 (3H, m), 4.52 (2H, t, J 5.0 Hz) and 4.26 (2H, t, J 5.0 Hz).

EXAMPLE 67

5-Cyano-4-pyridin-3-yl-N-{4-[2-(1,2,4-triazol-1-yl)ethoxy]phenyl}pyrimidine-2-amine From 2-cyano-3-dimethylamino-1-pyridin-3-ylpropen-1-one (800 mg, 3.97 mmol), 4-[2-(1,2,4-triazol-1-yl)ethoxy]phenylguanidinium nitrate (1.23 g, 3.97 mmol) and sodium hydroxide (176 mg, 4.4 mmol) to give the title compound (1.0 g) as a yellow solid, m.p. 180–181°. δH (d$^6$ DMSO) 10.45 (1H, bs), 9.07 (1H, d, J 1.8 Hz), 8.93 (1H, s), 8.77 (1H, dd, J 4.8,1.5 Hz), 8.55 (1H, s), 8.29 (1H, d, J 8.1 Hz), 7.97 (1H, s), 7.64–7.60 (3H, m), 6.91 (2H, d, J 9.0 Hz), 4.56 (2H, t, J 5.0 Hz) and 4.32 (2H, t, J 5.0 Hz).

EXAMPLE 68

5-Cyano-4-pyridin-3-yl-N-{4-[2-(1,2,3-triazol-1-yl)ethoxy]phenyl}pyrimidine-2-amine From 2-cyano-3-dimethylamino-1-pyridin-3-ylpropen-1-one (516 mg, 2.56 mmol), 4-[2-(1,2,3-triazol-1-yl)ethoxy]phenylguanidinium nitrate (800 mg, 2.56 mmol) and sodium hydroxide (113 mg, 2.82 mmol) to give the title compound (531 mg) as a yellow solid, m.p. 177–178°. δH (d$^6$ DMSO) 10.45 (1H, bs), 9.08 (1H, s), 8.93 (1H, s), 8.78 (1H, dd, J 4.8,1.5 Hz), 8.31–8.28 (1H, m), 8.17 (1H, s), 7.73 (1H, s), 7.65–7.60 (3H, m), 6.92 (2H, d, J 9.0 Hz), 4.77 (2H, t, J 5.0 Hz).

EXAMPLE 69

5-Cyano-4-pyridin-3-yl-N-{4-[2-(1.2.3-triazol-1-2-yl)ethoxy]phenyl}pyrimidine-2-amine From 2-cyano-3-dimethylamino-1-pyridin-3-ylprope-1-one (800 mg, 3.97 mmol), 4-[2-(1,2,3-triazol-2-yl)ethoxy]phenylguanidinium nitrate (1.23 g, 3.97 mmol) and sodium hydroxide (176 mg, 4.4 mmol) to give the title compound (970 mg) as a yellow solid, m.p. 179–180°. δH (d$^6$ DMSO) 10.45 (1H, bs), 9.08 (1H, d, J 1.6 Hz), 8.93 (1H, s), 8.78 (1H, dd, J 5.0,1.6 Hz), 8.32–827 (1H, m), 7.79 (2H, s), 7.65–7.59 (3H, m), 6.90 (2H, d, J 9.1 Hz), 4.78 (2H, t, J 5.2 Hz) and 4.46 (2H, t, J 5.1 Hz).

EXAMPLE 70

5-Cyano-N{4-[2-(1,2,3-triazol-1-yl)ethoxy]phenyl}4-thien3-ylpyrimidine-2-amine

From 2-cyano-3-dimethylamino-1-thien-3-ylpropen-1-one (557 mg, 2.7 mmol), 4-[2-(1,2,3-triazol-1-yl)ethoxy]phenylguanidinium nitrate (920 mg, 3.0 mmol) and sodium hydroxide (130 mg, 3.2 mmol) to give the title compound (710 mg) as a yellow solid, m.p. 177°. δH (d$^6$ DMSO) 10.28 (1H, s), 8.84 (1H,s), 8.48 (1H, s), 8.18 (1H, d, J 0.8 Hz), 7.78–7.73 (3H, m), 7.61 (2H, d, J 7.6 Hz), 6.91 (2H, d, J 8.9 Hz) and 4.77 (2H, t, J 5.0 Hz).

2-Cyano-3-dimethylamino-1-thien-3-ylpropen-1-one was prepared from 3-cyanoacetyl thiophene (7.64 g,50.56 mmol) and dimethylformamide dimethylacetal (20 mL, 152 mmol) as a yellow solid (6.6 g), m.p. 134°. δH (CDCl$_3$) 8.27 (1H, dd, J 3.0, 1.3 Hz), 8.00 (1H, s), 7.61 (1H, dd, J 5.0 Hz), 7.27 (1H, dd, J 5.0,3.0 Hz), 3.48 (3H, s) and 3.29 (3H, s).

3-Cyanoacetylthiophene was prepared in a similar manner to the analogous starting material of Example 8 from 3-isoxazol-5-ylthiophene (8.15 g, 53.9 mmol) and a freshly prepared solution of sodium ethoxide [1.24 g, 53.9 mmol sodium in ethanol (100 mL)] to give the desired material (7.76 g) as an orange solid, δH (CDCl$_3$) 8.16 (1H, dd, J 5.0, 1.3 Hz), 7.55 (1H, dd, J5.0,2.3 Hz), 7.40 (1H, dd, J 5.0, 2.3 Hz) and 3.96 (2H, m).

3-Isoxazol-5-ylthiophene was prepared in a similar manner to the analogous starting material of Example 8 from 3-dimethylamino-1-thien-3-ylpropen-1-one (10 g, 55.2 mmol) and hydroxylamine hydrochloride (4.2 g, 60.7 mmol) to give the desired product (8.15 g) as a colourless oil, δH (CDCl$_3$) 8.18 (1H, d, J 1.9 Hz), 7.72 (1H, t, J 2.1 Hz), 7.34 (2H, d, J 2.1 Hz) and 6.29 (1H, d, J 1.8 Hz).

3-dimethylamino-1-thien-3-ylpropen-1-one was prepared from 3-acetylthiophene (15.0 g) and dimethylformamide dimethylacetal (47.5 mL, 357 mmol) as a yellow solid (14 g), m.p. 98°. δH (CDCl$_3$) 7.90 (1H, dd, J 3.0, 1.0 Hz), 7.76 (1H, d, J 12.4 Hz), 7.53 (1H, dd, J 5.9,1.0 Hz), 7.28–7.25 (1H, m), 5.57 (1H,d, J 12.4 Hz) and 3.03 (6H, bs).

EXAMPLE 71

5-Cyano-N-[4-(2-(1,2,4-triazol-1-ylethyl)phenyl]-4-thien-3-ylpyrimidine-2-amine

From 2-cyano-3-dimethylamino-1-thien-3-ylpropen-1-one (800 mg, 3.9 mmol), 4-[2-(1,2,4-triazol-1-yl)ethyl]phenylguanidinium nitrate (1.26 g, 4.3 mmol) and sodium hydroxide (186 mg, 4.7 mmol) to give the title compound (721 mg) as a light orange solid, m.p. 209°. δH (d$^6$ DMSO) 10.37 (1H, s), 8.88 (1H, s), 8.49 (1H, s), 8.31 (1H, s), 7.94 (1H, s), 7.80–7.76 (2H, m), 7.63 (2H, d, J 8.5 Hz), 7.10 (2H, d, J 8.5 Hz), 4.41 (2H, t, J 7.0 Hz) and 3.07 (2H, t, J 7.0 Hz).

4-[2-(1,2,4-Triazol-1-yl)ethyl]phenylguanidinium nitrate was prepared from 4-[2-(1,2,4-triazol-1-yl)ethyl]aniline (5.75 g, 30.4 mmol), cyanamide (2.17 g, 51.7 mmol in water [2 mL] and concentrated HNO$_3$ (2.2 mL, 33.3 mmol) as a pink solid, m.p. 183°. δH (d$^6$ DMSO) 9.40 (1H, bs), 8.33 (1H, s), 7.94 (1H, s), 7.27–7.19 (4H,m), 7.14–7.11 (2H, m),4.42 (2H, t, J 7.2 Hz) and 3.11 (2H, t, J 7.2 Hz).

4-[2-(1,2,4-triazol-1-yl)ethyl]aniline was prepared from 4-[2-(1,2,4-triazol-1-yl)ethyl]-nitro benzene (7.0 g, 32.1 mmol) in a manner similar to the analogous intermediate of Example 12 as an off white solid (5.8 g), m.p. 79°. δH 7.93 (1H, s), 7.73 (1H, s), 6.79 (2H, d, J 8.5 Hz), 6.58 (2H, d, J 8.5 Hz), 4.31 (2H, t, J 7.0 Hz), 3.30 (2H,bs) and 3.03 (2H t, J7.0 Hz).

4-[2-(1,2,4-triazol-1-yl)ethyl]nitrobenzene was prepared from 4-[2-p-toluenesulphonyloxy ethyl]nitrobenzene (2.77 g, 8.6 mmol) and 1,2,4-triazole sodium salt (942 mg, 10.3 mmol) as a pink solid (2.0 g), m.p. 97°. δH (CDCl$_3$) 8.12 (2H, d, J 9.0 Hz), 8.00 (1H, s), 7.80 (1H, s), 7.20 (2H, m), 4.44 (2H, t, J 7.0 Hz) and 3.32 (2H, t, J 7.0 Hz).

4-[2-p-toluenesulphonyloxyethyl]nitrobenzene was prepared from 4-nitrophenethyl alcohol (20.0 g, 120 mmol) and 4-toluenesulphonyl chloride (34.2 g, 180 mmol) as a yellow solid (3.0 g), m.p. 133°. δH (CDCl$_3$) 8.10 (2H, d, J 9.0 Hz), 7.66 (2H, d, J 9.0 Hz), 7.26 (4H, m), 4.29 (2H, t, J 6.0 Hz), 3.07 (2H, t, J 6.0 Hz) and 2.43 (3H, s).

EXAMPLE 72

4-(2-Aminopyridin-5-yl)-5-cyano-N-(4-fluorophenyl)pyrimidine-2-amine

To a suspension of 5-cyano-N-(4-fluorophenyl)-4-[2-(4-methoxy-benzylamino)pyridin-5-yl]pyrimidine-2-amine (104 mg, 0.24 mmol) in acetonitrile (4 mL), MeOH (2 mL) and dichloromethane (2 mL), was added dropwise a solution of ceric ammonium nitrate (133 mg, 0.24 mmol) in water (1 mL). After 0.5 h the reaction was poured into saturated NaHCO$_3$ and extracted with CHCl$_2$. The organic phase was dried (MgSO$_4$) and concentrated under reduced pressure to give the title compound (42 mg) as a buff solid, m.p. 289°. δH (d$^6$ DMSO) 9.93 (1H, s), 8.76 (1H, d, J 2.3 Hz), 8.74 (1H, s), 8.09 (1H, dd, J 8.8, 2.5 Hz), 7.77–7.73 (2H, bm), 7.18–7.13 (2H, m), 6.85 (1H, s) and 6.63 (1H, d, J 8.8 Hz).

5-cyano-N-(4-fluorophenyl)-4-[2-(4-methoxybenzylamino)pyridin-5-yl]-pyrimidine-2-amine was prepared in a similar manner to the title compound of Example 7 from 4-(2-chloropyridin-5-yl)-5-cyano-N-(4-fluoro-phenyl)pyrimidine-2-amine (764 mg, 2.3 mmol) and p-methoxybenzyl-amine (644 mg, 4.6 mmol) as a yellow solid (432 mg). δH (d$^6$ DMSO) 10.35 (1H, s), 8.82 (1H, s), 8.77 (1H, d, J 2.3 Hz), 8.04 (1H, dd, J 8.9, 2.3 Hz), 7.84 (1H, t, J 5.6 Hz), 7.77–7.74 (1H, m), 7.28 (2H, d, J 8.6 Hz), 7.21 (2H, t, J 8.9 Hz), 6.90 (2H, d, J 8.6 Hz), 6.66 (1H, d, J 8.9 Hz), 4.51 (2H, s) and 3.73 (3H, s).

4-[2-Chloropyridin-5-yl]-5-cyano-N-(4-fluorophenyl) pyrimidine-2-amine was prepared from 1-(2-chloropyridin-5-yl)-2-cyano-3-dimethylamino propen-1-one (8.0 g, 36 mmol), 4-fluorophenylguanidinium nitrate (8.23 g, 37.8 mmol) and sodium hydroxide (1.49 g, 37.8 mmol) as a yellow solid (7.23 g). δH (d$^6$ DMSO) 10.66 (1H, bs), 9.00 (1H, s), 8.95 (1H, d, J 2.3 Hz), 8.38 (1H, dd, J 8.4,2.5 Hz), 7.80 (1H, d, J 8.4 Hz), 7.77–7.74 (2H, m) and 7.24–7.20 (2H, m).

EXAMPLE 73

5-Cyano-4-{2-([2-(diethylamino)ethyl]amino) pyridin-5-yl}-N-(4-fluorophenyl) pyrimidine-2-amine From 4-[2-Chloropyridin-5-yl]-5-cyano-N-(4-fluorophenyl)pyrimidine-2-amine (600 mg, 1.8 mmol) and N,N-diethylethylenediamine (430 mg) in a manner analogous to the compound of Example 7, to give the title compound (197 mg) as a yellow solid, m.p. 166°. δH (d$^6$ DMSO) 9.79 (1H, bs), 8.83 (1H, d, J 2.3 Hz), 8.72 (1H, s), 8.08 (1H, dd, J 8.9, 2.3 Hz), 7.76–7.72 (2H, m), 7.17–7.11 (2H, m), 6.73 (1H, bs), 6.65 (1H, d, J 8.9 Hz), 3.53–3.48 (2H, m), 2.85 (2H, bs), 2.73–2.69 (2H, m), 2.61–2.51 (4H, m) and 1.78–1.70 (4H, m).

EXAMPLE 74

4-[4-(1-Acetamido-1-methylethyl)phenyl]-5-cyano-N -4-fluorophenyl pyrimidine-2-amine To a suspension of the compound of Example 20 (100 mg 0.29 mmol) in CHCl$_3$ (8 mL) was added pyridine (0.1 mL) and acetic anhydride (0.1 mL). The reaction was stirred at ambient temperature for 6 h. The reaction was then washed with 2M HCl and saturated NaHCO$_3$, dried (MgSO$_4$), and concentrated under reduced pressure to give the title compound (103 mg) as a yellow solid, m.p. 212–216°. δH 8.69 (1H, s), 8.06 (2H, d, J 8.4 Hz), 7.63–7.60 (2H, m), 7.56 (2H, d, J 8.4 Hz), 7.12–7.08 (2H, m), 5.82 (1H, s), 2.03 (3H, s) and 1.74 (6H, s).

EXAMPLE 75

5-Cyano-4-[4-(1-dimethylamino-1-methylethyl) phenyl]-N-(4-fluorophenyl)pyrimidine-2-amine The compound of Example 20 (500 mg, 1.44 mmol) was heated at reflux in formic acid (10 mL) and 37% aqueous formaldehyde (10 mL) for 4 days. The reaction was diluted in 100 mL dichloromethane and concentrated under reduced pressure. The resulting residue was redissolved in dichloromethane (100 mL) and washed with 2M NaOH, dried (MgSO$_4$) and again concentrated under reduced pressure. The residue was subjected to column chromatography (silica 10–15% MeOH-dichloromethane) to give the title compound (411 mg) as a yellow solid, m.p. 179°. δH (CDCl$_3$) 8.61 (1H, s), 7.94 (2H, d, J 8.1 Hz), 7.63 (2H, d, J 8.3 Hz), 7.51–7.48 (2H, s), 7.04–7.01 (2H, m), 2.12 (6H, s) and 1.32 (6H, s).

EXAMPLE 76

5-Cyano-N-[4-(1,2,4-triazol-1-yl)phenyl]-4-[4-(1-dimethylamino-1-methylethyl)phenyl]pyrimidine-2-amine In a manner analogous to the compound of Example 75, from the compound of Example 11 (750 mg, 1,76 mmol) to give the title compound (687 mg) as a yellow solid, m.p.235–237°. δH (d$^6$ DMSO) 10.68 (1H, bs), 9.23 (1H, s), 8.99 (1H, J 1.9 Hz), 8.21 (1H, s), 7.99–7.96 (4H, m), 7.85 (2H, dd, J 7.1, 1.9 Hz), 7.72 (2H, d, J 8.5 Hz), 2.13 (6H, s) and 1.35 (6H, s).

EXAMPLE 77

5-Cyano-4-[4-(1-methyl-1-pyrrolidin-1-ylethyl) phenyl]-N-(4-fluorophenyl)pyrimidine-2-amine To a solution of the compound (1.0 g,2.88 mmol) of Example 20 in DMF (20 mL) was added potassium carbonate (786 mg, 5.7 mmol) and 1,4-dibromobutane (622 mg, 2.88 mmol) and the resulting mixture stirred at 60° for 12 h. The reaction was partitioned between brine and ethyl acetate then the organic phase was dried (MgSO$_4$) and concentrated under reduced pressure. The residue was subjected to column chromatography to give the title compound (591 mg) as a yellow solid, m.p. 124°. δH (d$^6$ DMSO) 8.58 (1H, s), 7.94 (2H, dapp, J 8.4 Hz), 7.63 (4H, m), 6.96 (2H, tapp, J 8.7 Hz), 3.23 (4H, s), 2.61 (4H, s) and 1.47 (6H, s).

EXAMPLE 78

5-Cyano-4-{[4-(imidazol-1-yl)methyl]phenyl}-N-(3, 4,5-trimethoxyphenyl)pyrimidine-2-amine From 2-cyano-3-dimethylamino-1-[(4-imidazol-1-ylmethyl)phenyl]propen-1-one (260 mg,0.89 mmol), 3,4,5-trimethoxyphenylguanidinium nitrate (308 mg, 1.07 mmol) and sodium hydroxide (46 mg, 1.16 mmol) in a similar manner to the compound of Example 1 to give the title compound (80 mg) as a yellow solid, m.p. 253°. δH (d$^6$ DMSO) 10.07 (1H, bs), 8.86 (1H, s), 7.99 (2H, dt, J 8.4, 1.9 Hz), 7.72 (1H, s), 7.43 (2H, dt, J 8.4,1.9 Hz), 7.21 (2H, s), 7.17 (1H, t, J 1.2 Hz), 6.94 (1H, t, J 2.1 Hz), 5.31 (2H, s), 3.77 (6H, s) and 3.67 (3H, s).

2-Cyano-3-dimethylamino-1-[(4-imidazol-1-ylmethyl) phenyl]propen-1-one was prepared by the addition of 3-hydroxy-3-(4-(imidazol-1-ylmethyl)phenyl)acrylonitrile, lithium salt (2.16 g, 10.0 mmol) to a solution of MeOH-acetyl chloride (15 mL–1 mL) followed by dimethylformamide dimethylacetal (1.3 mL). The reaction was stirred at room temperature for 1 h, then concentrated under reduced pressure. The resulting residue was partitioned between ethyl acetate and saturated Na$_2$CO$_3$. The organic phase was dried (MgSO$_4$) and concentrated under reduced pressure. After chromatography (silica, 5–8% MeOH—CH$_2$Cl$_2$) of the residue the desired material was obtained as a yellow oil (260 mg). δH (300 MHz) 7.94 (1H, s), 7.75 (2H, dt, J 8.3,1.8 Hz), 7.54 (1H, s), 7.16 (2H, d, J 8.5 Hz), 7.08 (1H, t, J 1.0 Hz), 6.89 (1H, t, J 1.3 Hz), 5.14 (2H, s), 3.46 (3H, s) and 3.28 (3H, s).

3-Hydroxy-3-(4-(imidazol-1-ylmethyl)phenyl) acrylonitrile, lithium salt was prepared as follows:- Acetonitrile (1.04 mL, 20.0 mmol)was added to a solution of lithium bistrimethylamide (20 mL 1.0M in THF, 20.0 mmol) at −78° under a nitrogen atmosphere, and the resulting mixture stirred for 20 min. A solution of methyl 4-(imidazol-1-ylmethyl)benzoate (2.16 g, 100 mmol) in THF was added dropwise and the reaction temperature then allowed to warm to room temperature over a 3 h period. The reaction was diluted with diethyl ether (30 mL) and the resulting solid collected by filtration washing further with ether (3×30 mL). The solid was dried under vacuum to give the desired material as a yellow solid (2.65 g) and was used without purification. δH (d⁶ DMSO) 7.72 (1H, s), 7.59 (2H, d, J 8.1 Hz), 7.15 (1H, s), 7.10 (2H, d, J 8.2 Hz), 6.88 (1H s), 5.13 (2H, s) and 3.93 (1H, s).

EXAMPLE 79

5-Cyano-N-[3-fluorophenyl]-4-[4-(imidazol-1-yl) phenyl]pyrimidine-2-amine

From 2-cyano-3-dimethylamino-1-(4-imidazol-1-ylphenyl)propen-1-one (480 mg, 1.8 mmol), 3-fluorophenylguanidinium nitrate (480 mg, 1.98 mmol) and sodium hydroxide (87 mg) in a similar manner to the compound of Example 1 to give the title compound (412 mg) as a yellow solid, m.p. 300°. δH (d⁶ DMSO) 10.73 (1H, s), 9.03 (1H, s), 8.44 (1H, s), 8.12 (2H, d, J 9.0 Hz), 7.96–7.90 (3H, m), 7.80 (1H, d, 1 Hz), 7.55 (1H, d, J 8.0 hz), 7.35 (1H, q, J 9.0 Hz), 7.16 (1H, d, J 1.0 Hz) and 6.90 (1H, m).

2-Cyano-3-dimethylamino-1-(4-imidazol-1-ylphenyl) propen-1-one was prepared in a manner similar to the analogous starting material of Example 79, as a yellow solid (970 mg), m.p. 165°. δH (CDCl₃) 8.01 (1H, s), 7.96–7.92 (3H, m), 7.48–7.45 (2H, m), 7.33 (1H, t, J 1.4 hz), 7.23 (1H, d, J 1.0 Hz), 3.52 (3H, s) and 3.34 (3H, s).

3-Hydroxy-3-(4-imidazol-1-ylphenyl)acrylonitrle, sodium salt was prepared from 5-(4-imidazol-1-ylphenyl) isoxazole (1.22 g, 5.78 mmol) and sodium (133 mg, 5.78 mmol) in ethanol (15 mL) in a manner similimar to the analogous starting material of Example 8, as a beige solid (1.14 g), m.p. 286°.

5-(4-imidazol-1-ylphenyl)isoxazole was prepared by treating a solution of 3-dimethylamino-1-[(4-imidazol-1-yl) phenyl]propen-1-one (1.64 g, 6.8 mmol) in MeOH with hydroxylamine-O-sulphonic acid (831 mg, 7.35 mmol) at ambient temperature for 16 h. A further quantity of hydroxylamine-O-sulphonic acid (831 mg, 7.35 mmol) was added and stirring continued for 3 h. The reaction was then treated with saturated NaHCO₃ solution, the resulting solution being collected by filtration and washed with water and diethyl ether to give the desired material (1.08 g) as a pink solid, m.p. 168°. δH (d⁶ DMSO) 8.67 (1H, d, J 1.8 Hz), 3.89 (1H, s), 8.03–7.99 (2H, m), 7.86–7.84 (3H, m), 7.14 (1H, s) and 7.10 (1H, d, J 1.9 Hz).

EXAMPLE 80

N-[3-(5-Cyano-4-thiophen-2-ylpyrimidin-2-ylamino) phenyl]-4-(4-methylpiperazin-1-ylmethyl)benzamide A solution of N-3-aminophenyl-5-cyano-4-thien-2-ylpyrimidine-2-amine (300 mg, 1.0 mmol) and 4-(4-methylpiperazin-1-yl)methylbenzoic acid, lithium salt (300 mg, 1.0 mmol) in DMF (10 mL) was treated with 1-(3-dimethylaminopropyl)-3-ethylcarbodiimide (307 mg, 1.6 mmol), 1-hydroxybenzotriazole (216 mg, 1.6 mmol) and N-methylmorpholine (350 ml, 3.2 μmol) and the resulting mixture was stirred at ambient temperature for 48 h. The reaction was then concentrated under reduced pressure and the resulting residue partitioned between ethyl acetate and saturated brine. The organic phase was dried (MgSO4), concentrated under reduced pressure and the resulting residue recrystallised from ethyl acetate-ether-MeOH (4:4:1) to give the title compound (312 mg) as a colourless solid, m.p. 208–209°. δH (d⁶ DMSO) 10.48 (1H, bs), 10.23 (1H, s), 8.89 (1h,s), 8.28 (1H, d, J 3.5 Hz), 8.13 (1H, m), 7.98 (1H, d, J 4.8 Hz), 7.90 (2H, d, J 8.2 Hz), 7.60 (1H, bs), 7.43 (3H, d, J 8.2 Hz), 7.36–7.30 (2H, s), 3.52 (2H, s), 2.37 (8H, bs) and 2.15 (3H,s).

N-3-Aminophenyl-5-cyano-4-thien-2-ylpyrimidine-2-amine was prepared by heating a solution of 5-cyano-N-3-nitrophenyl-4-thien-2-ylpyrimidine-2-amine (2.77 g, 8.57 mmol) and tin(II)chloride dihydrate (7.73 g, 34.05 mmol) in ethanol (160 mL) at reflux for 18 h. On cooling the reaction was concentrated under reduced pressure and partitioned between CH₂Cl₂ and 2M NaOH. The organic phase was dried (MgSO₄) and evaporated to give the desired material (320 mg) as a yellow solid, m.p. 221–222°. δH (d⁶ DMSO) 10.16 (1H, s), 8.83 (1H, s), 8.24 (1H, d, J 3.9 Hz), 7.97 (1H, d, J 5.1 Hz), 7.32 (1H, dd, J 5.0, 4.0 Hz), 6.97 (3H, bm), 6.31 (1H, m) and 5.04 (2H, bs).

5-Cyano-N-3-nitrophenyl-4-thien-2-ylpyrimidine-2-amine was prepared from 2-cyano-3-dimethylamino-1-thien-2-ylpropen-1-one (3.20 g, 15.51 mmol), 3-nitrophenylguanidinium nitrate (3.74 g, 15.53 mmol) and sodium hydroxide (652 mg, 7.82 mmol) to give the desired material (841 mg) as an off-white solid, m.p.275–277°. δH (d⁶ DMSO) 10.87 (1H, bs), 8.98 (1H, s), 8.90 (1H, bs), 8.31–8.29 (1H, m), 8.09–8.05 (2H, m), 7.91 (1H, dd, J 7.7,2.0 Hz), 7.64 (1H, t ,J 8.1 Hz) and 7.37–7.35 (1H, m).

4-(4-Methylpiperazin-1-yl)methylbenzoic acid, lithium salt was prepared by stirring methyl 4-(4-methylpiperazin-1-yl)methylbenzoate (845 mg, 3.41 mmol) and lithium hydroxide monohydrate (300 mg, 7.15 mmol) in THF-H2O [50% v/v] (14 mL) at room temperature for 16 h. The solvent was removed under reduced pressure to give the desired material (799 mg) as a white solid, m.p. 230°. δH (d⁶ DMSO) 7.80 (2H, d, J 8.1 Hz), 7.16 (2H,d, J 8.1 Hz), 3.41 (2H, s), 2.30 (8H, bs) and 2.12 (3H, s).

Methyl 4-(4-methylpiperazin-1-yl)methylbenzoate was prepared by heating methyl (4-bromomethyl)benzoate (2.3 g, 10.0 mmol) and 1-methylpiperazine (1.0 g, 10.0 mmol) in DMF (10 mL) for 3 h. The reaction was concentrated under reduced pressure and the residue dried under high vacuum to give the desired product (1.2 g) as a white solid, m.p.152°. δH (d⁶ DMSO) 7.90 (2H, d, J 8.2 Hz), 7.43 (2H, d, J 8.2 Hz), 3.83 (3H, s), 2.67 (4H, bs), 2.47 (4H, bs) and 2.40 (3H, s).

EXAMPLES 81 TO 104

The compounds of Examples 81 to 104 were prepared by solution phase parallel synthesis performed on a Quest 210 Personal Synthesizer (Argonaut Technologies, San Carlos, Calif.,USA) employing the following intermediate:

2-Chloro-5-Cyano-4-phenylpyrimidine 5-cyano-4-phenyl-1 (H)-pyrimidin-2-one (0.83 g, 4.21 mmol) was heated in phosphorous oxychloride (20 mL) and DMF (~1 ml) at 115° for 24 h. On cooling, the reaction was concentrated under reduced pressure and the residue poured into a cooled saturated NaHCO$_3$ solution. This was extracted with ethyl acetate, the combined organic phases dried (MgSO$_4$) and evaporated to give the desired material (0.79 g) as a yellow solid m.p. 79–81°.

The pyrimidin-2-one was prepared by treating a solution of 2-amino-5-cyano-4-phenylpyrimidine (2.0 g, 10.2 mmol) in 50% concentrated H$_2$SO$_4$-water (v/v) at room temperature, with a solution of sodium nitrite (2.82 g, 40.8 mmol) in water (30 ml) over 1 h. The reaction was allowed to stir overnight at room temperature, before additional sodium nitrite (2.82 g, 10.2 mmol) was added and stirring continued for 3 h. After this time ammonium hydroxide (33% aqueous) was added to pH9, and the resulting precipitate collected and dried to give the desired material (2.2 g) as a white solid m.p. 220–222°.

2-Amino-5-cyano-4-phenylpyrimidine was prepared from guanidine carbonate (1.57 g, 17.5 mmol), 1-phenyl-2-cyano-3-dimethylaminopropen-1-one (3.5 g, 17.5 mmol) and sodium hydroxide (720 mg, 19.3 mmol) in a similar method to the compound of Example 1, as an off-white solid, m.p. 147°.

EXAMPLE 81

5-Cyano-4-phenyl-N-quinol-6-ylpyrimidine-2-amine

To a Quest 5 ml Teflon reaction vessel (RV), was added 6-aminoquinoline (61 μmol) and a solution of 2-chloro-5-cyano4-phenylpyrimidine (10 mg, 47 mmol) in 1,4-dioxan (1.5 mL). The resulting mixture was heated (85°) with agitation every 10 min for 48 h. After this time PS-isocyanate resin (Argonaut Technologies) (100 mg, 150 μmol) and PS-trisamine (Argonaut Technologies) (50 mg, 150 mmol) were added to the reaction vessel and the reaction was agitated every 10 min at 55° for 18 h. The reaction was diluted with THF (~3 ml) and then filtered into a pre-weighed vial, the resins being further washed with dichloromethane. The combined filtrates were evaporated under reduced pressure overnight and the residue taken up in DMSO (500 μl). The residue was purified using semi-preparitive HPLC (System; Waters HPLC Pump Module 600E, Waters 486 detector with semi-prep flow cell and Waters 717 Autosampler (250 μl). Column; 150×10 mm Luna C18 (2) 5 μm. Conditions; 90% [0.1% TFA-water] 10% [0.1% TFA-acetonitrile] to 10% [0.1% TFA-water] 90% [0.1% TFA-acetonitrile] at 5.0 mlmin$^{-1}$ with a run time of 15 min at ambient temperature) to give the title compound. HPLC-MS Retention time 4.2 mins (MH)+324.

HPLC-MS Conditions

HPLC-MS was performed on a Hewlett Packard Binary Pump 1100/MSD ES Single Quadropole using a Luna C18(2), 50×4.6 mm column, running a gradient of 95% [20 mM ammonium formate pH3.5] 5% [acetonitrile-0.1% TFA] to 5% [20 mM ammonium formate pH3.5] 95% [acetonitrile-0.1% TFA] at 0.8 mlmin$^{-1}$ with a run time of 5 min. MS acquired at 70V in positive ion API-electrospray mode of ionisation, scannining from 150–750 amu.

EXAMPLE 82

N-(3-Chloro-4-methylphenyl)-5-cyano-4-phenylpyrimidine-2-amine

3-Chloro-4-methylaniline gave the title compound
HPLC-MS Retention time 5.13 mins (MH)+322

EXAMPLE 83

N-(3-Acetylphenyl)-5-cyano-4-phenylpyrimidine-2-amine

3-Aminoacetophenone gave the title compound
HPLC-MS Retention time 4.42 mins (MH)+315

EXAMPLE 84

N-(4-Chloro-3-trifluoromethylphenyl)-5-cyano-4-phenylpyrimidine-2-amine

4-Chloro-3-trifluoromethylaniline gave the title compound
HPLC-MS Retention time 5.19 mins (MH)+376

EXAMPLE 85

5-Cyano-N-(4-methoxycarbonylphenyl)-4-phenylpyrimidine-2-amine

Methyl 4-aminobenzoate gave the title compound
HPLC-MS Retention time 4.58 mins (MH)+331

EXAMPLE 86

N-(4-Carboxymethylphenyl)-5-cyano-4-phenylpyrimidine-2-amine

4-Aminophenylacetic acid gave the title compound
HPLC-MS Retention time 4.0 mins (MH)+331

EXAMPLE 87

5-Cyano-N-[4-(2-N,N-diethylaminoethylaminocarboxy)phenyl]-4-phenylpyrimidine-2-amine Procainamide hydrochloride gave the title compound
HPLC-MS Retention time 3.33 mins (MH)+415.5

EXAMPLE 88

N-(3-Carboxyphenyl)-5-cyano-4-phenylpyrimidine-2-amine

3-Aminobenzoic acid gave the title compound
HPLC-MS Retention time 4.03 mins (MH)+317

EXAMPLE 89

5-Cyano-4-phenyl-N-[3-(1,1,2,2-tetrafluoroethoxyphenyl)]pyrimidine-2-amine 1,1,2,2-Tetrafluoroethoxyaniline gave the title compound
HPLC-MS Retention time 4.77 mins (MH)+389

EXAMPLE 90

5-Cyano-N-(3-oxazol-5-ylphenyl)-4-phenylpyrimidine-2-amine

3-Oxazol-5-ylaniline gave the title compound
HPLC-MS Retention time 4.4 mins (MH)+340

EXAMPLE 91

5-Cyano-N-[2-(4-fluorophenoxy)pyridin-5-yl)-4-phenylpyrimidine-2-amine

5-Amino-2-(4-fluorophenoxy)pyridine gave the title compound
HPLC-MS Retention time 4.72 mins (MH)+384

EXAMPLE 92

5-Cyano-N-(4-methoxycarbonylthien-3-yl)-4-phenylpyrimidine-2-amine

Methyl 3-aminothiophene-4-carboxylate gave the title compound
HPLC-MS Retention time 5.09 min (MH)+337

EXAMPLE 93

5-Cyano-N-(2-morpholinopyridin-5-yl)-4-phenylpyrimidine-2-amine

2-Morphilino-5-aminopyridine gave the title compound
HPLC-MS Retention time 4.1 min (MH)+359

EXAMPLE 94

5-Cyano-N-[4-(6-methylbenzothiazol-2-yl)phenyl]]pyrimidine-2-amine

2-Amino-6-methylbenzothiazole gave the title compound
HPLC-MS Retention time 5.7 min (MH)+420.5

EXAMPLE 95

5-Cyano-N-(4-isopropyl-2-methylphenyl)-4-phenylpyrimidine-2-amine 4-isopropyl-2-methylaniline gave the title compound
HPLC-MS Retention time 5.35 mins (MH)+329

EXAMPLE 96

5-Cyano-N-(3-methanesulphonyl)phenyl-4-phenylpyrimidine-2-amine 3-(Methanesulphonyl)aniline gave the title compound
HPLC-MS Retention time 4.12 mins (MH)+351

EXAMPLE 97

5-Cyano-N-[2-(3,5-dimethylpyrazol-1-yl)pyridin-3-yl)4-phenylpyrimidine-2-amine

3-Amino-2-(3,5-dimethylpyrazol-1-yl)pyridine gave the title compound
HPLC-MS Retention time 5.12 mins (MH)+368

EXAMPLE 98

5-Cyano-N-(4-ethylphenyl)-4-phenylpyrimidine-2-amine

4-Ethylaniline gave title compound
HPLC-MS Retention time 4.99 mins (MH)+301

EXAMPLE 99

5-Cyano-N-(8-methoxyquinol-6-yl)-4-phenylpyrimidine-2-amine

6-Amino-8-methoxyquinoline sgave the title compound
HPLC-MS Retention time 3.96 mins (MH)+354

EXAMPLE 100

N-(4-n-Butoxyphenyl)-5-cyano-4-phenylpyrimidine-2-amine 4-n-Butoxyaniline gave the title compound
HPLC-MS Retention time 5.19 mins (MH)+345.4

EXAMPLE 101

5-Cyano-N-(2-oxo-2-phenylethyl)4-phenylpyrimidine-2-amine

2-Oxo-2-phenethylamine gave the title compound
HPLC-MS Retention time 4.4 mins (MH)+315

EXAMPLE 102

5-Cyano-N-–3-n-(4-methylpiperazin-1-yl)propyl]-4-phenylpyrimidine-2-amine

3-N-(4-Methylpiperazin-1-yl)propylamine gave the title compound
HPLC-MS Retention time 3.1 mins (MH)+337

EXAMPLE 103

N-(Adamant-1-yl)-5-Cyano-4-phenylpyrimidine-2-amine

1-Adamantanamine gave the title compound
HPLC-MS Retention time 6.0 mins (MH)+331

EXAMPLE 104

5-Cyano-N-(2-morpholinoethyl)-4-phenylpyrimidine-2-amine

2-Morpholinoethylamine gave the title compound
HPLC-MS Retention time 3.1 mins (MH)+310

EXAMPLE 105

4-[4-(1-Amino-1-methylethyl)phenyl]-5-cyano-N-[4-(1,2,4-triazol-1-yl)phenyl]pyrimidine-2-amine citrate The compound of Example 11 (100 mg, 0.25 mmol) was dissolved in acetone/methanol (25 mL, 1:1 v/v) and to this citric acid (52.5 mg, 0.25 mmol) was added. The resulting solution was diluted with diethyl ether (20 ml) to give the title compound (145 mg). $\delta$H (d$^6$ DMSO) 10.73 (1H, bs), 9.21 (1H, s), 9.01 (1H, s), 8.20 (1H, s), 8.02 (2H, d, J 8.4 Hz), 7.94 (2H, d, J 8.7 Hz), 7.80 (2H, d, J 7.4 Hz, 7.78 (2H, d, J 8.3 Hz), 2.49 (4H, m) and 1.65 (6H, s)

Biological Activity

The following assays were used to demonstrate the activity and selectivity of compounds according to the invention:

The activity of the comounds against KDR kinase and a FGFR Kinase [FGFR2 kinase] can be determined in the following two assays:
KDR Kinase and FGFr2 Kinase The activities of recombinant KDR kinase and FGFr2 kinase were determined by measuring their ability to transfer the γ-phosphate from [$^{33}$P]ATP to polyglutamic acid-tyrosine (pEY).

The assay methodology employed for both kinases is identical except that in the assay of KDR kinase the diluent used throughout was 20 mM HEPES pH 7.25 containing 2 mM MnCl$_2$, 2 mM MnCl$_2$, 5 mM DTT and 0.05% Brij 35, whereas in the FGFr2 assay 10 mM MnCl$_2$ is used instead of 2 mM MnCl$_2$ and 2 mM MnCl$_2$.

The assay was conducted in a total volume of 202 μl containing 1–10 ng kinase, 5 μg/ml pEY (4:1) (Sigma, UK), 1 μM ATP (containing ~50,000 cpm [$^{33}$P]ATP (Amersham International, UK) (Sigma, UK) and test inhibitors at the appropriate concentration. The test inhibitors were dissolved in DMSO and added such that the final concentration of DMSO in the assay did not exceed 2% (v/v). The assay was initiated by addition of kinase and terminated after 10 minutes incubation at room temperature by addition of 50 μl of 20 mM HEPES pH 7.25 containing 0.125M EDTA and 10 mM ATP. A 200 μl aliquot was applied to the well of a Millipore (UK) MAFC filter plate containing 100 μl of 30% (w/v) trichloroacetic acid (TCA). The plate was then placed on a suitable manifold and connected to a vacuum. After complete elimination of the liquid each well was washed under vacuum using five volumes (100 μl per wash) of 10% (w/v) TCA and finally two volumes (100 μl per wash) of ethanol. The bottom of the filter plate was then sealed and 100 μl per well of Ultima Gold (Beckham, UK) scintillant was added to each well. The readioactivity was measured using an appropiate scintillation counter such as a Wallac Trilux or Packard TopCount. The $IC_{50}$ value for each inhibitor was obtained from log dose inhibition curves fitted to the four-parameters logistic equation.

In this assay compounds accoding to the invention have $IC_{50}$ values of around 1 μM and below, the most active compounds having values of 100 nM and below.

The selectivity of compounds according to the invention can be determined in the following assays:

p56$^{lck}$ Kinase Assay

The tyrosine kinase activity of p56$^{lck}$ was determined using a RR-src peptide (RRLIEDNEYTARG) and [γ-$^{33}$P] ATP as substrates. Quantitation of the $^{33}$P-phosphorylated peptide formed by the action of p56$^{lck}$ was achieved using an adaption of the method of Geissler et al (J. Biol. Chem. (1990) 265, 22255–22261).

All assays were performed in 20 mM HEPES pH 7.5 containing 10 mM $MgCl_2$, 10 mM $MnCl_2$, 0.05% Brij, 1 μM ATP (0.5 μCi[γ-$^{33}$P]ATP) and 0.8 mg/ml RR-src. Inhibitors in dimethylsulphoxide (DMSO) were added such that the final concentration of DMSO did not exceed 1%, and enzyme such that the consumption of ATP was less than 10%. After incubation at 30° C. for 15 min, the reaction was terminated by the addition of one-third volume of stop reagent (0.25 mM EDTA and 33 mM ATP in $dH_2O$). A 15 μl aliquot was removed, spotted onto a P-30 filtermat (Wallac, Milton Keynes, UK), and washed sequentially with 1% acetic acid and de-ionised water to remove ATP. The bound $^{33}$P-RR-src was quantitated by scintillation counting of the filtermat in a Betaplate scintillation counter (Wallac, Milton Keynes, UK) after addition of Meltilex scintillant (Wallac, Milton Keynes, UK).

The dpm obtained, being directly proportional to the amount of $^{33}$P-RR-src produced by p56$^{lck}$, were used to determine the $IC_{50}$ for each compound. The $IC_{50}$ was defined as the concentration of compound required to reduce the production of $^{33}$P-RR-src by 50%.

In this test, compounds according to the invention have $IC_{50}$ values of 10 μM and above.

Zap-70 Kinase Assay

The tyrosine kinase activity of Zap-70 was determined using a capture assay based on that employed above for p56$^{lck}$. The RR-src peptide was replaced with polyGlu-Tyr (Sigma; Poole, UK) at a final concentration of 17 μg/ml. After addition of the stopped reaction to the filtermat, trichloroacetic acid 10% (w/v) was employed as the wash reagent instead of acetic acid and a final wash in absolute ethanol was also performed before scintillation counting. $IC_{50}$ values were determined as described above in the p56$^{lck}$ assay.

In this test the compounds of the invention have $IC_{50}$ values of around 10 μM and above.

EGFr Kinase Assay

The tyrosine kinase activity of the EGF receptor (EGFr) was determined using a similar methodology to the p56$^{lck}$ kinase assay, except that the RR-src peptide was replaced by a peptide substrate for EGFr obtained from Amersham International pic (Little Chalfont, UK) and used at the manufacturer's recommended concentration. $IC_{50}$ values were determined as described previously in the p56$^{lck}$ assay.

Protein Kinase C Assay

Inhibitor activity against protein kinase C (PKC) was determined using PKC obtained from Sigma Chemical Company (Poole, UK) and a commercially available assay system (Amersham International pic, Amersham, UK). Briefly, PKC catalyses the transfer of the γ-phosphate ($^{32}$p) of ATP to the threonine group on a peptide specific for PKC. Phosphorylated peptide is bound to phosphocellulose paper and subsequently quantified by scintillation counting. The inhibitor potency is expressed as either (i) the concentration required to inhibit 50% of the enzyme activity ($IC_{50}$) or (ii) the percentage inhibition achieved by 10 μM inhibitor.

In this test the compounds of the invention have $IC_{50}$ values of around 10 μM and above.

What is claimed is:

1. A compound of formula (1):

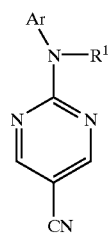

(1)

wherein

Ar is an optionally substituted aromatic or heteroaromatic group;

$R^1$ is a hydrogen atom or a straight or branched chain alkyl group;

$R^2$ is a group —$X^1$—$R^3$ in which $X^1$ is a direct bond, and $R^3$ is an optionally substituted aliphatic optionally interrupted by one or two heteroatoms or heteroatom-containing groups, cycloalkyl, heterocyclyl, aromatic or heteroaromatic group;

and the salts, solvates, hydrates and N-oxides thereof.

2. A compound according to claim 1 in which $R^3$ is an optionally substituted aromatic or heteroaromatic group, said heteroaromatic group containing one or two ring oxygen, sulphur and/or nitrogen atoms.

3. A compound according to claim 2 wherein $R^3$ is a phenyl, thienyl, thiazolyl, indolyl or pyridyl group optionally substituted by one, two or three —$R^{4b}$ or —Alk($R^{4b}$)$_m$ substituents in which $R^{4b}$ is a halogen atom, or an amino (—$NH_2$), substituted amino, nitro, cyano, hydroxyl (—OH), substituted hydroxyl, formyl, carboxyl (—$CO_2H$), $CO_2Alk^1$ (wherein $Alk^1$ is a straight or branched, optionally substituted $C_{1-8}$alkyl group, a $C_{6-12}$aryl$C_{1-8}$alkyl group, a $C_{6-12}$aryl group, a $C_{6-12}$aryloxy$C_{1-8}$alkyl group, an optionally substituted $C_{1-8}$alkanoyloxy$C_{1-8}$alkyl group, or a $C_{6-12}$aroyloxy$C_{1-8}$alkyl group), thiol (—SH), substituted thiol, —$COR^5$ (where $R^5$ is a —Alk($R^4$)$_m$, aryl, optionally substituted monocyclic or bicyclic $C_{6-12}$ aromatic group, or an optionally substituted $C_{1-9}$ heteroaromatic group), —$CSR^5$, —$SO_3H$, —$SO_2R^5$, —$SO_2NH_2$, —$SO_2NHR^5$, —$SO_2N(R^5)_2$, —$CONH_2$, —$CSNH_2$, —$CONHR^5$, —$CSNHR^5$, —$CON(R^5)_2$, —$CSN(R^5)_2$, —$NHSO_2H$, —$NHSO_2R^5$, —$N(SO_2R^5)_2$, —$NHSO_2NH_2$, —$NHSO_2NHR^5$, $NHSO_2N$ ($R^5$)$_2$,—$NHCOR^5$, —$NHCONH_2$, —$NHCONHR^5$, —$NHCON$ ($R^5$)$_2$, —$NHCSR^5$, —$NHC(O)OR^5$, or optionally substituted cycloalkyl, heterocyclyl, aryl, monocyclic or bicyclic $C_{6-12}$ aromatic group, or $C_{1-9}$ heteroaromatic group; Alk is a straight or branched $C_{1-6}$ alkylene, $C_{2-6}$, alkenylene or $C_{2-6}$, alkynylene chain, optionally interrupted by one, two or three —O— or —S— atoms or groups selected from —S(O)—, —S(O)$_2$— or —N(R$^6$)— (where R$^6$ is a hydrogen atom or a straight or branched chain $C_{1-6}$ alkyl group); and m is zero or an integer 1, 2 or 3.

4. A compound which is:

5-Cyano-4-phenyl-N-(3,4,5-trimethoxyphenyl)pyrimidine-2-amine;

5-Cyano-N-[4-(2-imidazol-1-ylethyl)phenyl]-4-(4-methoxcarbonylphenyl)pyrimidine-2-amine;

5-Cyano-4-(4-hydroxymethylphenyl)-N-(3,4,5-trimethoxy-phenyl)pyrimidine-2-amine;

5-Cyano-4[(4-N,N-diethylaminomethyl)phenyl]-N-(3,4,5-trimethoxyphenyl)pyrimidine-2-amine;

5-Cyano-4-[2-(3(R)-dimethylaminopyrrolidin-1-yl)pyridin-5-yl]-N-(indazol-5-yl)pydmidine-2-amine;

4-[4-(1-Amino-1-methylethyl)phenyl]-5-cyano-N-(indazol-5-yl)-pyrimidine-2-amine;

4-[4-(1-Amino-1-methylethyl)phenyl]-5-cyano-N-(3,4,5-trimethoxy-phenyl)pyrimidine-2-amine;

5-Cyano-N-[4-(2-N,N-diethylaminoethylaminocarboxy) phenyl]-4-phenylpyrimidine-2-amine;

5-Cyano-4-phenyl-N-{4-[2-(2-ethylimidazol-1-yl)ethyl] phenyl}-pyrimidine-2-amine;

4-[4-(1-Amino-1-methylethyl)phenyl]-5-cyano-N-4(1,2,3-triazol-1-yl)-phenyl]pyrimidine-2-amine;

4-[4-(1-Amino-1-methylethyl)phenyl]-5-cyano-N-{4-[2-(2-ethylimidazol-1-yl)ethyl]phenyl}pyrimidine-2-amine;

N-[3-(5-Cyano-4-thiophen-2-ylpyrimidin-2-ylamino) phenyl]-4-(4-methylpiperazin-1-ylmethyl)benzamide;

4-[3-(1-Amino-1-methylethyl)phenyl]-5-cyano-N-{4-[2-(2-methyl-imidazol-1-yl)ethyl]phenyl}pyrimidine-2-amino;

5-Cyano-4-[4-(imiadzol-1-yl)methyl]phenyl-N-(3,4,5-trimethoxy-phenyl)-pyrimidine-2-amino;

and the salts, solvates, hydrates and N-oxides thereof.

5. A compound which is:

4-[4-(1-Amino-1-methylethyl)phenyl]-5-cyano-N-[4(1,2,4-triazol-1-yl)phenyl]pyrimidine-2-amine;

5-Cyano-N-[4-(1,2,4-triazol-1-yl)phenyl]-4-[4-(1-dimethylamino-1-methylethyl)phenyl]pyrimidine-2-amine;

4-[4-(1-Amino-1-methylethyl)phenyl]-5-cyano-N-(4-fluorophenyl)pyrimidine-2-amine;

4-[4-(1-Amino-1-methylethyl)phenyl]-5-cyano-N-{4-[2-piperidin-1-ylethyl]phenyl}pyrimidine-2-amine;

4-[4-(1-Amino-1-methylethyl)phenyl]-5-cyano-N-[4-(2-imidazol-1-ylethyl)phenyl]pyrimidine-2-amine;

4-[4-(1-Amino-1-methylethyl)phenyl]-5-cyano-N-[4-(2-morpholinoethyl)phenyl]pyrimidine-2-amine;

4-[4-(1-Amino-1-methylethyl)phenyl]-5-cyano-N-[3-(2-morpholinoethyl)phenyl]pyrimidine-2-amine;

5-Cyano-4-[4-(1-methyl-1-pyrrolidin-1-ylethyl)phenyl]-N-(4-fluorophenyl)pyrimidine-2-amine;

5-Cyano-4-{2-([2-(diethylamino)ethyl]amino)pyridin-5-yl}-N-(4-fluorophenyl)pyrimidine-2-amine;

4-[4-(1-Amino-1-methylethyl)phenyl]-5-cyano-N-(3-fluorophenyl)pyrimidine-2-amine;

and the salts, solvates, hydrates and N-oxides thereof.

* * * * *